US010468605B2

(12) United States Patent
Yoon et al.

(10) Patent No.: US 10,468,605 B2
(45) Date of Patent: *Nov. 5, 2019

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Seung-Hee Yoon, Seoul (KR);
Sung-Hoon Joo, Paju-si (KR);
Seon-Keun Yoo, Gunpo-si (KR);
Ji-Cheol Shin, Seoul (KR)

(73) Assignee: LG DISPLAY CO., LTD., Seoul (KR)

(*) Notice: Subject to any disclaimer, the term of this patent is extended or adjusted under 35 U.S.C. 154(b) by 8 days.

This patent is subject to a terminal disclaimer.

(21) Appl. No.: 15/717,414

(22) Filed: Sep. 27, 2017

(65) Prior Publication Data

US 2018/0090686 A1    Mar. 29, 2018

(30) Foreign Application Priority Data

Sep. 29, 2016    (KR) .................. 10-2016-0125311

(51) Int. Cl.
| | | |
|---|---|---|
| H01L 51/00 | (2006.01) | |
| H01L 27/32 | (2006.01) | |
| C07D 401/14 | (2006.01) | |
| C07D 405/14 | (2006.01) | |
| C07D 409/14 | (2006.01) | |
| C07F 7/08 | (2006.01) | |
| H01L 51/50 | (2006.01) | |
| H01L 51/52 | (2006.01) | |

(52) U.S. Cl.
CPC ........ *H01L 51/0067* (2013.01); *C07D 401/14* (2013.01); *C07D 405/14* (2013.01); *C07D 409/14* (2013.01); *C07F 7/0816* (2013.01); *H01L 27/322* (2013.01); *H01L 27/3244* (2013.01); *H01L 51/0052* (2013.01); *H01L 51/0054* (2013.01); *H01L 51/0072* (2013.01); *H01L 51/0073* (2013.01); *H01L 51/0074* (2013.01); *H01L 51/0094* (2013.01); *H01L 51/504* (2013.01); *H01L 51/5072* (2013.01); *H01L 51/5092* (2013.01); *H01L 51/5278* (2013.01)

(58) Field of Classification Search
CPC ............. H01L 51/0067; H01L 51/0052; H01L 27/322; H01L 27/3244; H01L 51/0094; H01L 51/0074; H01L 51/0073; H01L 51/0054; H01L 51/0072; H01L 51/5278; H01L 51/5092; H01L 51/504; H01L 51/5072; C07F 7/0816; C07D 405/14; C07D 401/14; C07D 409/14
USPC ....................................................... 428/690
See application file for complete search history.

(56) References Cited

U.S. PATENT DOCUMENTS

| | | | | |
|---|---|---|---|---|
| 10,068,948 | B2* | 9/2018 | Yun | ............ H01L 51/5092 |
| 2015/0041789 | A1 | 2/2015 | Ozeki | |
| 2016/0141511 | A1 | 5/2016 | Kim et al. | |
| 2016/0260901 | A1 | 9/2016 | Kim et al. | |
| 2016/0372524 | A1* | 12/2016 | Yun | ............ H01L 51/5092 |
| 2017/0092870 | A1 | 3/2017 | Kim et al. | |
| 2017/0092871 | A1 | 3/2017 | Kim et al. | |
| 2018/0033989 | A1* | 2/2018 | Lee | ............ C09K 11/06 |

FOREIGN PATENT DOCUMENTS

| | | |
|---|---|---|
| CN | 106892901 A | 6/2017 |
| EP | 1930329 A1 | 6/2008 |
| EP | 2269987 A1 | 1/2011 |
| EP | 2361909 A1 | 8/2011 |
| EP | 2468731 A1 | 6/2012 |
| EP | 3015527 A1 | 5/2016 |
| EP | 3107131 A1 | 12/2016 |
| JP | 2010-155826 A | 7/2010 |
| JP | 2011-126851 A | 6/2011 |
| JP | 2016-152239 A | 8/2016 |
| JP | 2016-155795 A | 9/2016 |
| KR | 10-2008-0039941 A | 5/2008 |
| KR | 10-2016-0051133 A | 5/2016 |

(Continued)

OTHER PUBLICATIONS

CAS reg. No. 2010128-39-7, Oct. 11, 2016. (Year: 2016).*

(Continued)

Primary Examiner — Douglas J McGinty
(74) Attorney, Agent, or Firm — Birch, Stewart, Kolasch & Birch, LLP

(57) ABSTRACT

The present invention provides an organic compound represented by:

an organic light emitting diode and an organic light emitting display device using the organic compound. The organic compound of the present invention is capable of reducing a driving voltage of an organic light emitting diode and improving an emitting efficiency and a lifetime of the organic light emitting diode and the organic light emitting display device including the organic compound.

18 Claims, 16 Drawing Sheets

(56) References Cited

FOREIGN PATENT DOCUMENTS

| KR | 10-2016-0090262 A | 7/2016 |
|----|-------------------|--------|
| WO | WO 2016/002864 A1 | 1/2016 |
| WO | WO 2016/024745 A2 | 2/2016 |
| WO | WO 2016/068441 A1 | 5/2016 |

OTHER PUBLICATIONS

Constable et al., "Metallostars containing {Ru(bpy)3} motifs," Inorganica Chimica Acta, vol. 300-302, XP008144990, Apr. 20, 2000, pp. 158-168.

* cited by examiner

ORGANIC COMPOUND, AND ORGANIC LIGHT EMITTING DIODE AND ORGANIC LIGHT EMITTING DISPLAY DEVICE INCLUDING THE SAME

The present application claims the priority benefit of Korean Patent Application No. 10-2016-0125311 filed in Republic of Korea on Sep. 29, 2016, which is hereby incorporated by reference into the present application.

BACKGROUND OF THE INVENTION

Field of the Invention

The present invention relates to an organic compound and more particularly to an organic compound being capable of reducing a driving voltage of an organic light emitting diode and improving an emitting efficiency and a lifetime of the organic light emitting diode and the organic light emitting display device including the organic compound.

Discussion of the Related Art

As requests for a flat panel display device having a small occupied area have increased, an organic light emitting display (OLED) device including an organic light emitting diode has been the subject of recent research and development.

The organic light emitting diode emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. Since the OLED device does not require a backlight assembly, the OLED device has low weight and low power consumption. Moreover, the OLED device can be operated at a voltage (e.g., 10V or below) lower than a voltage required to operate other display devices.

To efficiently inject the electron from the cathode into the EML, an organic light emitting diode for the OLED device may further include an electron injection layer (EIL) and an electron transporting layer (ETL) between the cathode and the EML. For example, an alkali halide material, e.g., LiF, or an organo-metallic material, e.g., lithium quinolate (Liq), may be used for the EIL. When an alkali metal or an alkali earth metal may be included in the EIL, the alkali metal (or the alkali earth metal) is diffused into the ETL with an electron such that the amount of the alkali metal (or the alkali earth metal) is reduced. As a result, the amount of the electron from the EIL into the ETL is decreased such that the driving voltage of the organic light emitting diode is increased and the emitting efficiency of the organic light emitting diode is decreased. In addition, the lifetime of the organic light emitting diode is decreased.

SUMMARY OF THE INVENTION

Accordingly, the present invention is directed to an organic compound and an organic light emitting diode and an organic light emitting display (OLED) device including the same that substantially obviate one or more of the problems due to limitations and disadvantages of the related art.

An object of the present invention is to provide an organic compound capable of preventing the decrease of an electron transporting/injection property and lifetime.

An object of the present invention is to provide an organic light emitting diode and an OLED device having improved electron transporting/injection property and lifetime.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is, represented by following Formula:

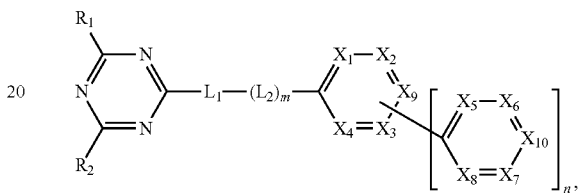

wherein each of $R_1$ to $R_2$ is independently selected from the group consisting of hydrogen, substituted or non-substituted $C_1$-$C_{20}$ alkyl, substituted or non-substituted $C_1$-$C_{20}$ alkoxy, substituted or non-substituted $C_4$-$C_{30}$ cycloalkyl, substituted or non-substituted $C_4$-$C_{30}$ heterocycloalkyl, substituted or non-substituted $C_6$-$C_{60}$ homoaryl, substituted or non-substituted $C_6$-$C_{60}$ heteroaryl, substituted or non-substituted $C_6$-$C_{60}$ homo-oxyaryl and substituted or non-substituted $C_6$-$C_{60}$ hetero-oxyaryl, wherein each of $L_1$ and $L_2$ is independently selected from the group consisting of substituted or non-substituted $C_6$-$C_{60}$ homoarylene and substituted or non-substituted $C_6$-$C_{60}$ heteroarylene, wherein m is 0 (zero) or 1, and n is 1 or 2, wherein one of $X_1$ to $X_4$ and $X_9$ is nitrogen atom, and the rest of $X_1$ to $X_4$ and $X_9$ are CH or $CR_3$, wherein one of $X_5$ to $X_8$ and $X_{10}$ is nitrogen atom, and the rest of $X_5$ to $X_8$ and $X_{10}$ are CH or $CR_4$, and wherein each of $R_3$ and $R_4$ is independently selected from the group consisting of hydrogen, substituted or non-substituted $C_1$-$C_{20}$ alkyl, substituted or non-substituted $C_1$-$C_{20}$ alkoxy, substituted or non-substituted $C_1$-$C_{20}$ alkyl amino, substituted or non-substituted $C_4$-$C_{30}$ cycloalkyl, substituted or non-substituted $C_4$-$C_{30}$ heterocycloalkyl, substituted or non-substituted $C_6$-$C_{60}$ homoaryl, substituted or non-substituted $C_6$-$C_{60}$ homo-oxyaryl and substituted or non-substituted $C_6$-$C_{60}$ hetero-oxyaryl.

In another aspect, an organic light emitting diode comprises first and second electrodes facing each other; an emitting material layer between the first and second electrodes; and an electron injection layer between the emitting material layer and the second electrode and including the above organic compound.

In another aspect, an organic light emitting diode comprises first and second electrodes facing each other; a first emitting part between the first and second electrodes and including a first emitting material layer and an electron transporting layer; a second emitting part between the first emitting part and the second electrode and including a second emitting material layer; and a first charge generation layer between the first and second emitting parts, wherein at least one of the electron transporting layer and the first charge generation layer includes the organic compound.

In another aspect, an organic light emitting display device comprises a substrate; the above organic light emitting diode: and a thin film transistor between the substrate and the organic light emitting diode and connected to the organic light emitting diode.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1:
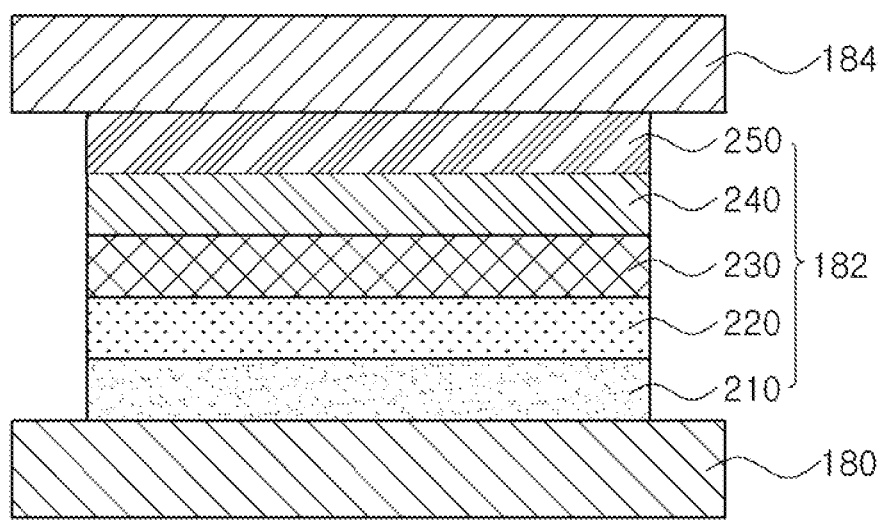
FIG. 1 is a schematic cross-sectional view of an organic light emitting diode according to a first embodiment of the present invention.

Reference will now be made in detail to the preferred embodiments, examples of which are illustrated in the accompanying drawings.

An organic compound of the present invention includes a triazin core (first core) and a bipyridine moiety (second core) directly or indirectly connected (or linked) to the triazin core. The organic compound is represented in Formula 1.

[Formula 1]

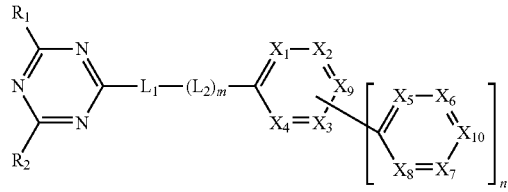

In Formula 1, each of $R_1$ to $R_2$ is independently selected from the group consisting of hydrogen, substituted or non-substituted $C_1$-$C_{20}$ alkyl, substituted or non-substituted $C_1$-$C_{20}$ alkoxy, substituted or non-substituted $C_4$-$C_{30}$ cycloalkyl, substituted or non-substituted $C_4$-$C_{30}$ heterocycloalkyl, substituted or non-substituted $C_6$-$C_{60}$ homoaryl, substituted or non-substituted $C_6$-$C_{60}$ heteroaryl, substituted or non-substituted $C_6$-$C_{60}$ homo-oxyaryl and substituted or non-substituted $C_6$-$C_{60}$ hetero-oxyaryl. In Formula 1, each of $L_1$ and $L_2$ is independently selected from the group consisting of substituted or non-substituted $C_6$-$C_{60}$ homoarylene and substituted or non-substituted $C_6$-$C_{60}$ heteroarylene. "m" is 0 (zero) or 1, and "n" is 1 or 2. In Formula 1, one of $X_1$ to $X_4$ and $X_9$ is nitrogen atom, and the rest of X1 to $X_4$ and $X_9$ are CH or $CR_3$. In addition, one of $X_5$ to $X_8$ and $X_{10}$ is nitrogen atom, and the rest of $X_5$ to $X_8$ and $X_{10}$ are CH or $CR_4$. Each of $R_3$ and $R_4$ may be independently selected from the group consisting of hydrogen, substituted or non-substituted $C_1$-$C_{20}$ alkyl, substituted or non-substituted $C_1$-$C_{20}$ alkoxy, $C_1$-$C_{20}$ alkyl amino, substituted or non-substituted $C_4$-$C_{30}$ cycloalkyl, substituted or non-substituted $C_4$-$C_{30}$ heterocycloalkyl, substituted or non-substituted $C_6$-$C_{60}$ homoaryl, substituted or non-substituted $C_6$-$C_{60}$ heteroaryl, substituted or non-substituted $C_6$-$C_{60}$ homo-oxyaryl and substituted or non-substituted $C_6$-$C_{60}$ hetero-oxyaryl.

For example, when m is 0, each of $R_3$ and $R_4$ may be hydrogen. On the other hand, when m is 1, $R_3$ may be hydrogen and $R_4$ may be heteroaryl (pyridine).

The Formula 1 may be represented by a Formula below.

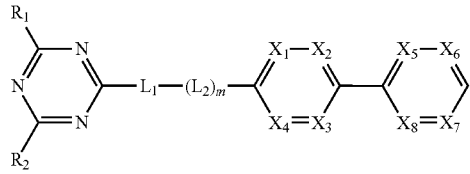

In Formula 1, each of $R_1$ to $R_2$ is independently selected from the group consisting of hydrogen, substituted or non-substituted $C_1$-$C_{20}$ alkyl, substituted or non-substituted $C_1$-$C_{20}$ alkoxy, substituted or non-substituted $C_4$-$C_{30}$ cycloalkyl, substituted or non-substituted $C_4$-$C_{30}$ heterocycloalkyl, substituted or non-substituted $C_6$-$C_{60}$ homoaryl, substituted or non-substituted $C_6$-$C_{60}$ heteroaryl, substituted or non-substituted $C_6$-$C_{60}$ homo-oxyaryl and substituted or non-substituted $C_6$-$C_{60}$ hetero-oxyaryl. In Formula 1, each of $L_1$ and $L_2$ is independently selected from the group consisting of substituted or non-substituted $C_6$-$C_{60}$ homoarylene and substituted or non-substituted $C_6$-$C_{60}$ heteroarylene, and "m" is 0 (zero) or 1.

In Formula 1, one of $X_1$ to $X_4$ is nitrogen atom, and the rest of X1 to $X_4$ are CH or $CR_3$. In addition, one of $X_5$ to $X_8$ is nitrogen atom, and the rest of $X_5$ to $X_8$ are CH or $CR_4$. Each of $R_3$ and $R_4$ may be independently selected from the group consisting of hydrogen, substituted or non-substituted $C_1$-$C_{20}$ alkyl, substituted or non-substituted $C_1$-$C_{20}$ alkoxy, $C_1$-$C_{20}$ alkyl amino, substituted or non-substituted $C_4$-$C_{30}$ cycloalkyl, substituted or non-substituted $C_4$-$C_{30}$ heterocycloalkyl, substituted or non-substituted $C_6$-$C_{60}$ homoaryl, substituted or non-substituted $C_6$-$C_{60}$ heteroaryl, substituted or non-substituted $C_6$-$C_{60}$ homo-oxyaryl and substituted or non-substituted $C_6$-$C_{60}$ hetero-oxyaryl.

For example, when m is 0, each of $R_3$ and $R_4$ may be hydrogen. On the other hand, when m is 1, $R_3$ may be hydrogen and $R_4$ may be heteroaryl (pyridine).

In the term of "substituted," the substituent may include halogen-substituted or non-substituted alkyl group, halogen-substituted or non-substituted alkoxy group, halogen, cyano group, carboxyl group, carbonyl group, amino group, alkylamino group, nitro group, hydrozyl group, sulfonate group, alkyl silyl group, alkoxy silyl group, cycloakyl silyl group, aryl silyl group, substituted or non-substituted aryl group or heteroaryl group, but it is not limited thereto.

The term "hetero," which is used in heteroaryl, heteroarylene, and so on, means that at least one carbon atom in the aromatic ring or alicyclic ring is substituted by a heteroatom being selected from the group consisting of nitrogen atom (N), oxygen atom (O) and sulfur atom (S).

For example, when each of $R_1$, $R_2$, $R_3$ and $R_4$ is an aromatic ring, each of $R_1$, $R_2$, $R_3$ and $R_4$ may be fused or non-fused homo-aromatic ring, such as phenyl, biphenyl, terphenyl, tetraphenyl, naphtyl, anthracenyl, indenyl, phenalenyl, phenanthrenyl, azulenyl, pyrenyl, fluorenyl, tetracenyl, indacenyl or spiro-fluorenyl, or fused or non-fused hetero-aromatic ring, such as pyrrolyl, pyridyl (or pyridinyl), pyrimidyl (pyrimidinyl), pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, quinolinyl, iso-quinolinyl, phthalazinyl, quinoxalinyl, cinnolinyl, quinazolinyl, phthalazinyl, benzoquinolinyl, benzo iso-quinolinyl, benzoqhinazolinyl, benzoquinoxalinyl, acrydinyl, phenanthrolinyl, furanyl, pyranyl, oxazinyl, oxazolyl, oxadiazolyl, triazolyl, dioxynyl, benzofuranyl, dibenzofuranyl, thio-pyranyl, thiazinyl, thiophenyl or N-substituted spiro-fluorenyl. In the organic compound of the exemplary embodiment of the present invention, each of $R_1$ and $R_2$ may be phenyl or biphenyl.

For example, each of $R_1$ to $R_4$ may be independently selected from the group consisting of phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyanopyridyl, alkoxypyridyl, silylpyridyl, phenylpyridyl, pyrimidyl, halopyrimidyl, cyanopyridyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridyl, phenylterpyridyl, triphenylenyl, fluoranthenyl and diazafluorenyl.

The carrier mobility of the organic compound may be controlled by $L_1$ and $L_2$ as the linker. Each of $L_1$ and $L_2$ may be an aromatic linker. For example, each of $L_1$ and $L_2$ may be one substituted or non-substituted $C_6$-$C_{60}$ homoarylene and substituted or non-substituted $C_6$-$C_{60}$ heteroarylene. Preferably, each of $L_1$ and $L_2$ may be one substituted or non-substituted $C_6$-$C_{60}$ homoarylene.

For example, each of $L_1$ and $L_2$ may be independently selected from a group consisting of phenylene, biphenylene, terphenylene, tetraphenylene, indenylene, naphthylene, azulenylene, indacenylene, acenaphthylene, fluorenylene, spiro-fluorenylene, phenalenylene, phenanthrenylene, anthracenylene, fluoranthrenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzoquinolinylene, benzo iso-quinolinylene, benzoquinazolinylene, benzoquinoxalinylene, cinnolinylene, phenanthridinylene, acridinylene, phenanthrolinylene, phenazinylene, benzoxazolylene, benzimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, dibenzofuranylene, dibenzothiophenylene, carbazolylene, benzocarbazolylene, dibenzocarbazolylene, indolocarbazolylene, indenocarbazolylene, imidazopyrimidinylene and imidazopyridinylene.

For example, each of $L_1$ and $L_2$ may be selected from the group consisting of phenylene, alkylphenylene, cyanophenylene, naphthylene, alkylnaphthylene, biphenylene, alkyl biphenylene, anthracenylene, pyrenylene, benzothiophenylene, benzofuranylene, dibenzothiophenylene, arylthiazolylene, dibenzofuranylene, fluorenylene and triphenylene.

When the number of rings of $L_1$ and $L_2$ is increased, the conjugation length of the organic compound is increased such that the energy band gap of the organic compound is decreased. Accordingly, the number of rings of $L_1$ and $L_2$ may be 1 to 3. To improve the electron injection/transporting property of the organic compound, $L_1$ and $L_2$ may be a 5-numbered atom ring to a 7-numbered atom ring, and beneficially a 6-numbered atom ring. In this instance, each of $L_1$ and $L_2$ may phenylene, pyrrolylene, imidazolylene, pyrazolylene, pyrazinylene, pyrimidinylene, pyridazinylene, furanylene or thiophenylene, but it is not limited thereto.

The organic compound in the Formula 1 may be one of the materials in Formula 2.

[Formula 2]

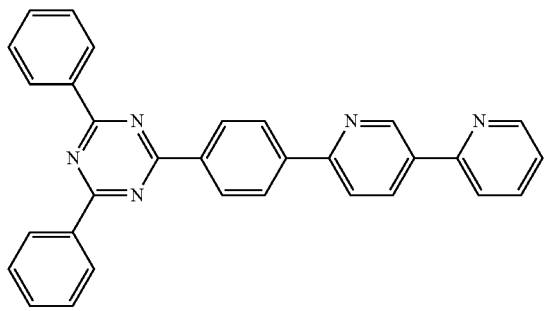

ET_01

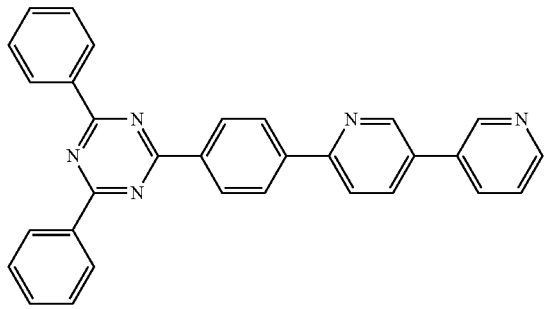

ET_02

ET_03
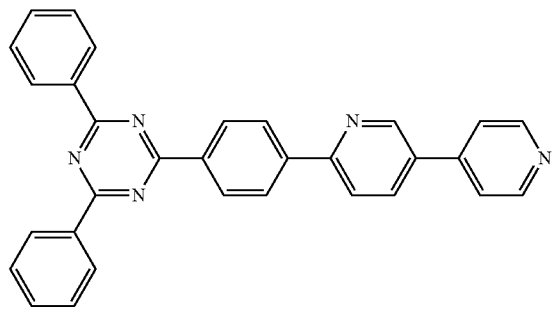
ET_04
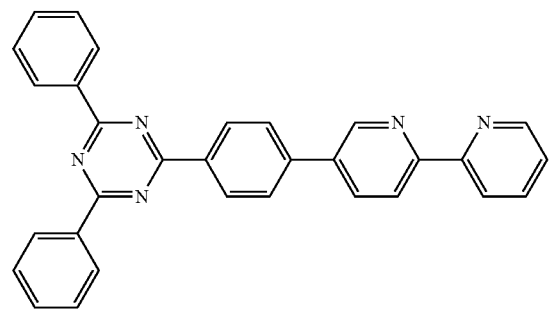
ET_05
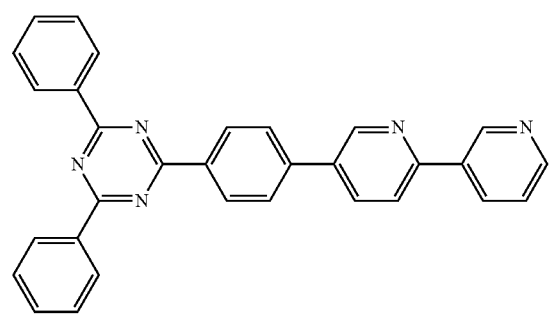
ET_06
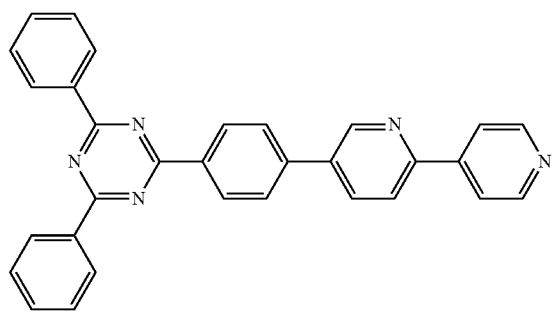
ET_07
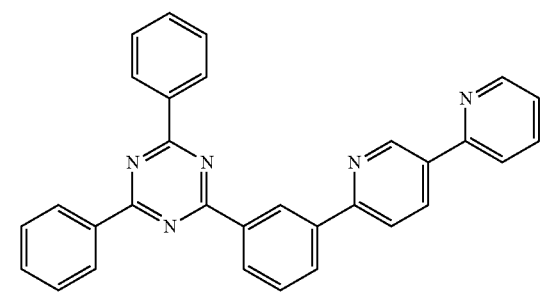
ET_08
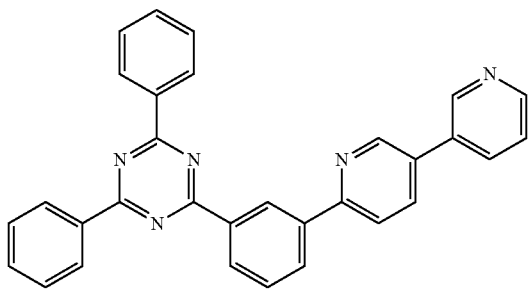
ET_09
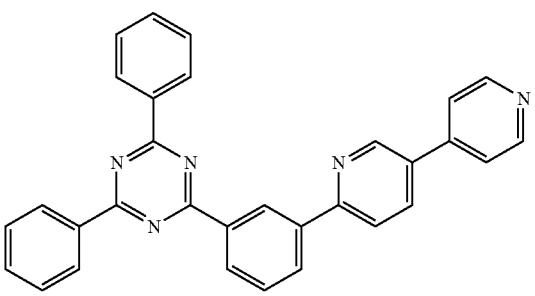
ET_10
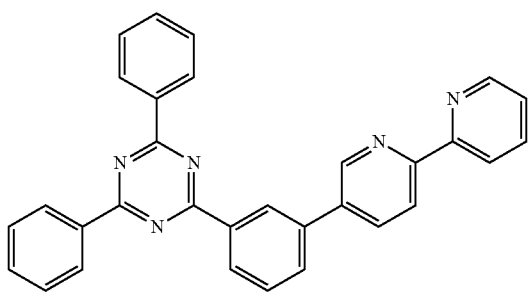
ET_11
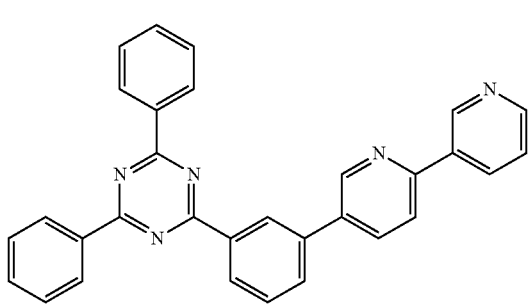
ET_12
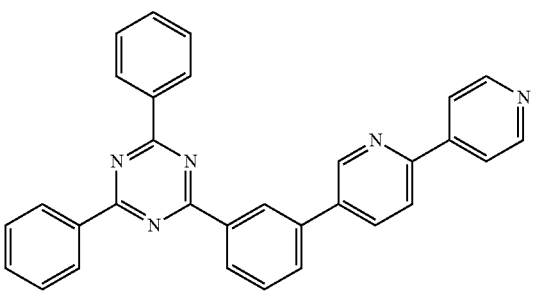

-continued
ET_13
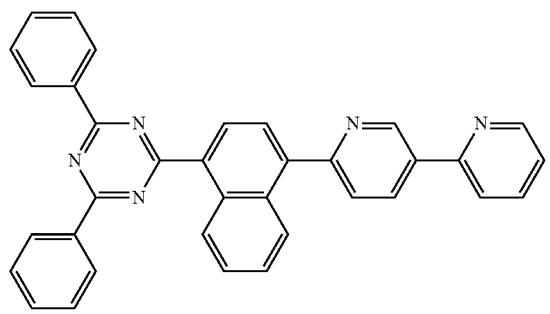
ET_14
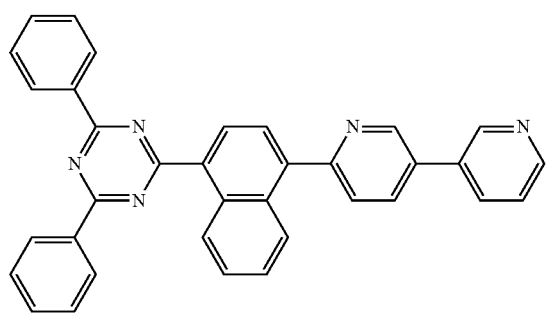
ET_15
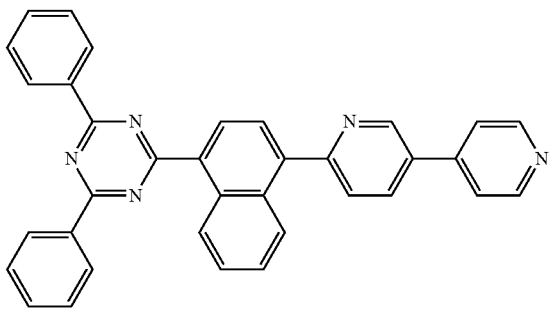
ET_16
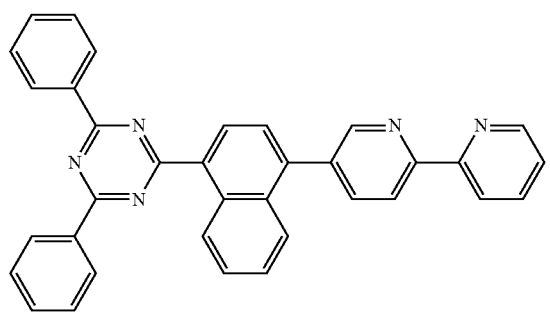
ET_17
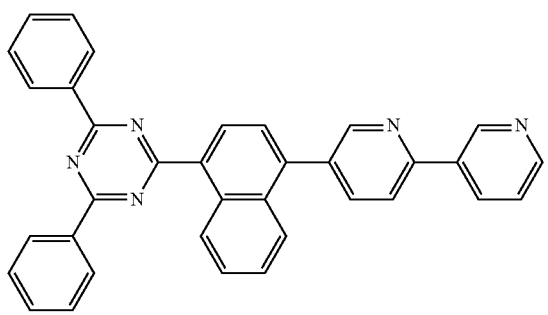
ET_18
ET_19
ET_20

ET_21
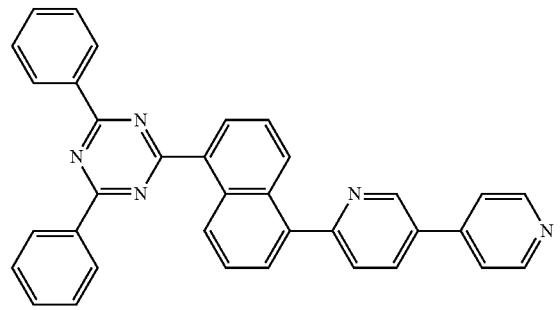
ET_22
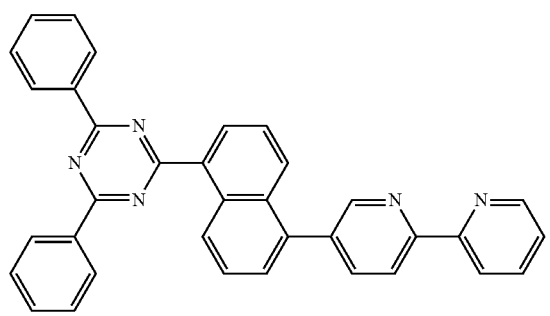
ET_23
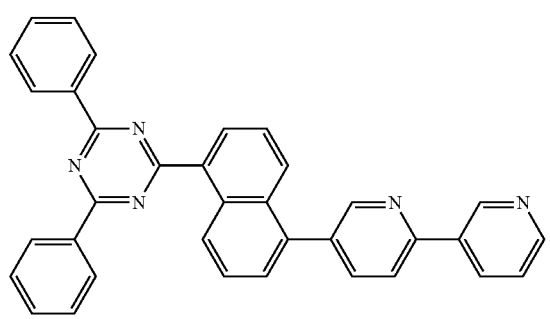
ET_24
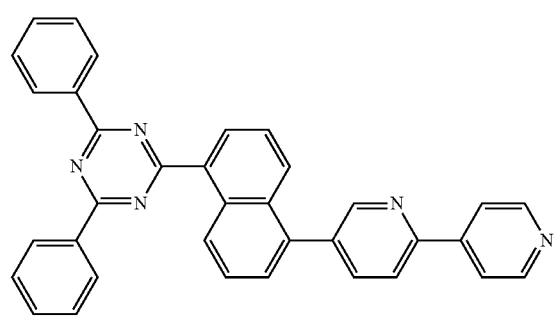
ET_25
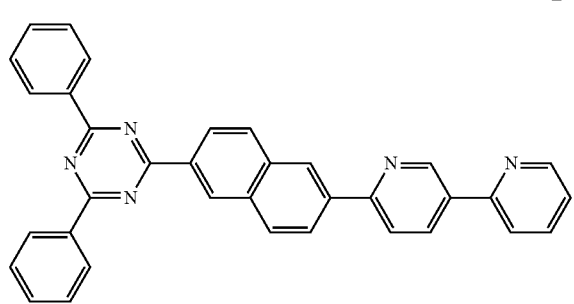
ET_26
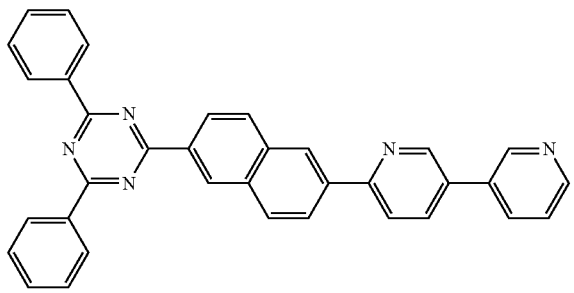
ET_27
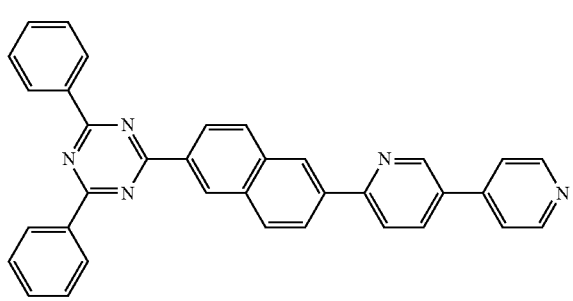
ET_28
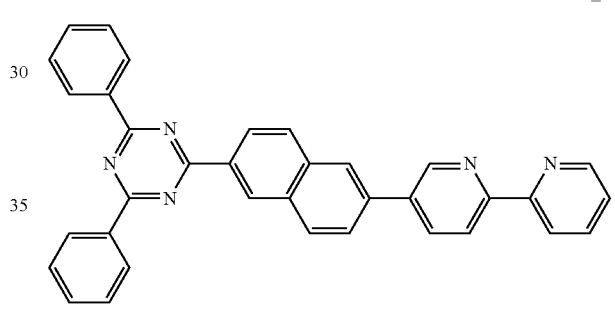
ET_29
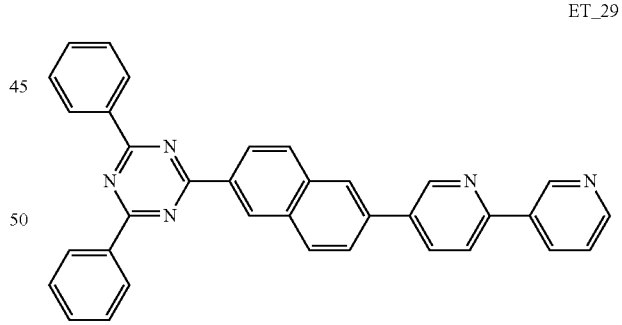
ET_30
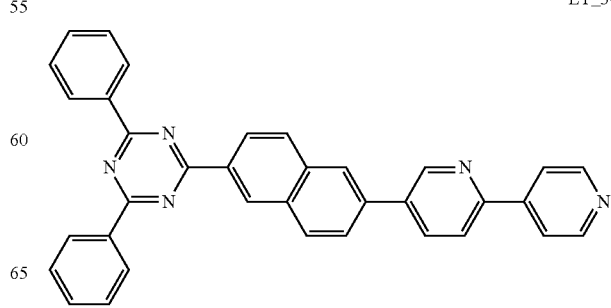

-continued
ET_31
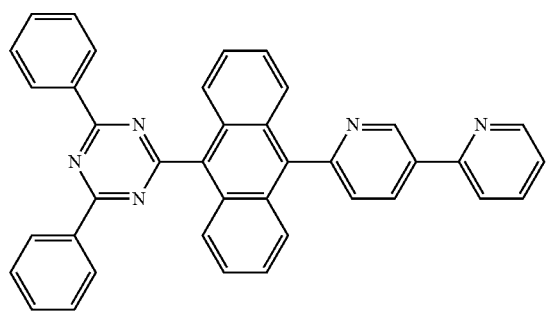
ET_32
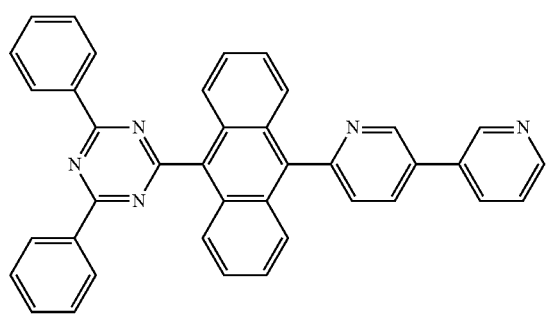
ET_33
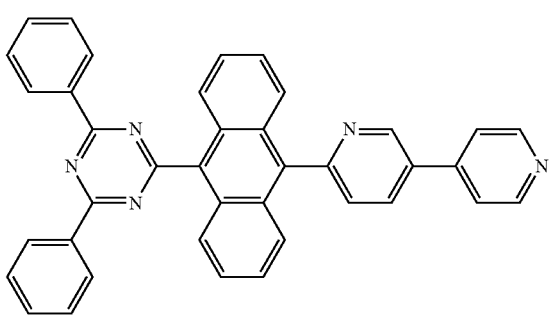
ET_34
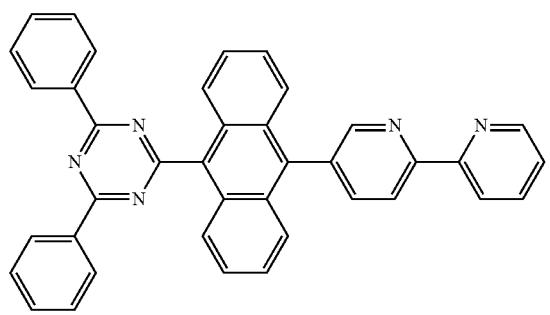
-continued
ET_35
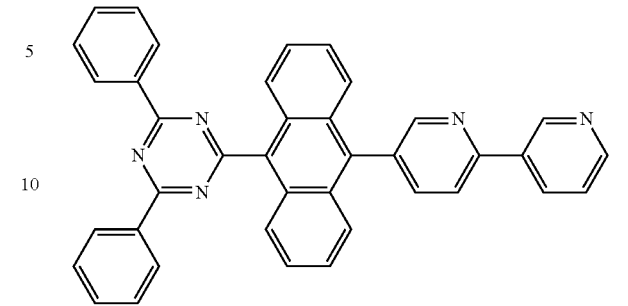
ET_36
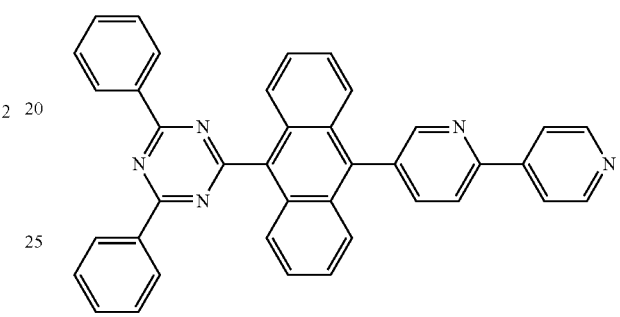
ET_37
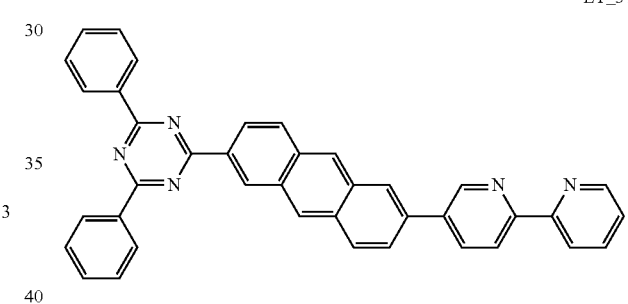
ET_38
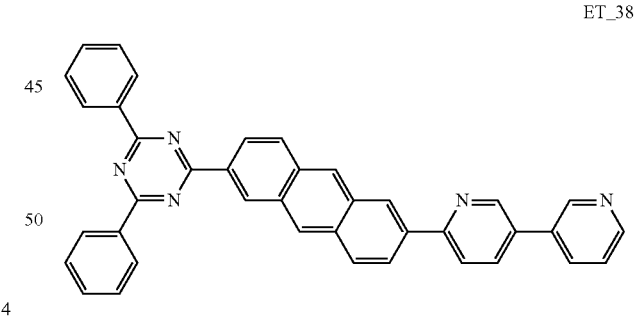
ET_39
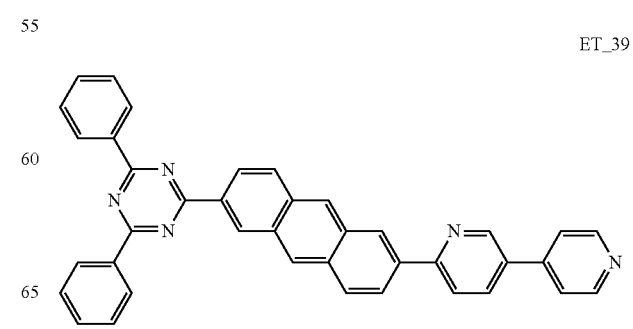

-continued
ET_40
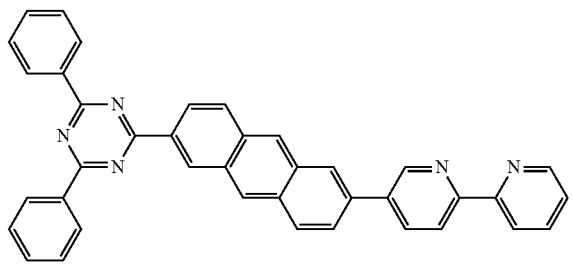
ET_41
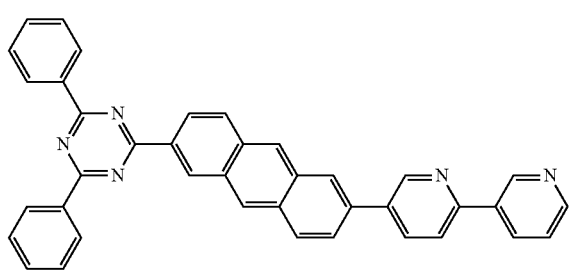
ET_42
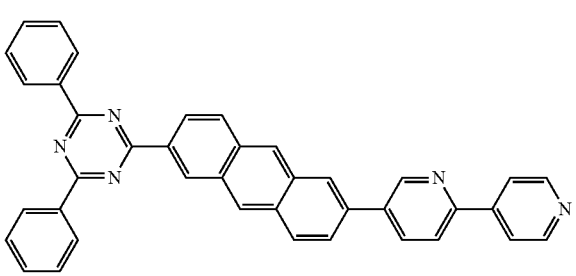
ET_43
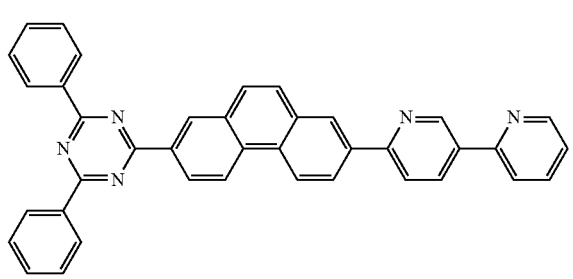
ET_44
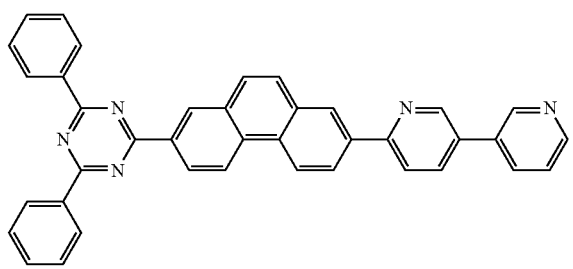
-continued
ET_45
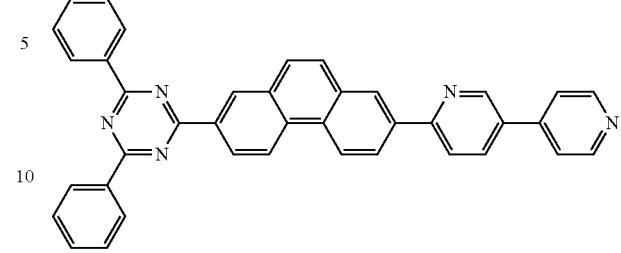
ET_46
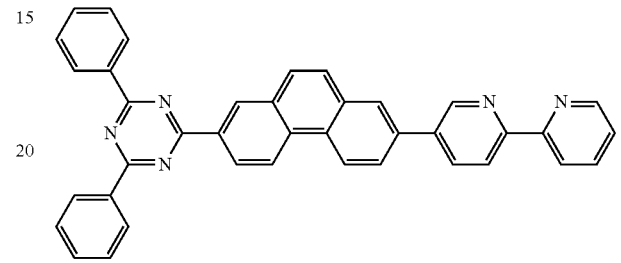
ET_47
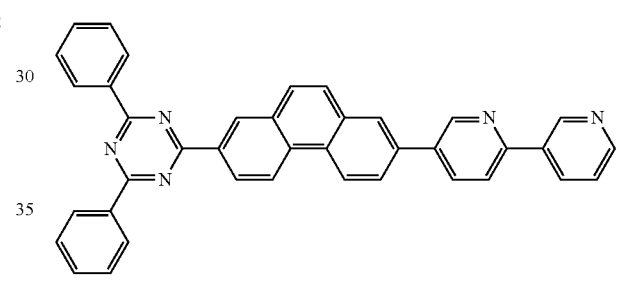
ET_48
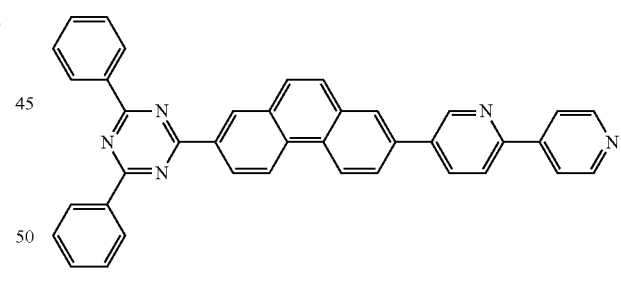
ET_49
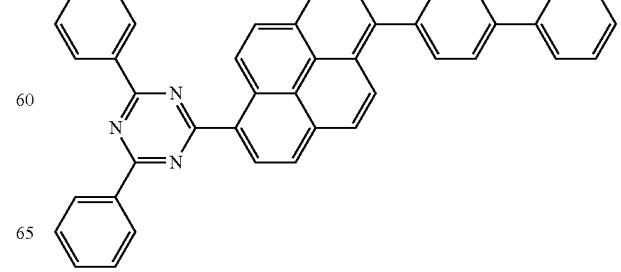

-continued
ET_50
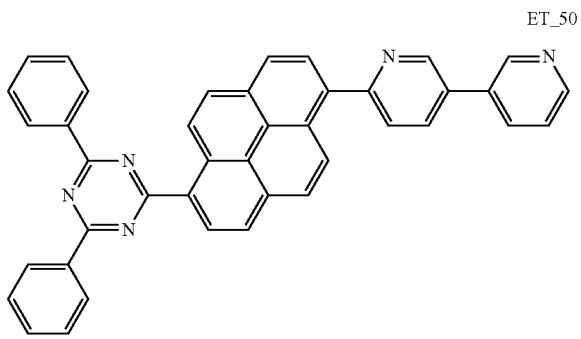
ET_51
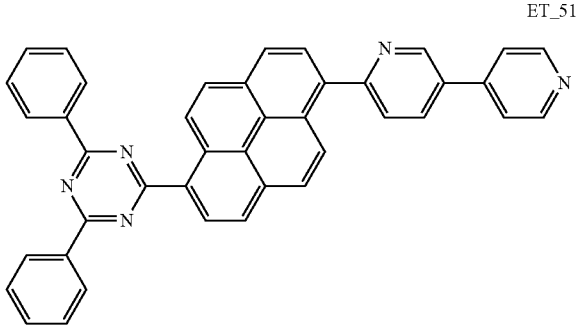
ET_52
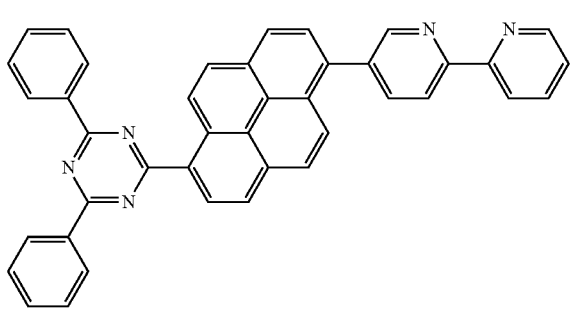
ET_53
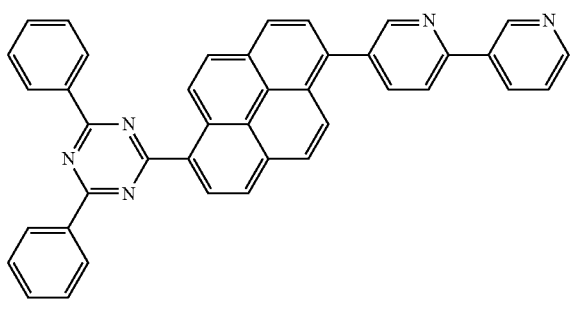
ET_54
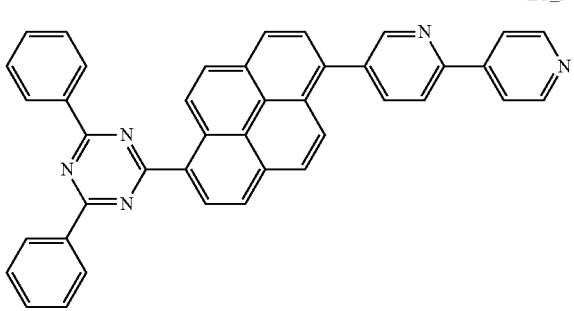
-continued
ET_55
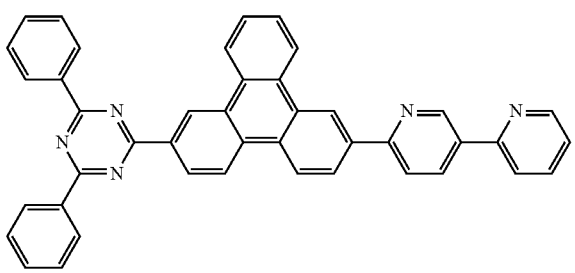
ET_56
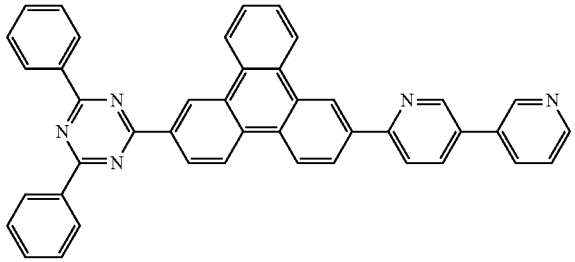
ET_57
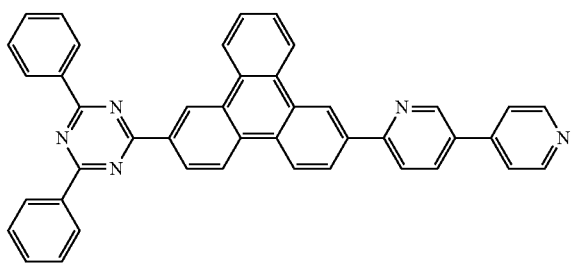
ET_58
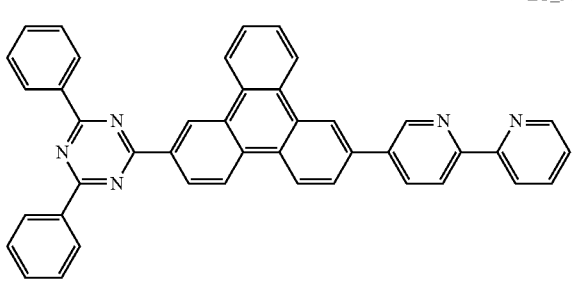
ET_59
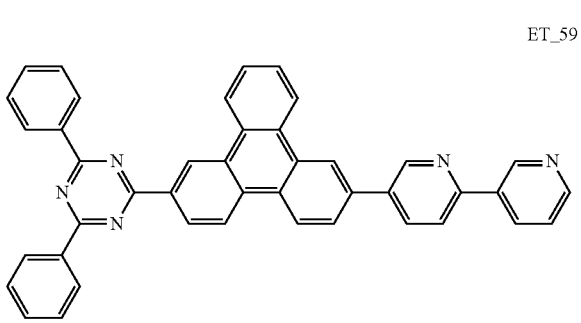

ET_60
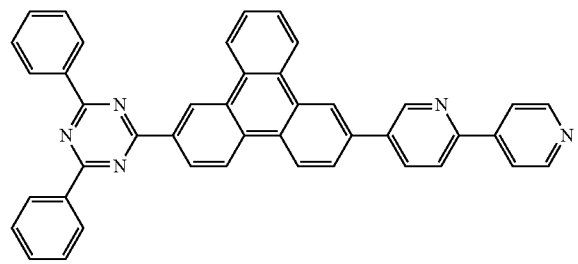
ET_61
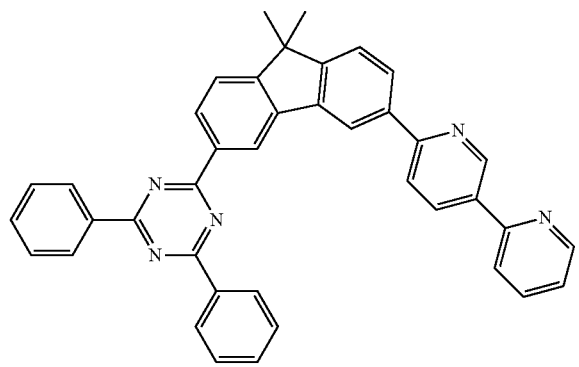
ET_62
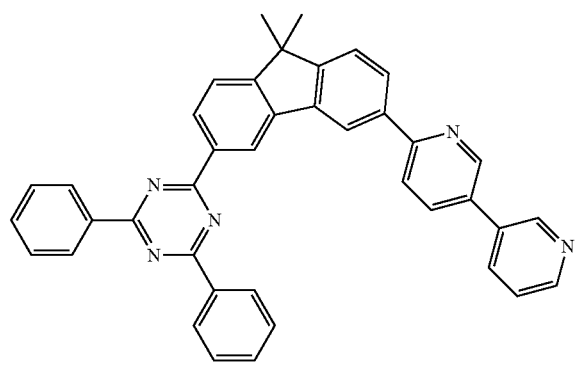
ET_63
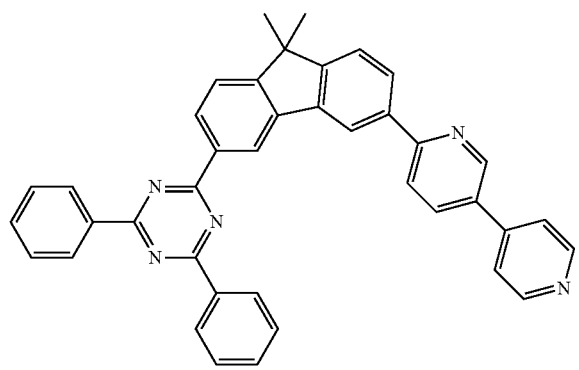
ET_64
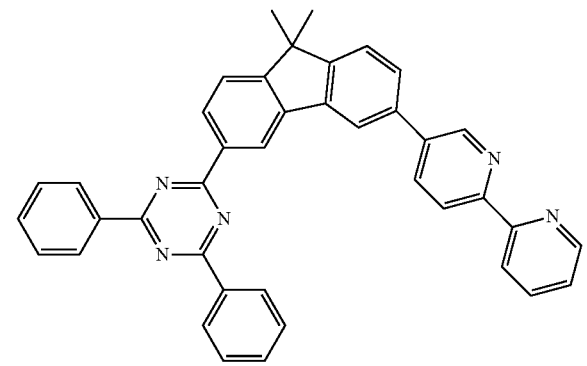
ET_65
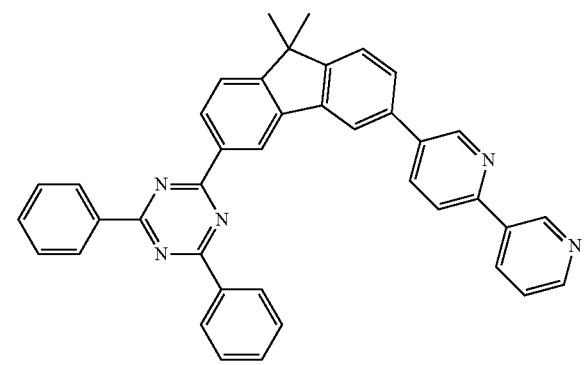
ET_66
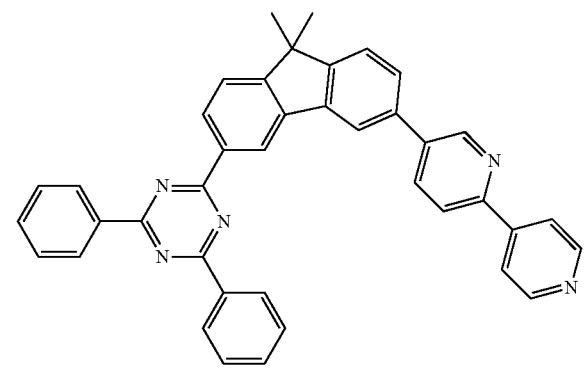
ET_67
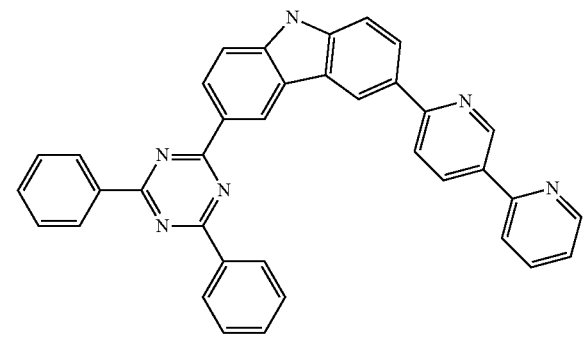

ET_68
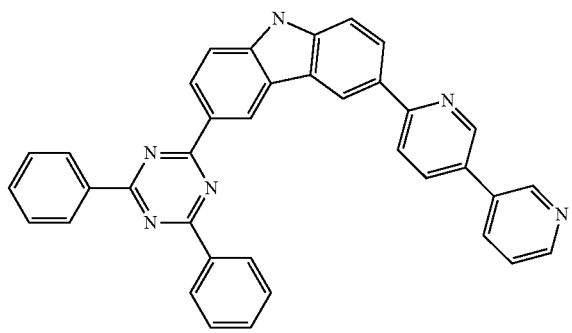
ET_69
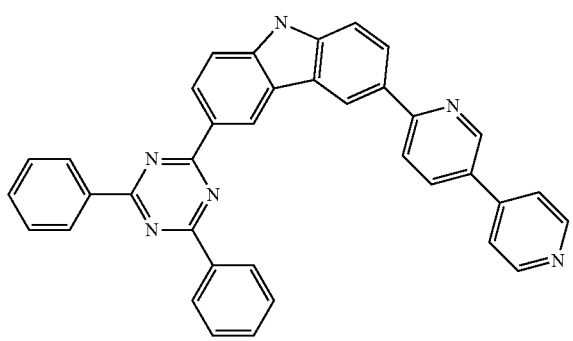
ET_70
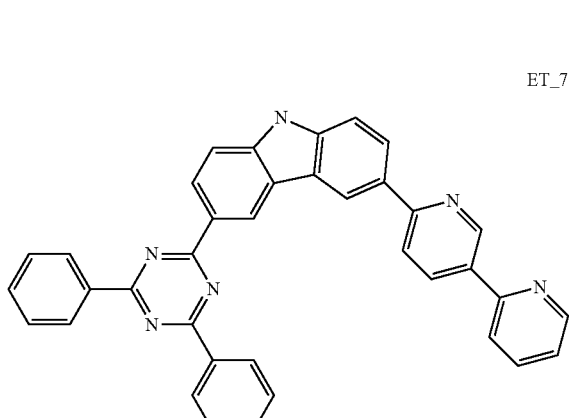
ET_71
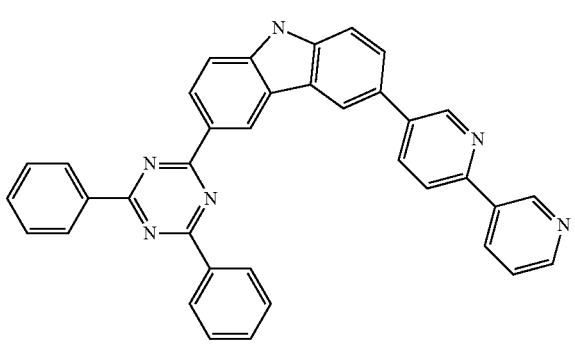
ET_72
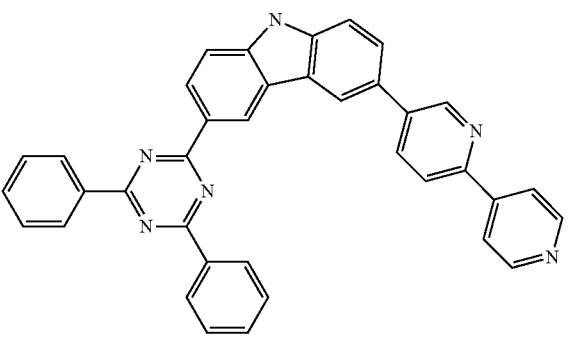
ET_73
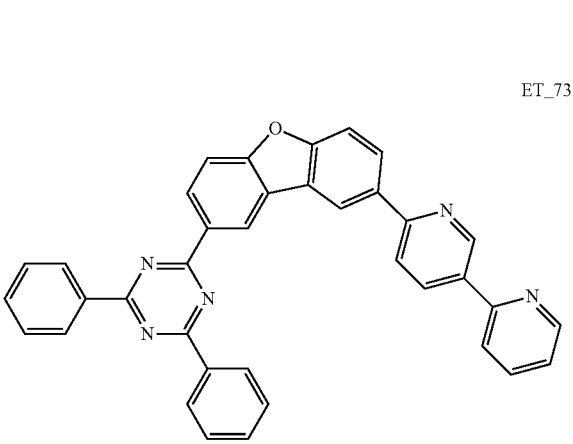
ET_74
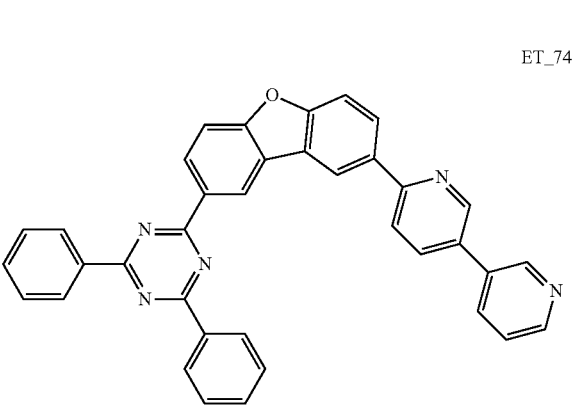
ET_75
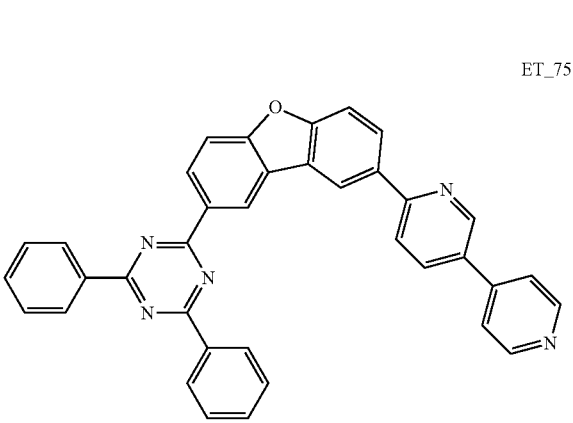

ET_76
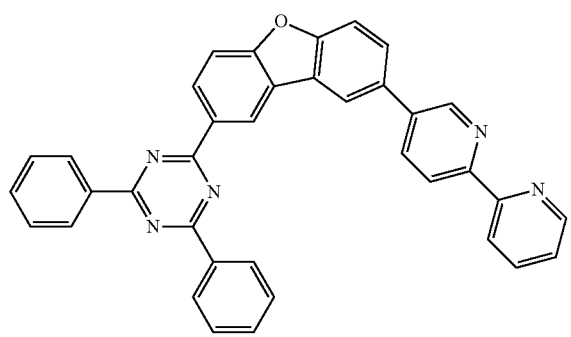
ET_77
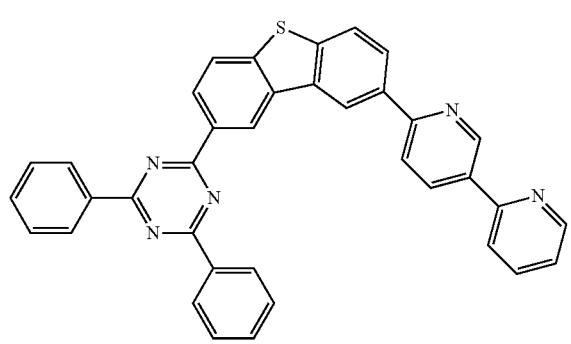
ET_78
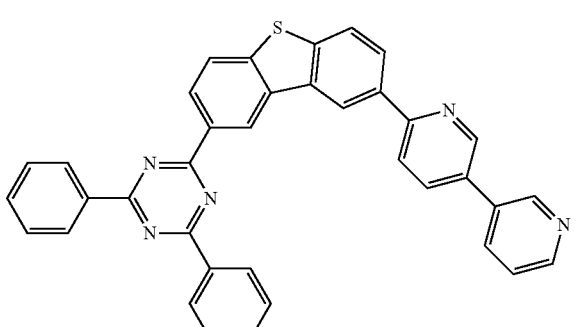
ET_79
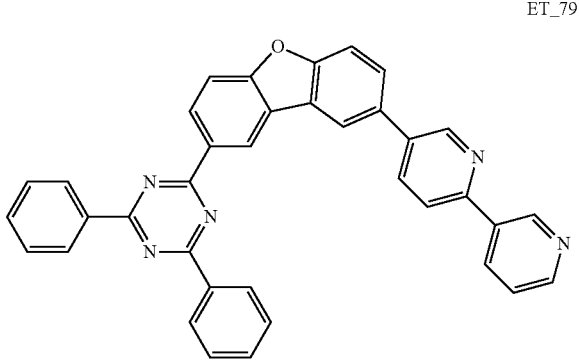
ET_80
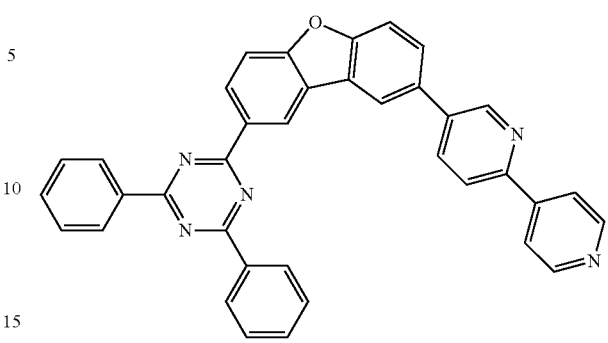
ET_81
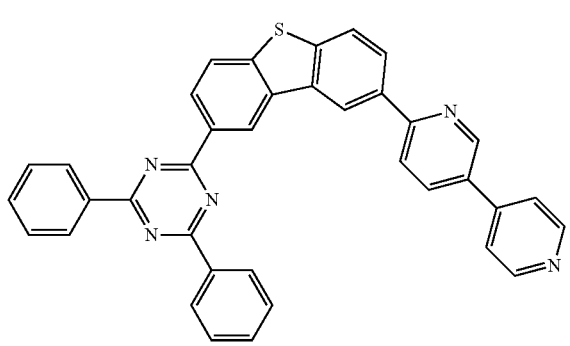
ET_82
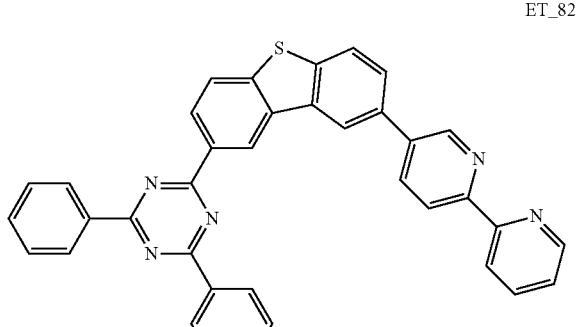
ET_83
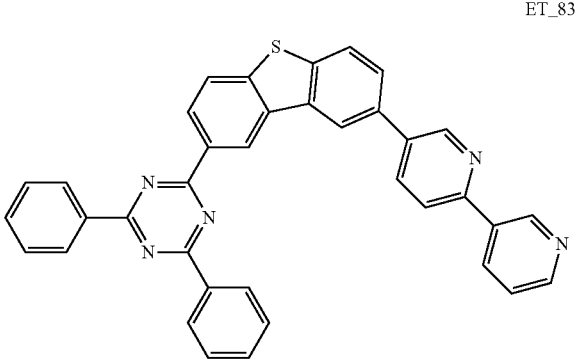

ET_84
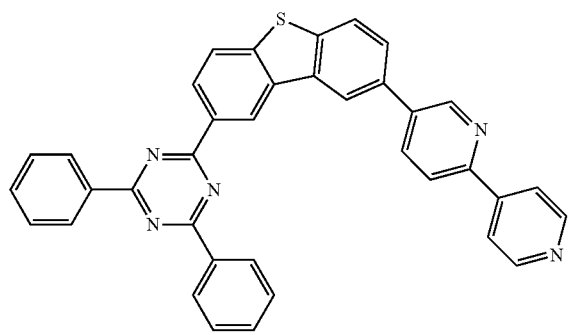
ET_85
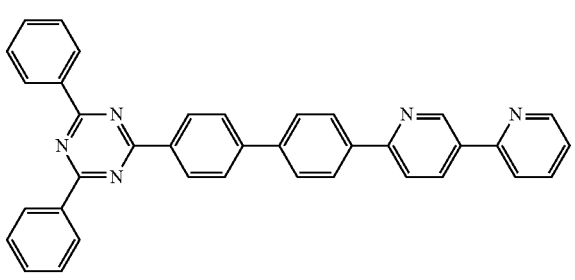
ET_86
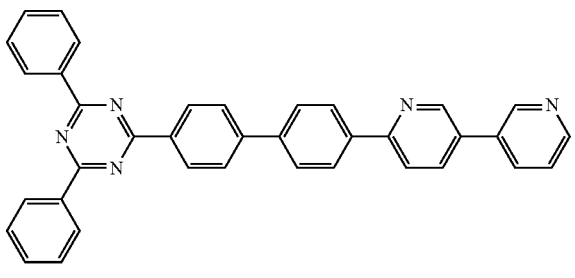
ET_87
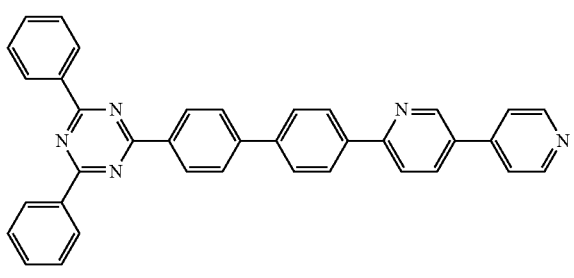
ET_88
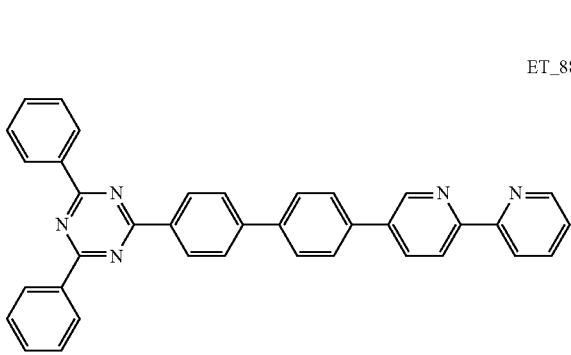
ET_89
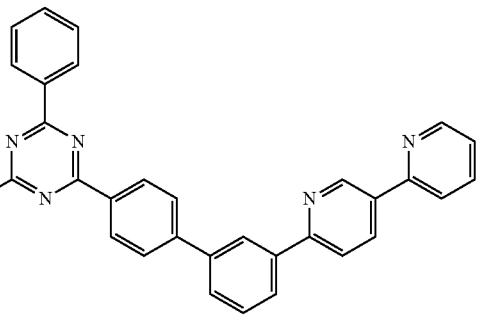
ET_90
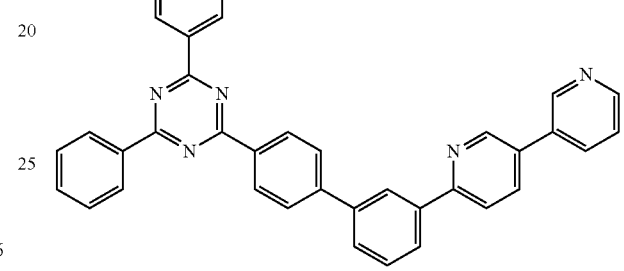
ET_91
ET_92
ET_93
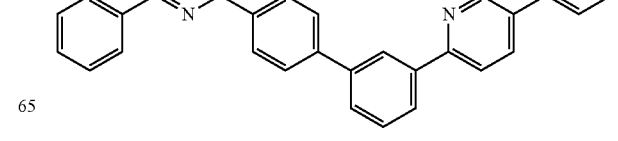

ET_94
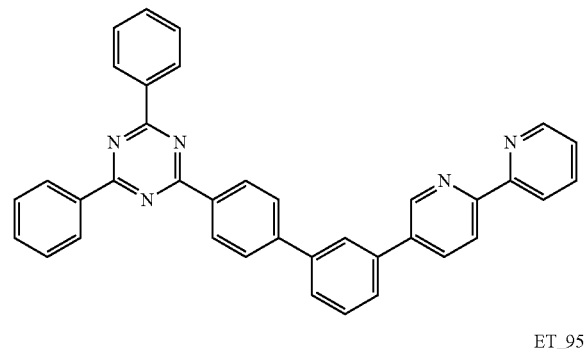
ET_95
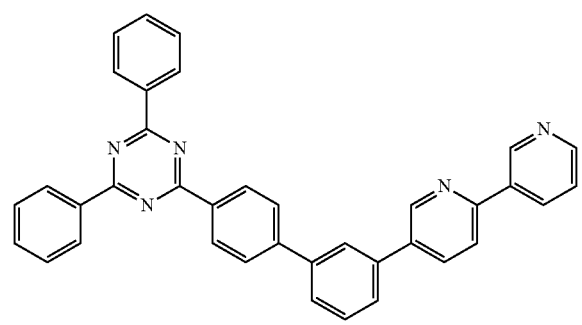
ET_96
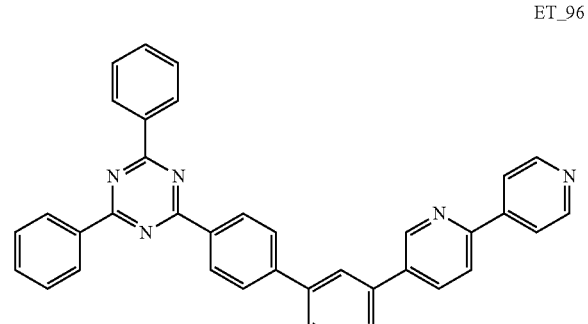
ET_97
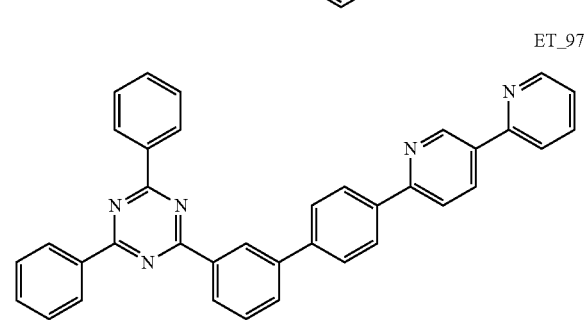
ET_98
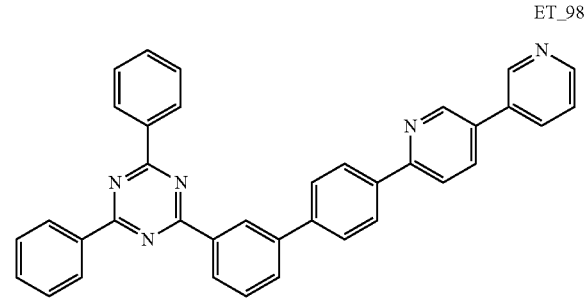
ET_99
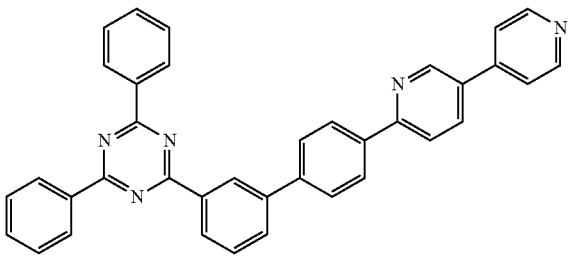
ET_100
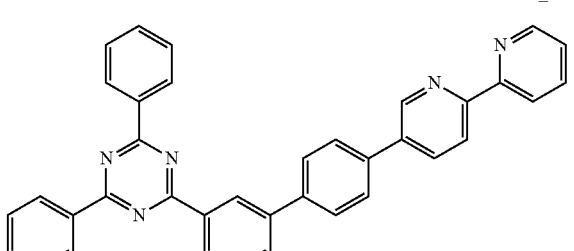
ET_101
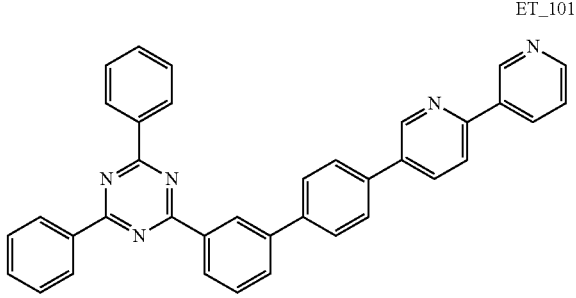
ET_102
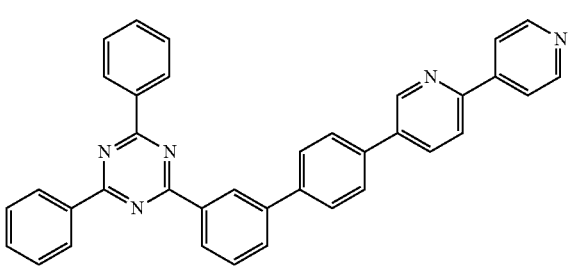
ET_103
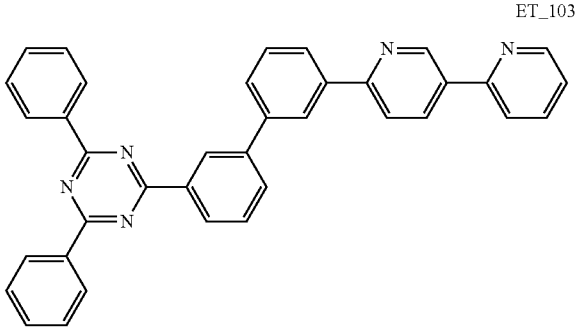

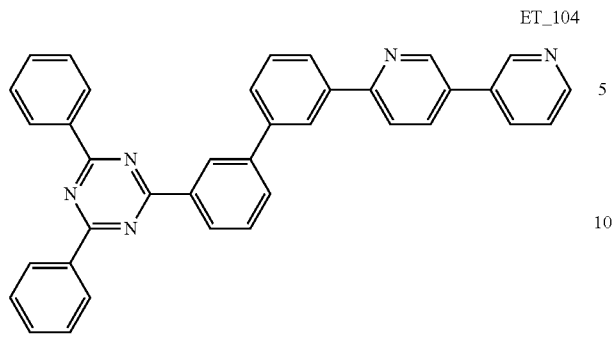
ET_104
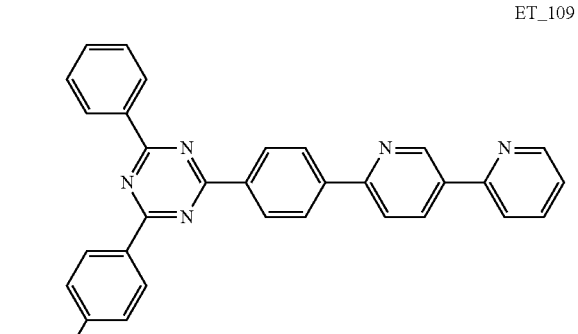
ET_109
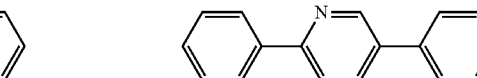
ET_105
ET_110
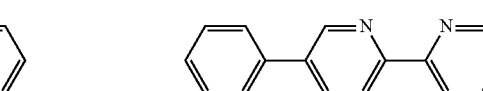
ET_106
ET_107
ET_111
ET_108
ET_112

-continued
ET_113
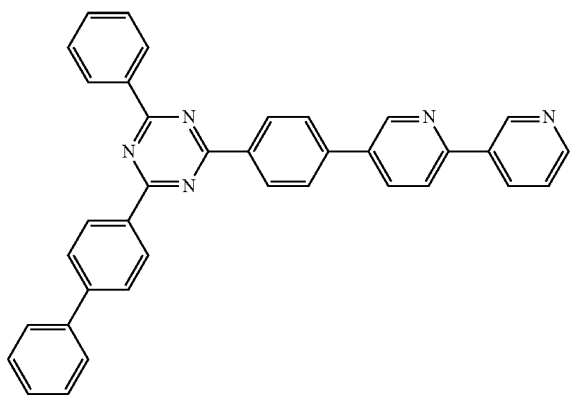
ET_114
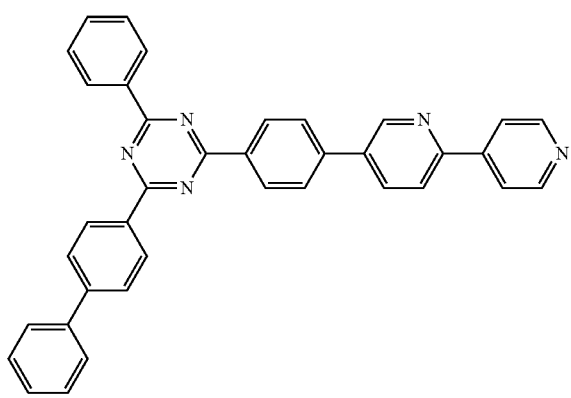
ET_115
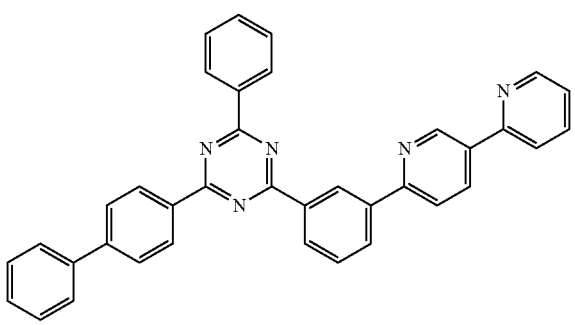
ET_116
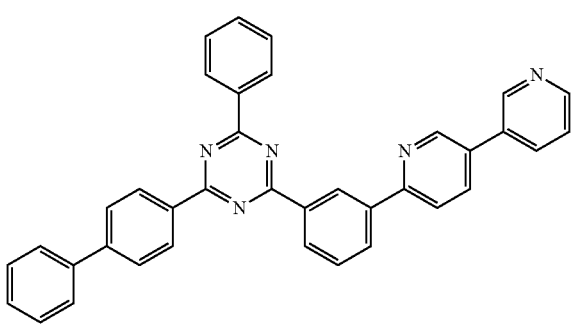
-continued
ET_117
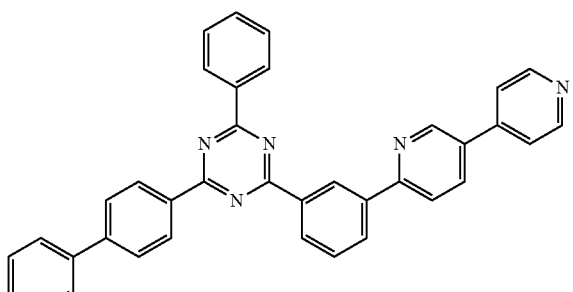
ET_118
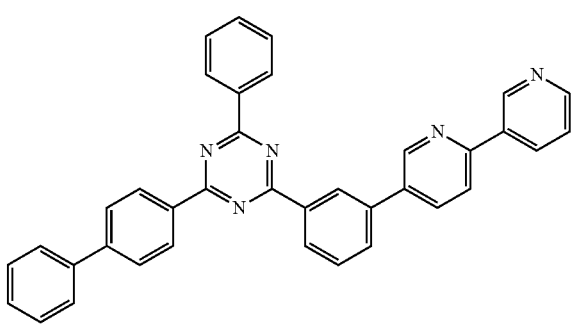
ET_119
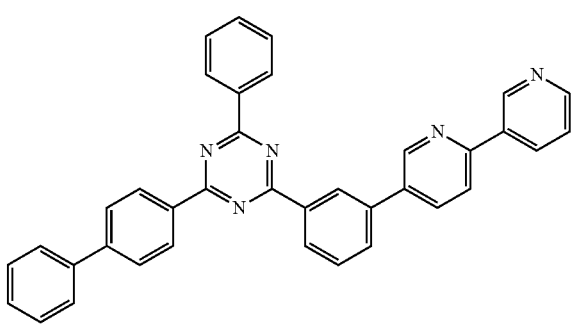
ET_120
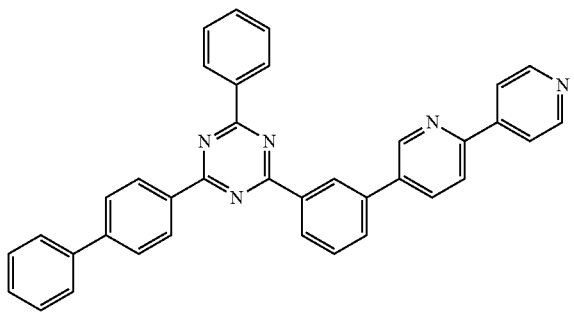

-continued
ET_121
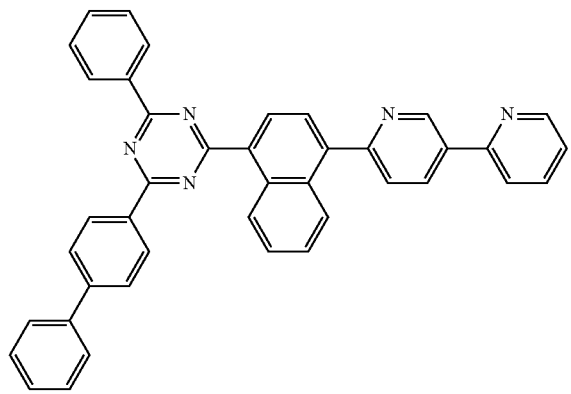
ET_122
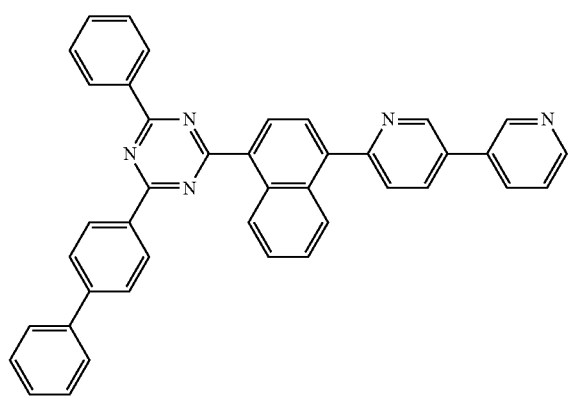
ET_123
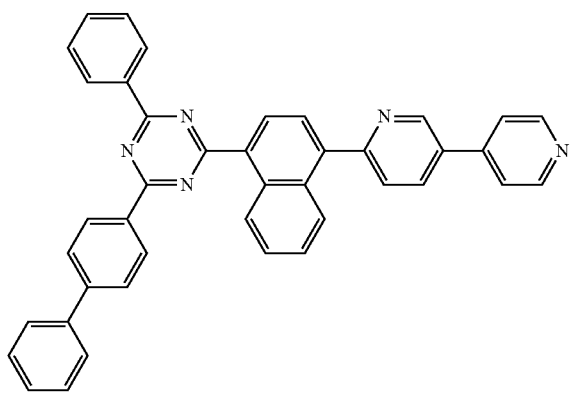
ET_124
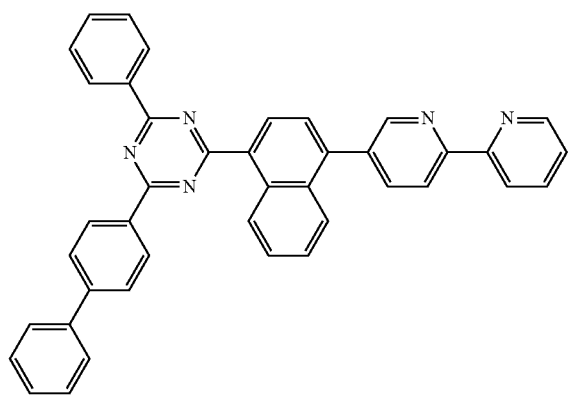
ET_125
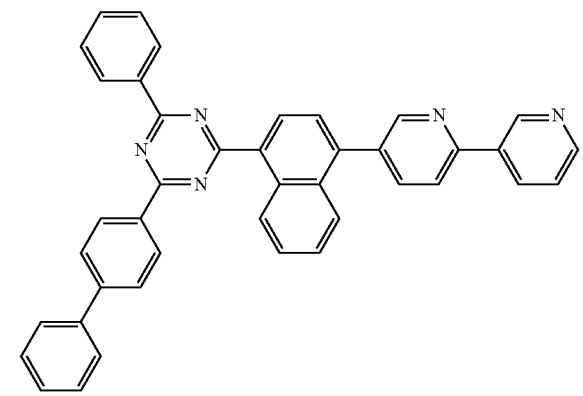
ET_126
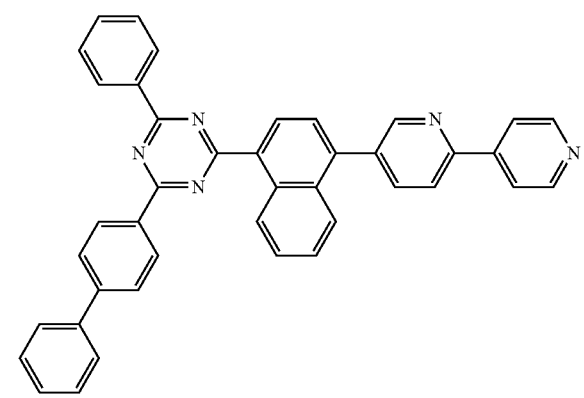
ET_127
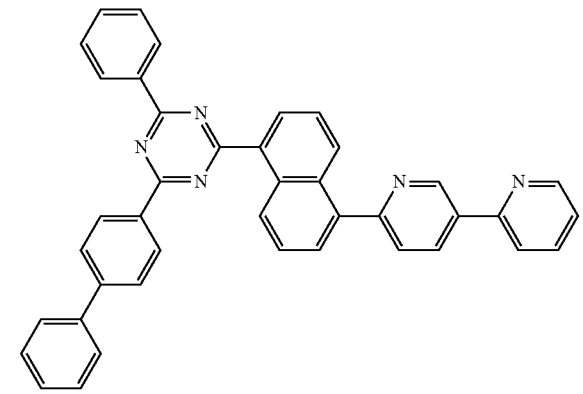
ET_128
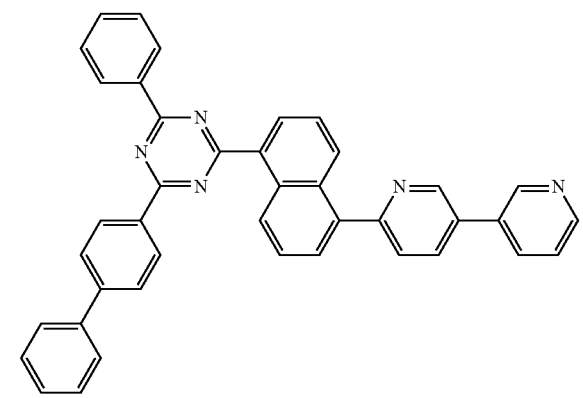

ET_129
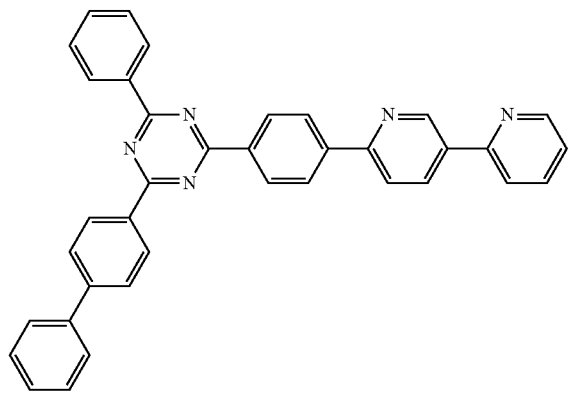
ET_130
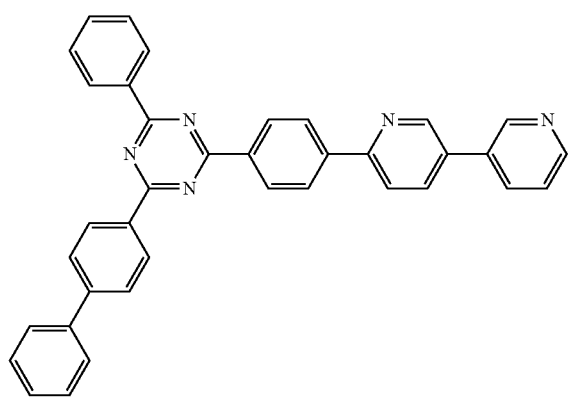
ET_131
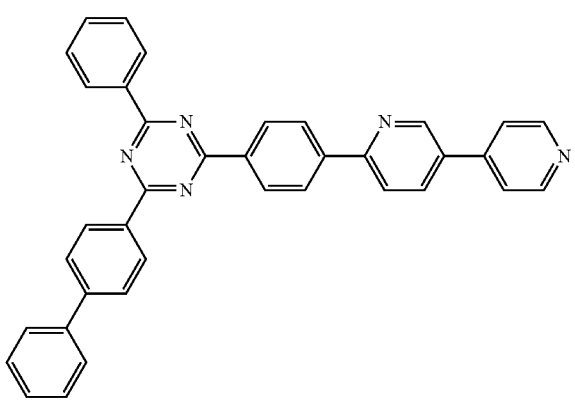
ET_132
ET_133
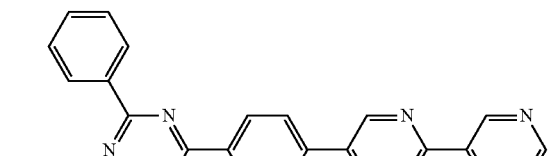
ET_134
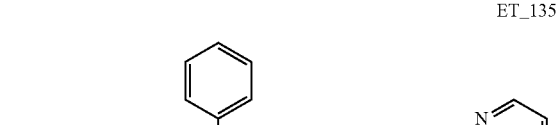
ET_135
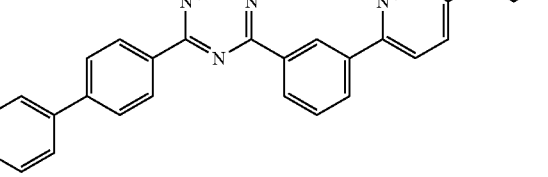
ET_136
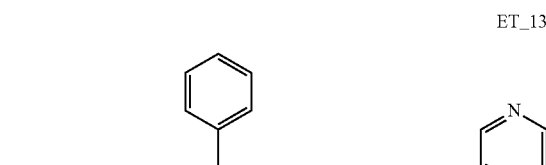
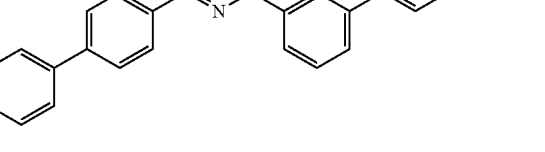

-continued
ET_137
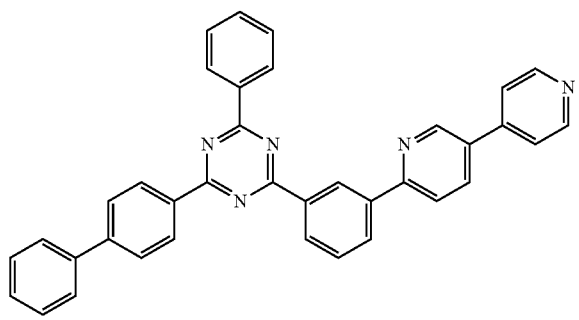
ET_138
ET_139
ET_140
-continued
ET_141
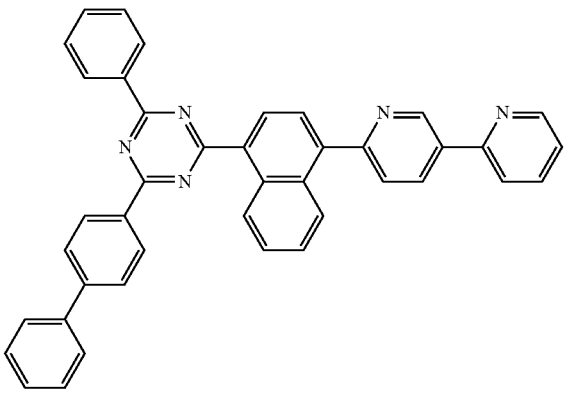
ET_142
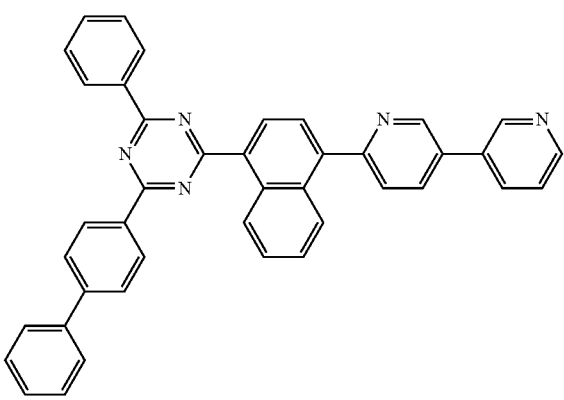
ET_143
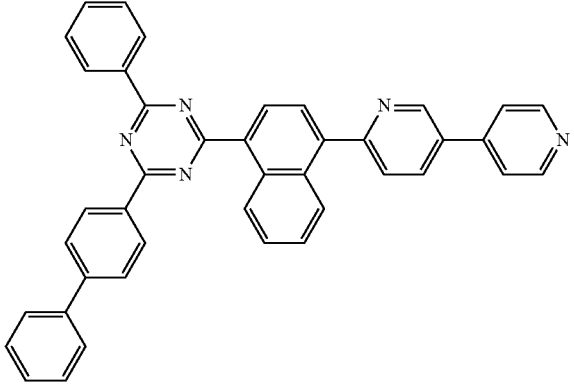
ET_144
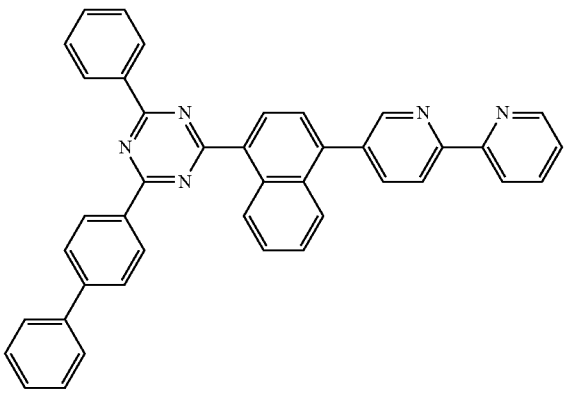

ET_145
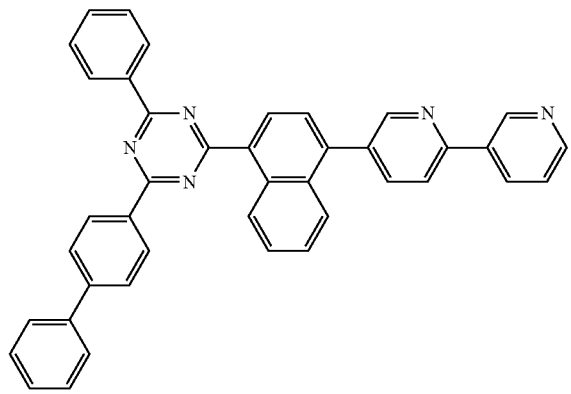
ET_146
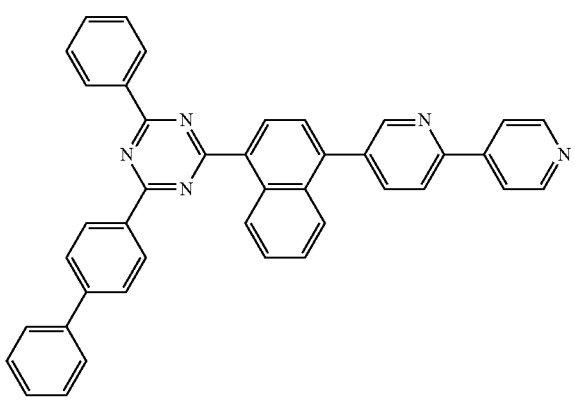
ET_147
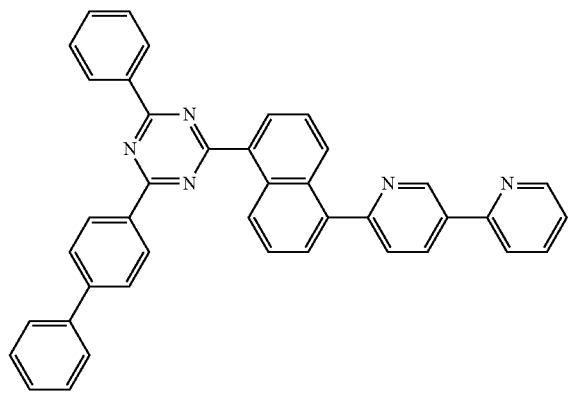
ET_148
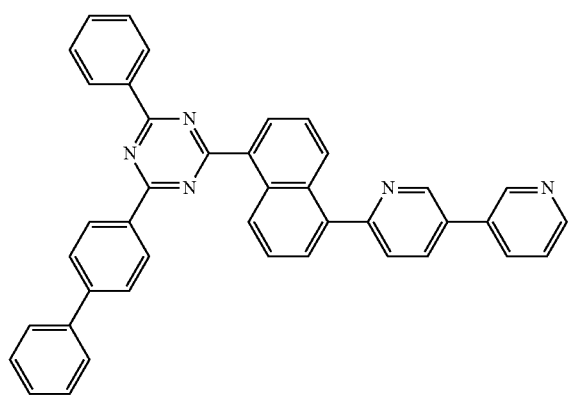
ET_149
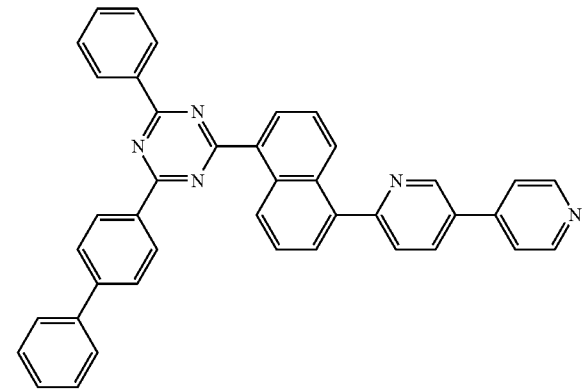
ET_150
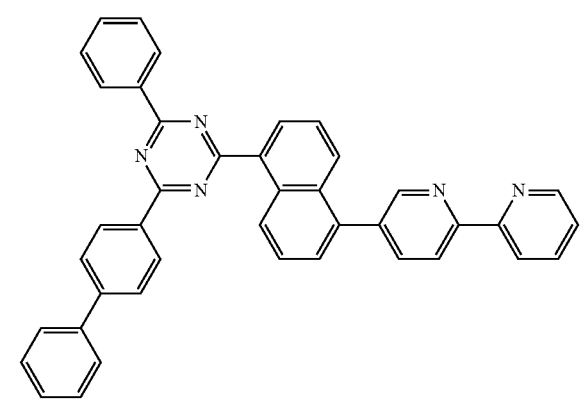
ET_151
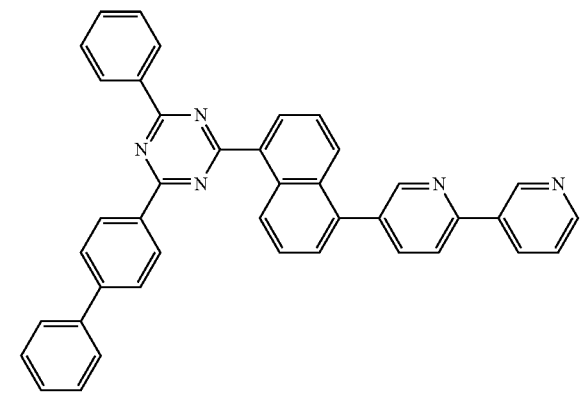
ET_152
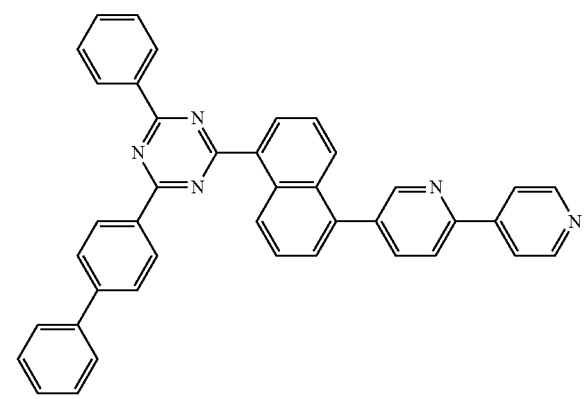

ET_153
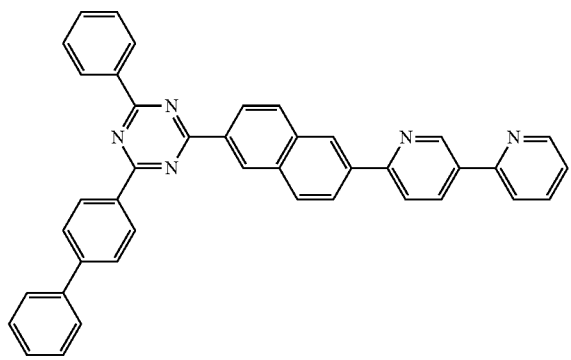
ET_154
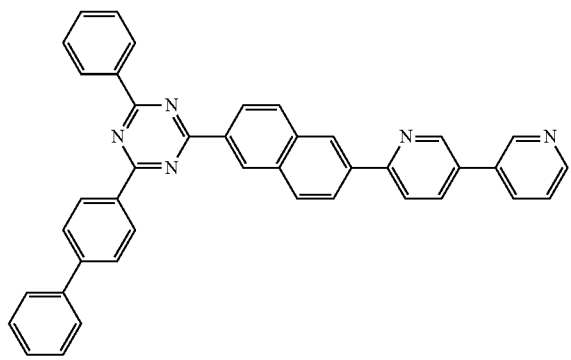
ET_155
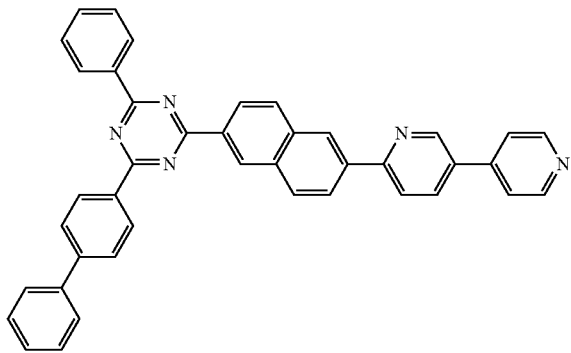
ET_156
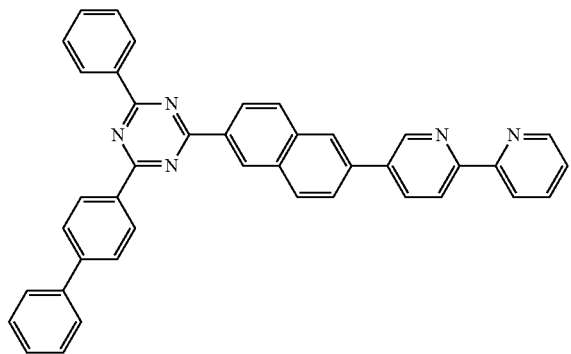
ET_157
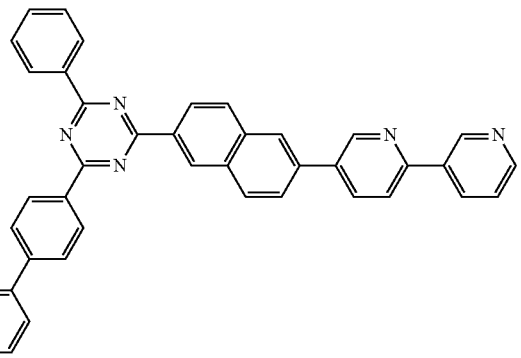
ET_158
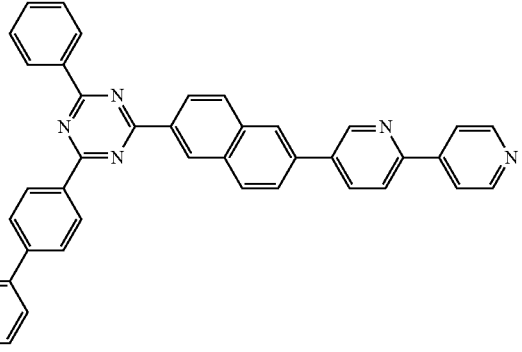
ET_159
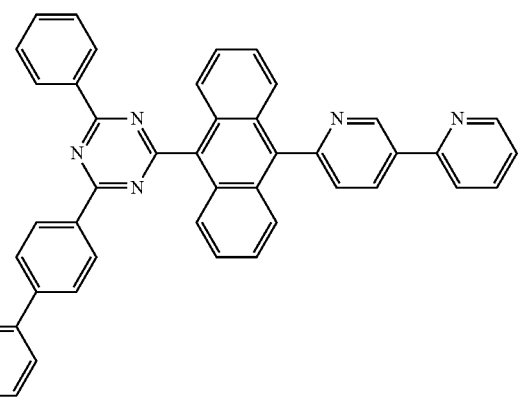
ET_160
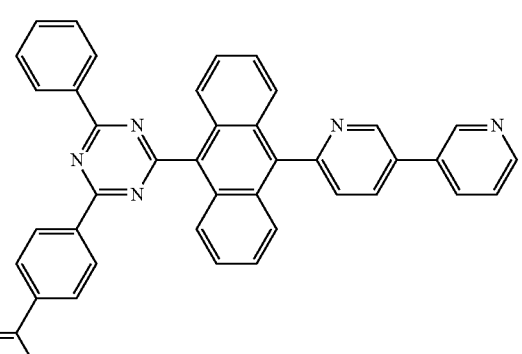

ET_161
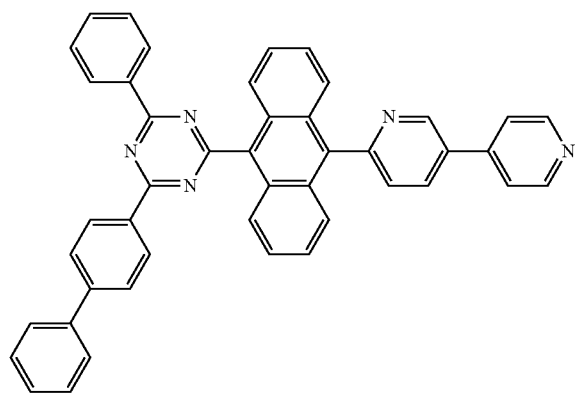
ET_162
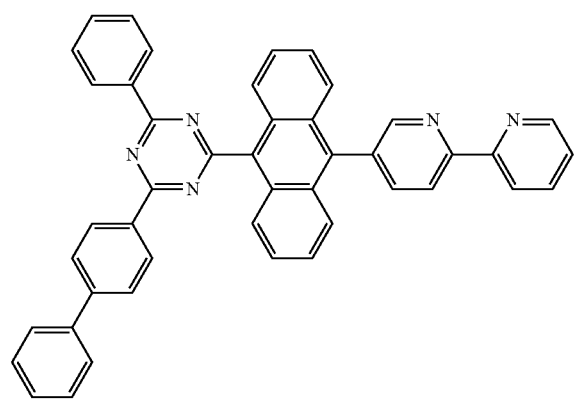
ET_163
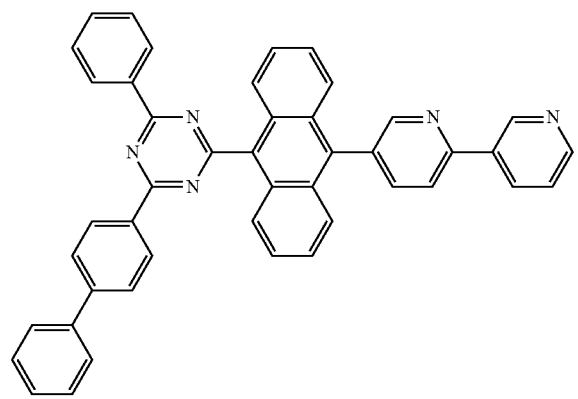
ET_164
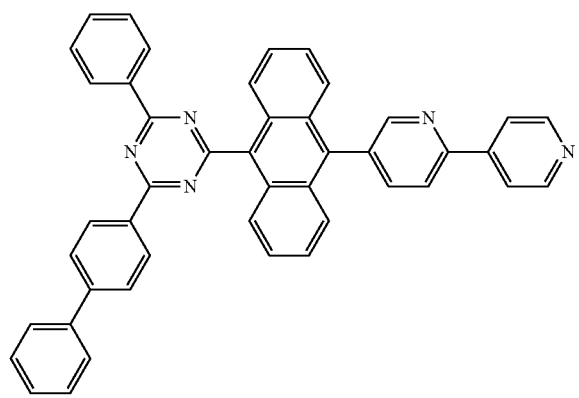
ET_165
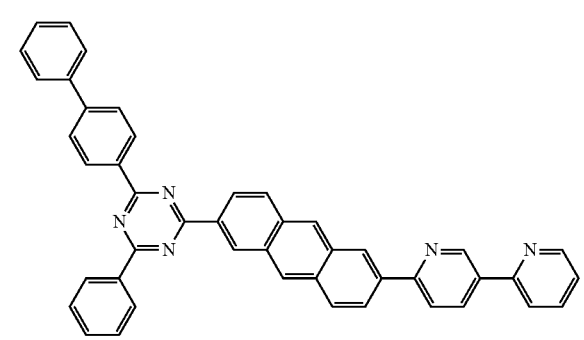
ET_166
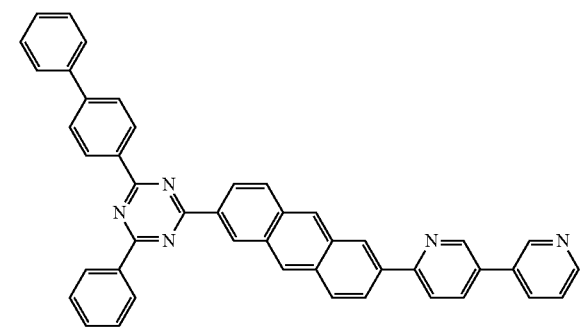
ET_167
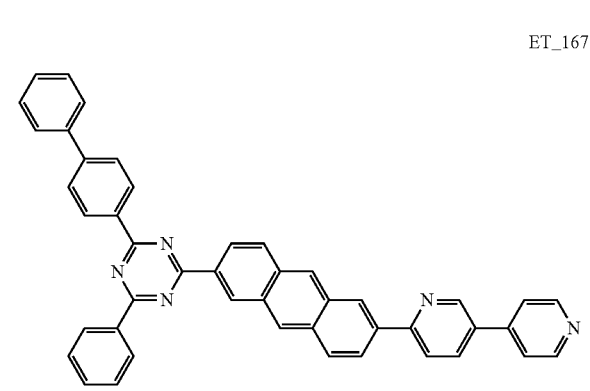
ET_168
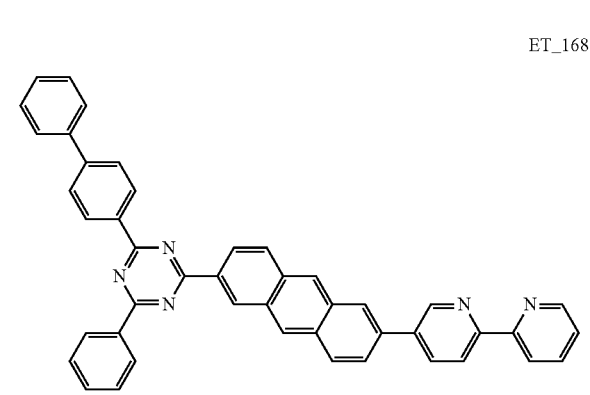

ET_169
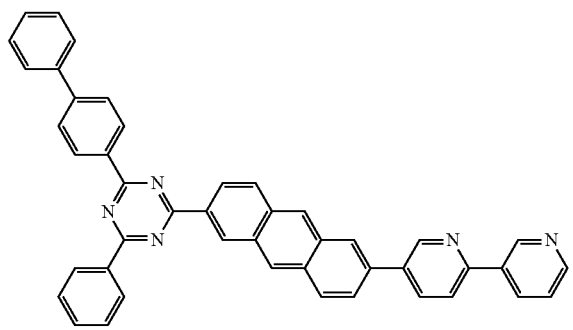
ET_173
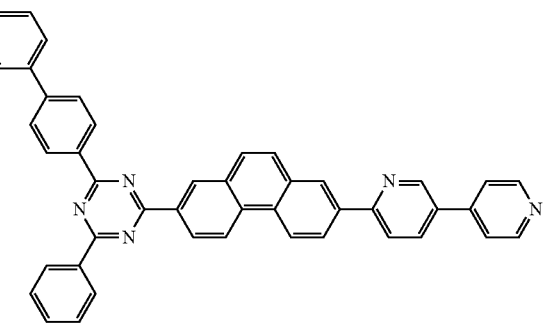
ET_170
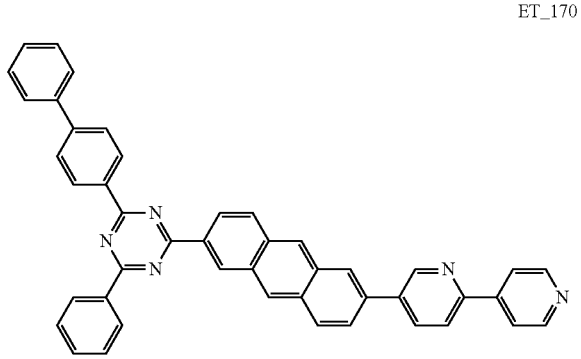
ET_174
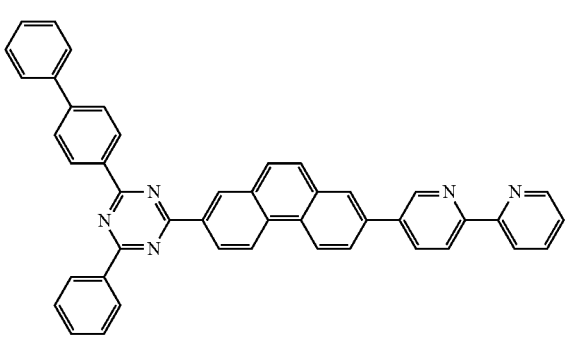
ET_171
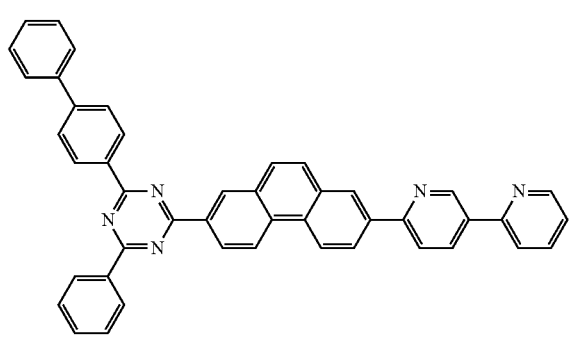
ET_175
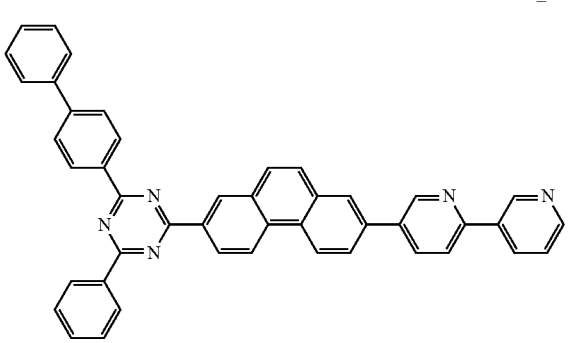
ET_172
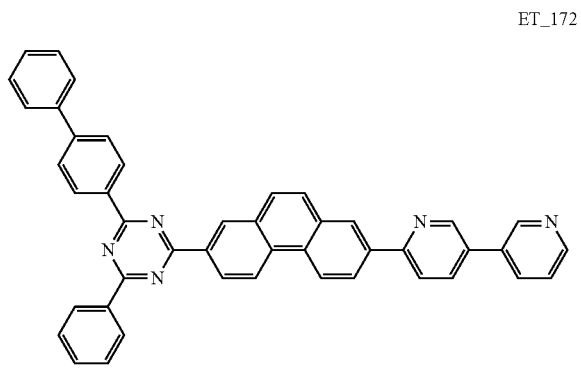
ET_176
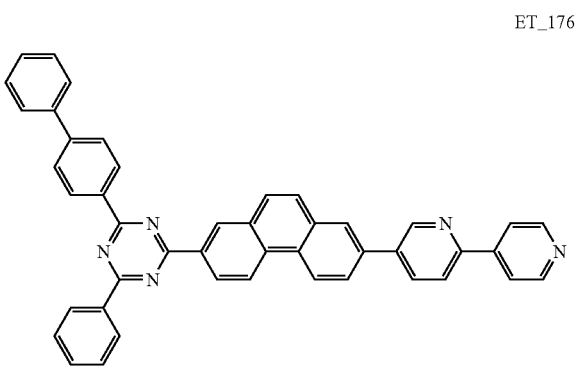

ET_177
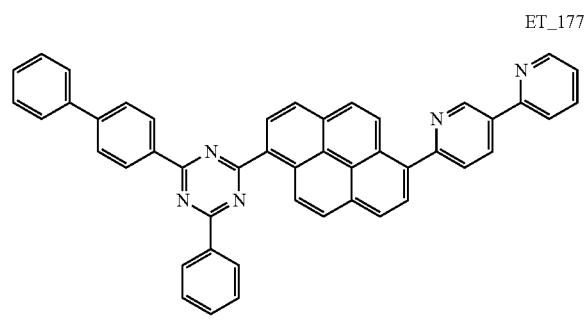
ET_178
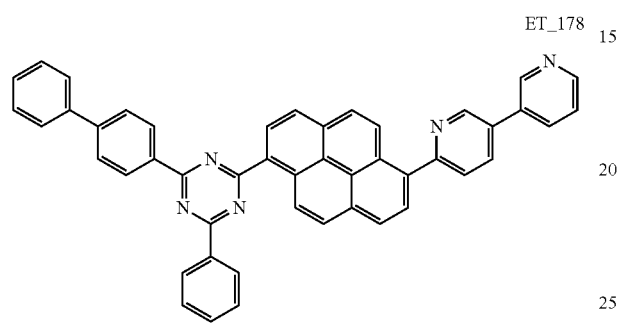
ET_179
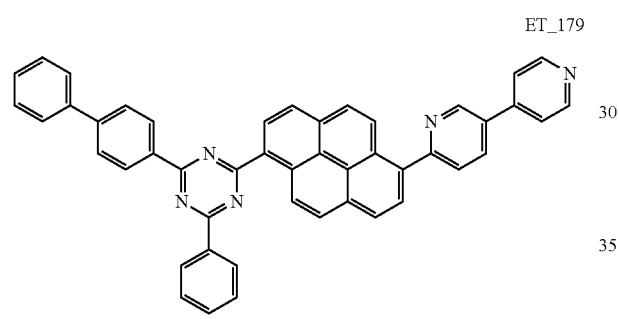
ET_180
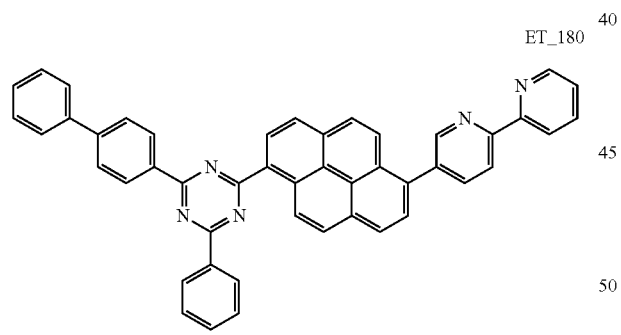
ET_181
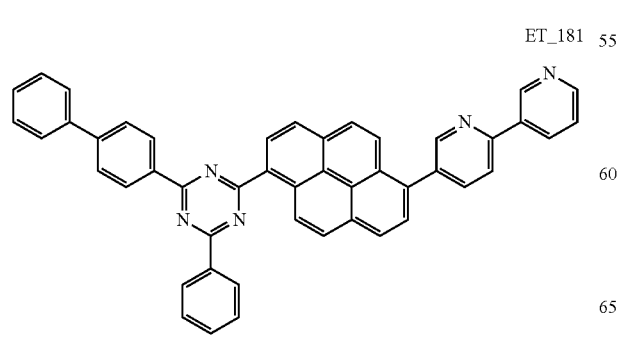
ET_182
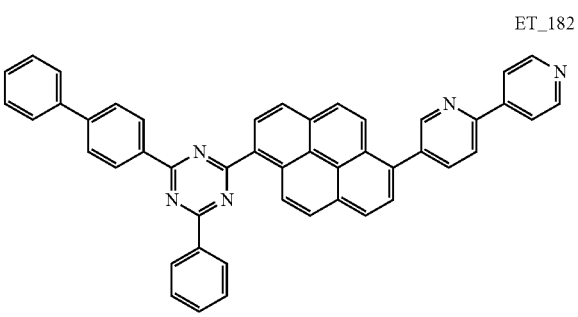
ET_183
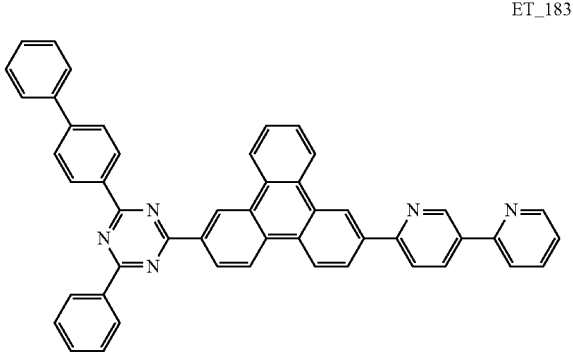
ET_184
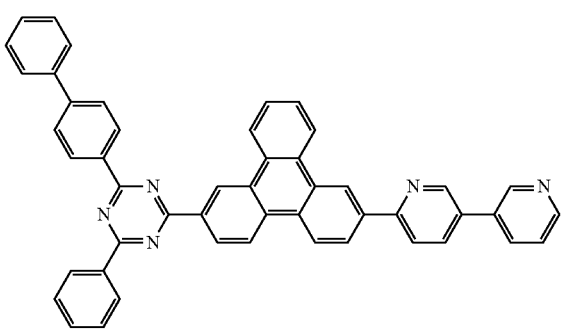
ET_185
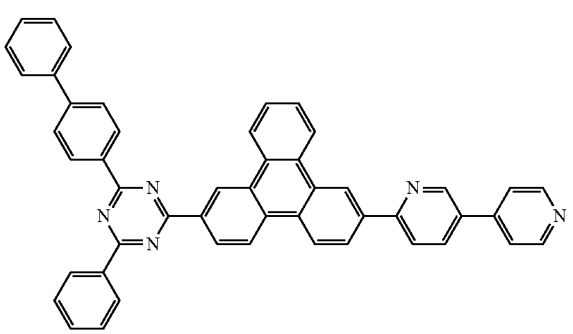

ET_186
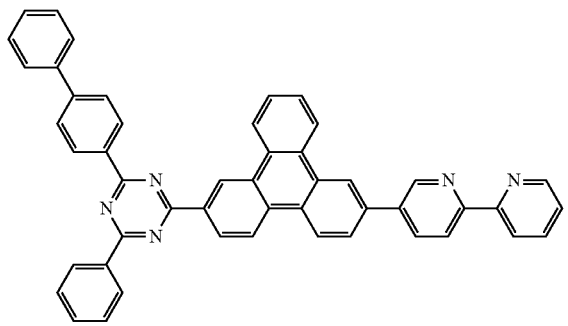
ET_187
ET_188
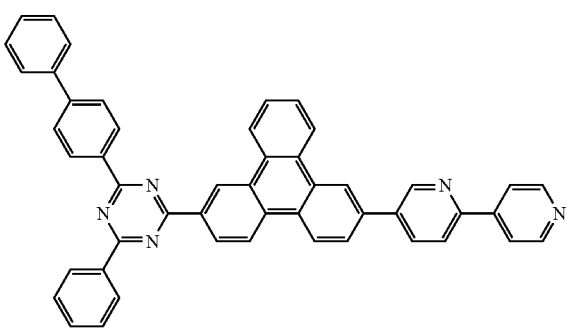
ET_189
ET_190
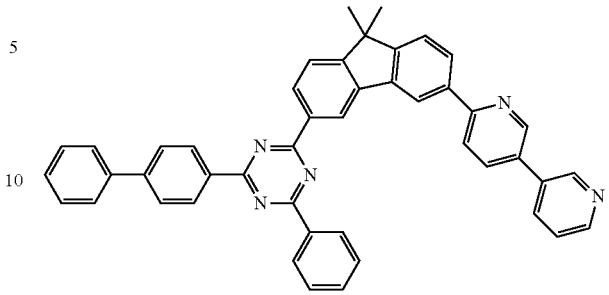
ET_191
ET_192
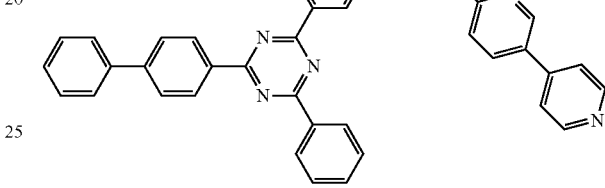
ET_193
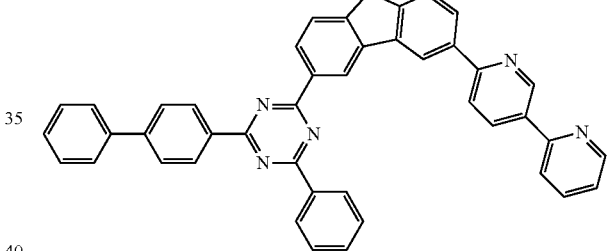
ET_194
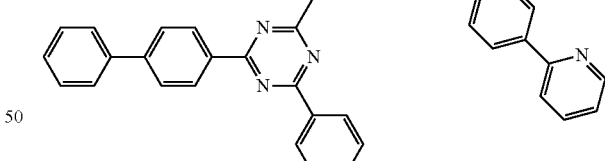
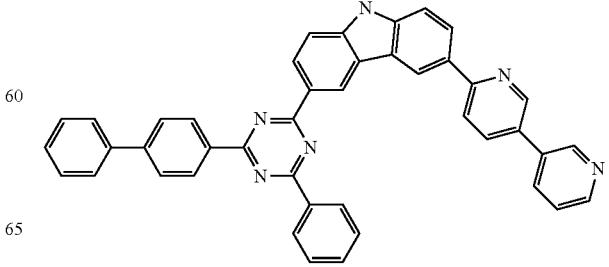

ET_195
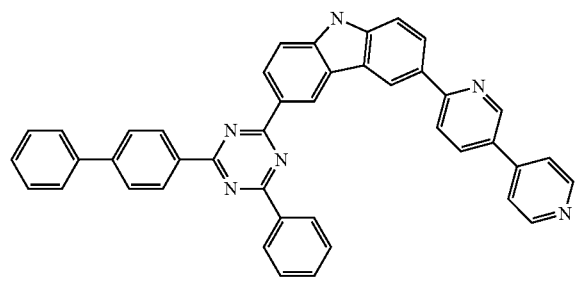
ET_196
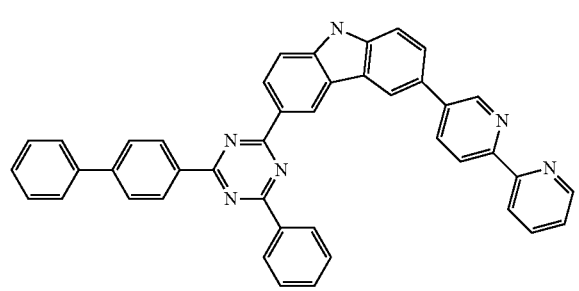
ET_197
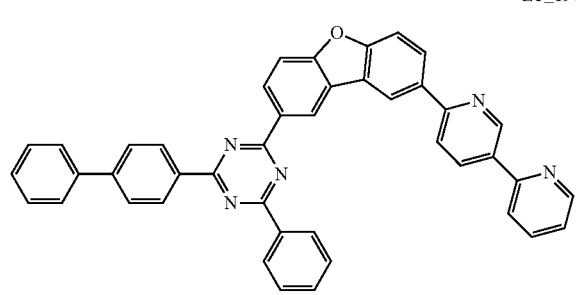
ET_198
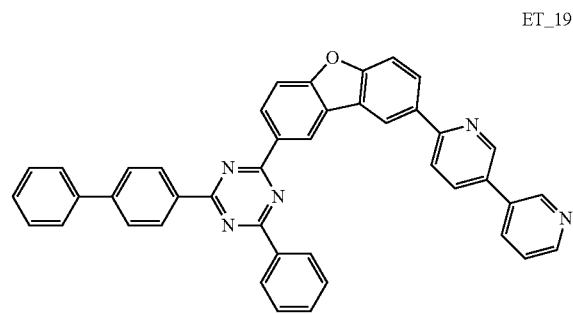
ET_199
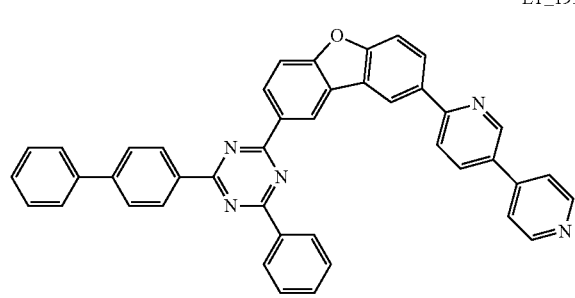
ET_200
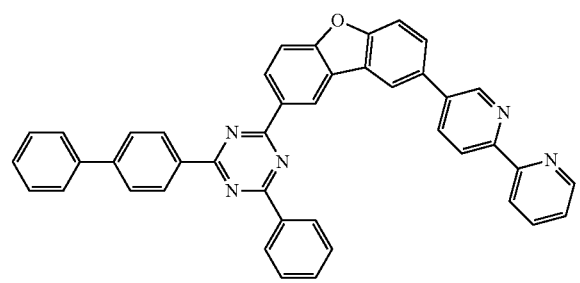
ET_201
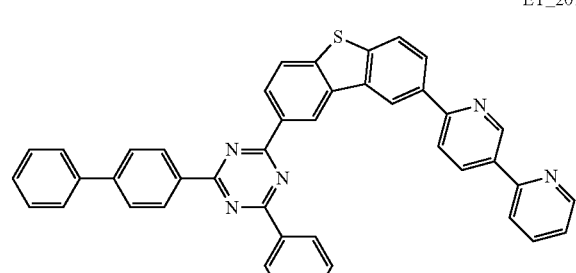
ET_202
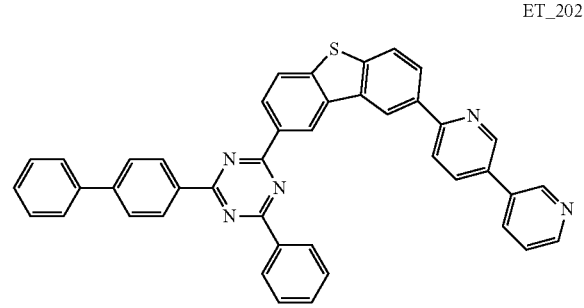
ET_203
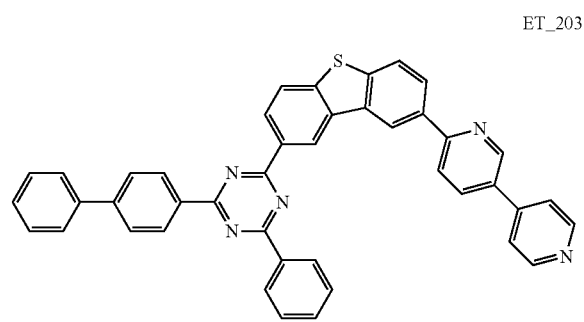
ET_204
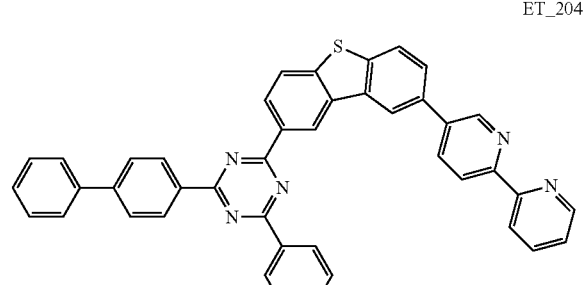

ET_205
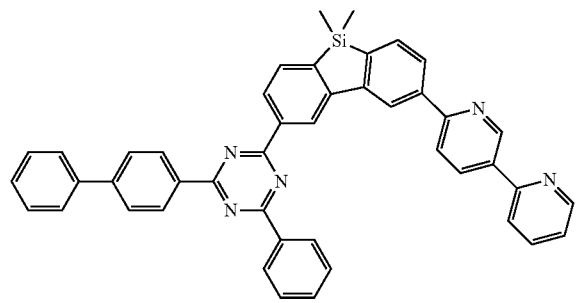
ET_206
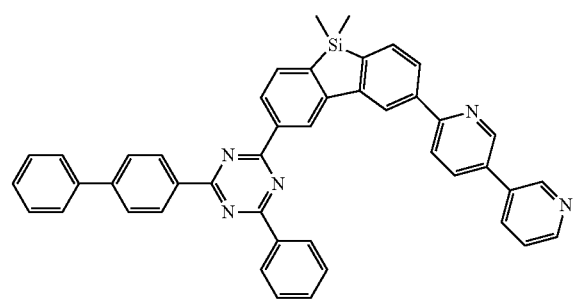
ET_207
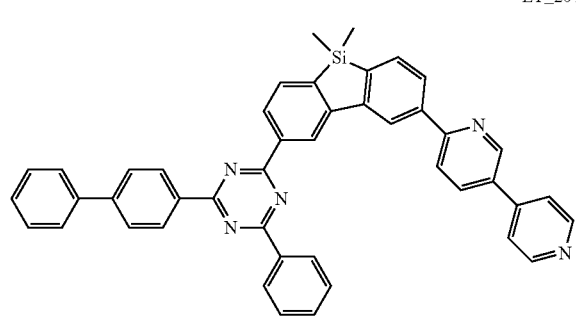
ET_208
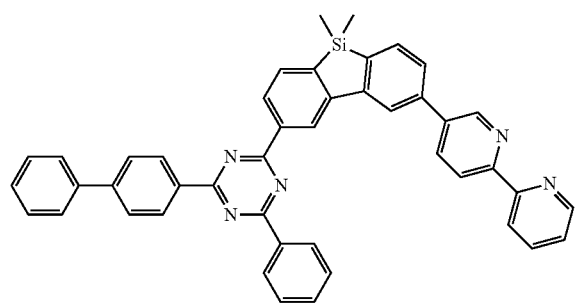
ET_209
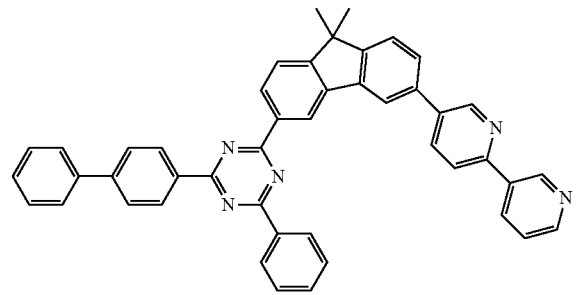
ET_210
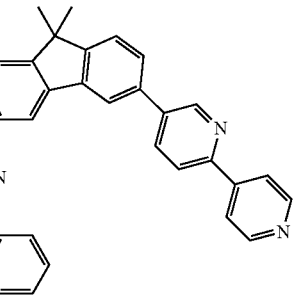
ET_211
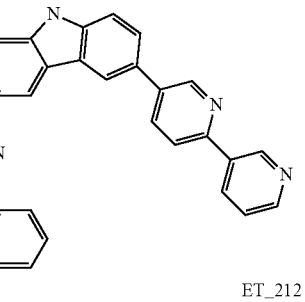
ET_212
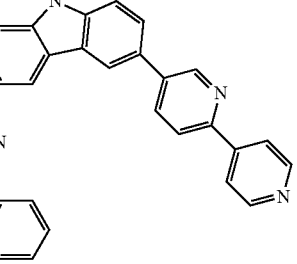
ET_213
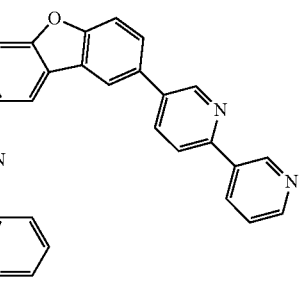
ET_214
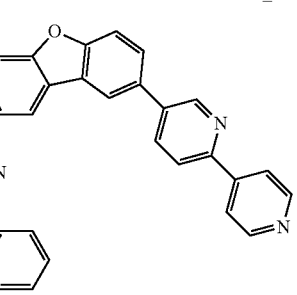

ET_215
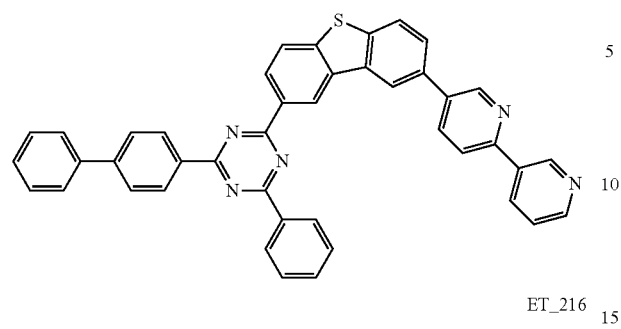
ET_216
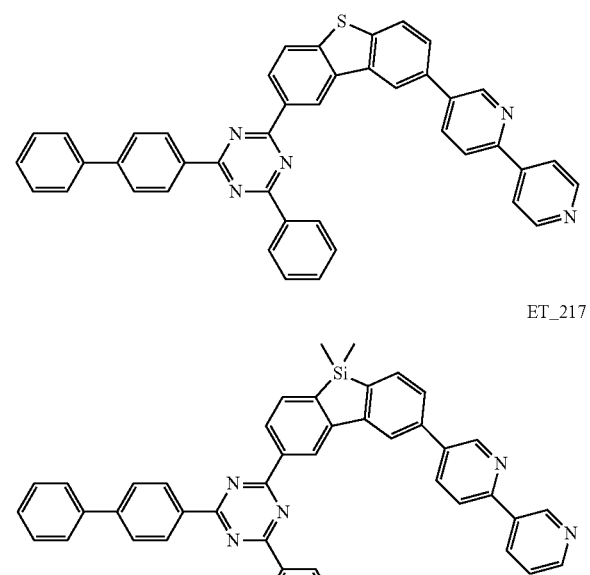
ET_217
ET_218
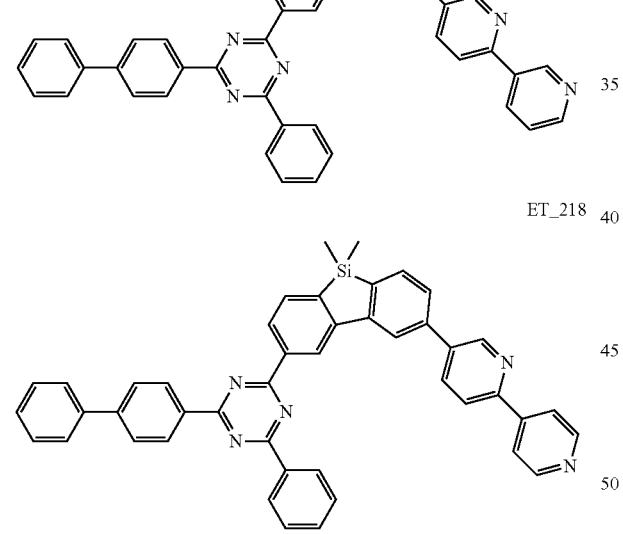
ET_219
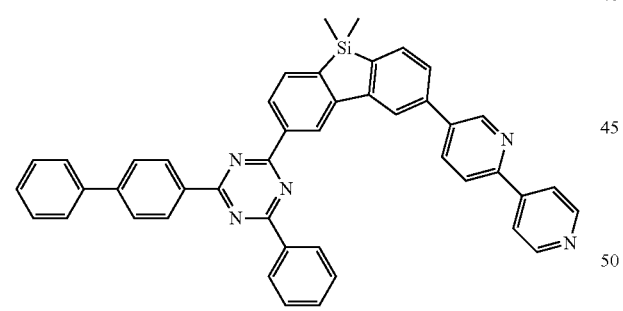
ET_220
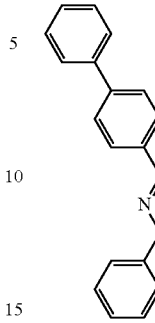
ET_221
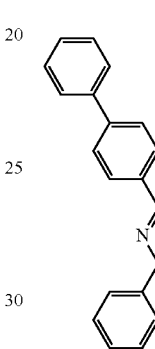
ET_222
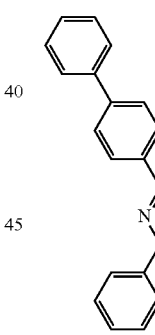
ET_223
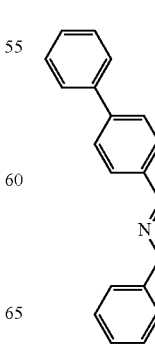

ET_224
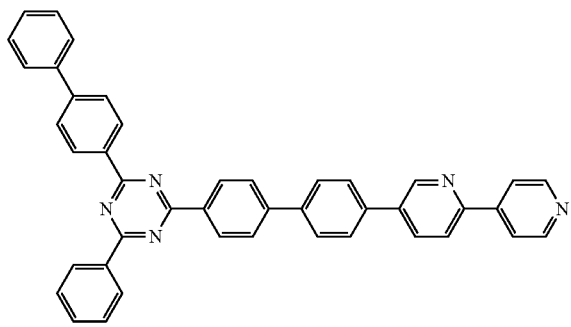
ET_225
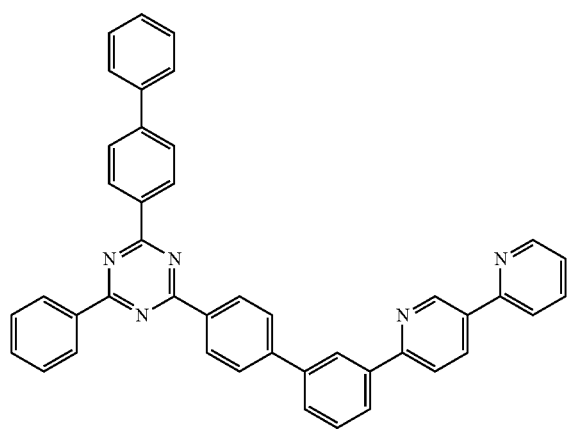
ET_226
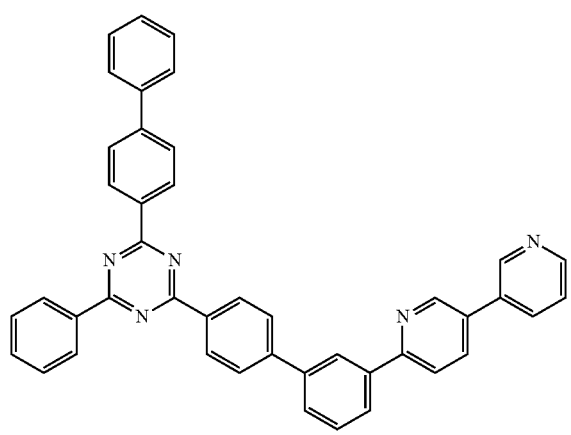
ET_227
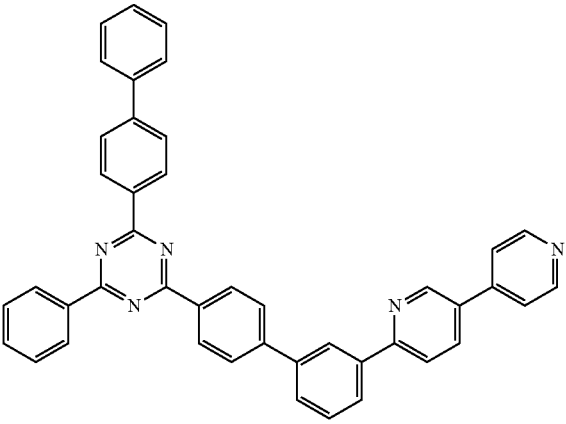
ET_228
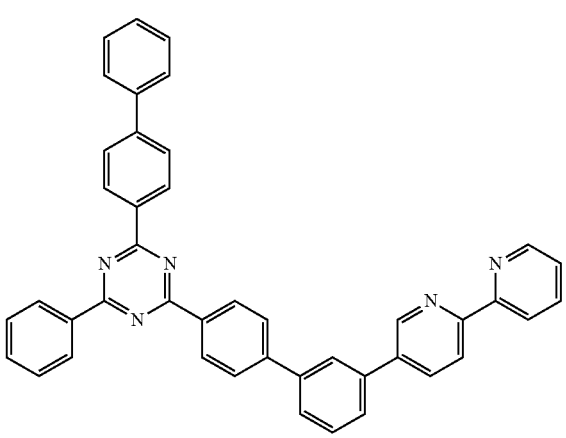
ET_229
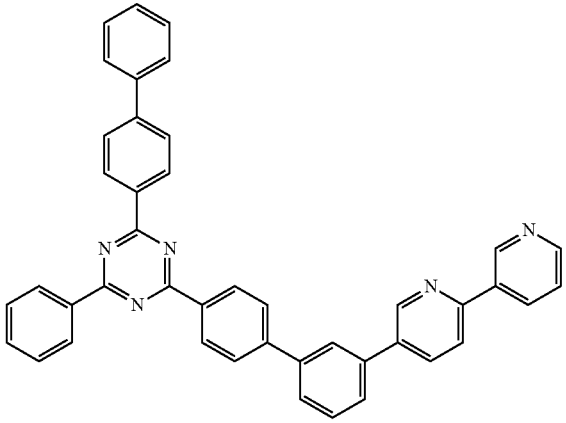

ET_230
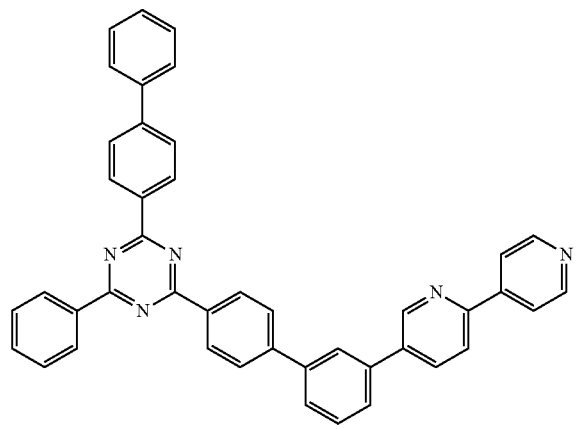
ET_231
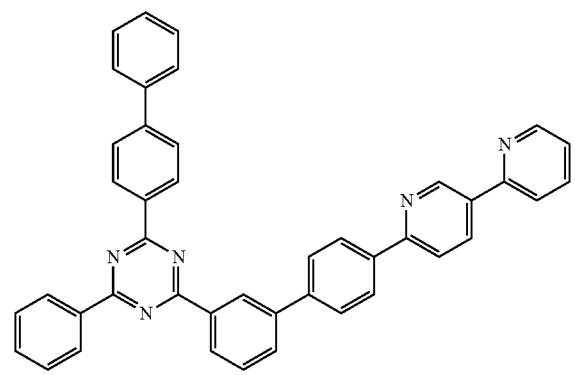
ET_232
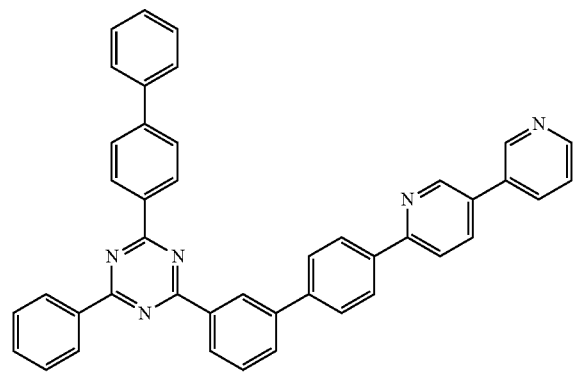
ET_233
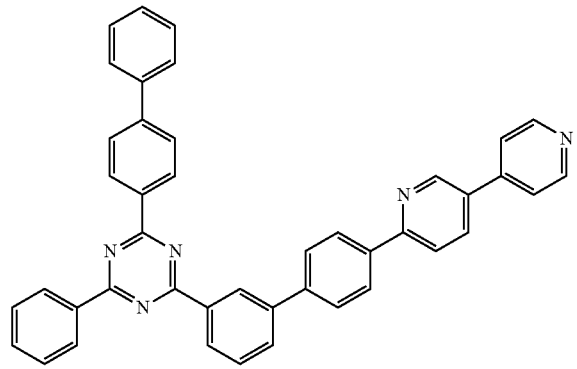
ET_234
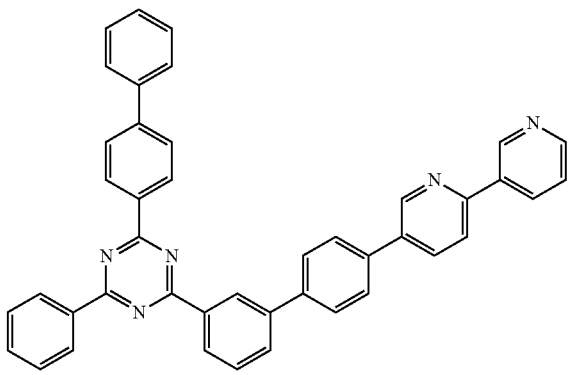
ET_235
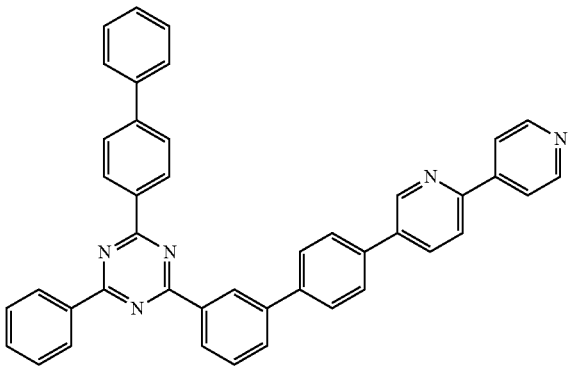
ET_236
ET_237
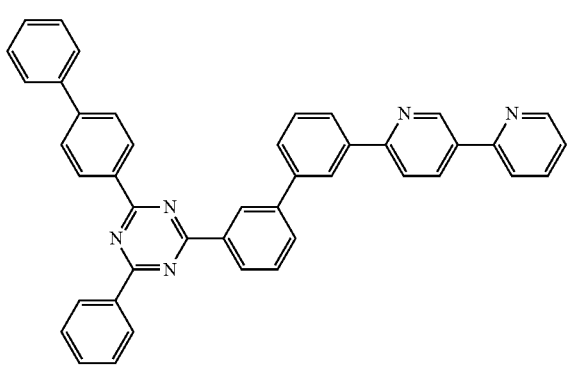

ET_238
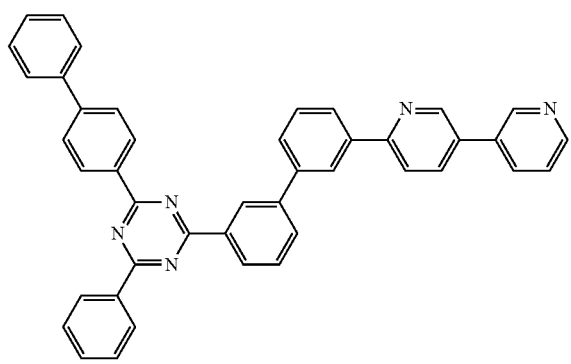
ET_239
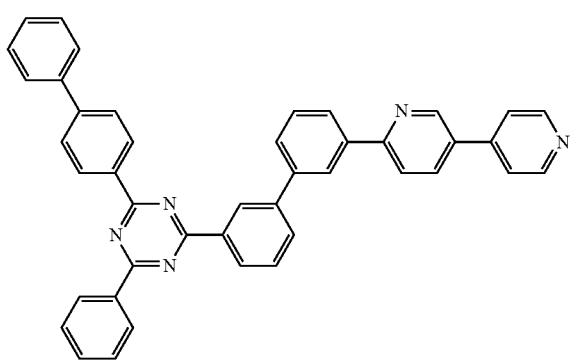
ET_240
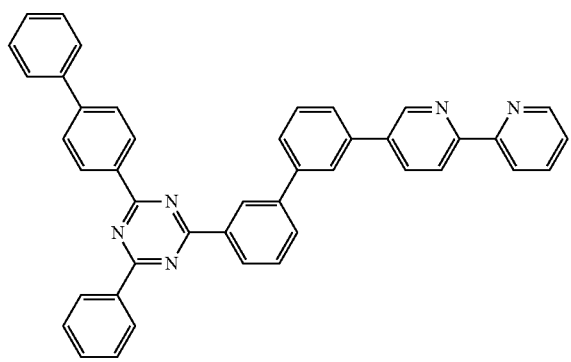
ET_241
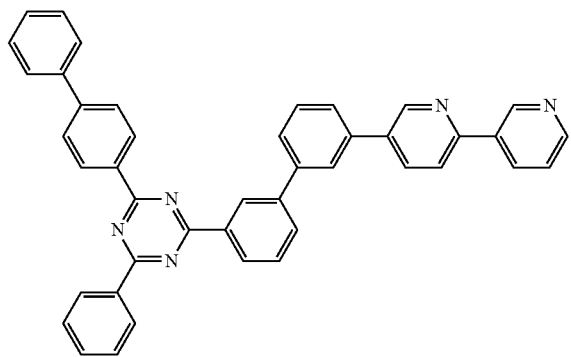
ET_242
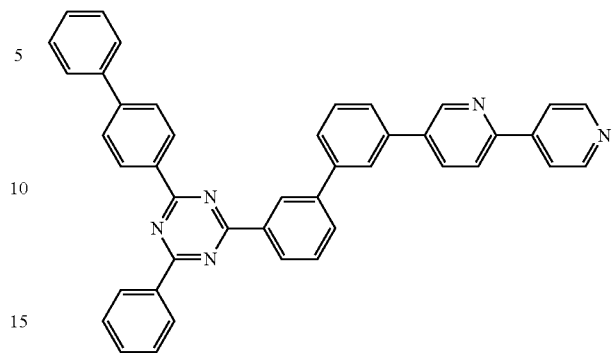
ET_243
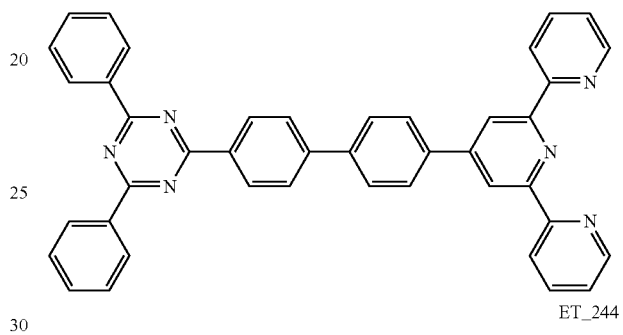
ET_244
ET_245
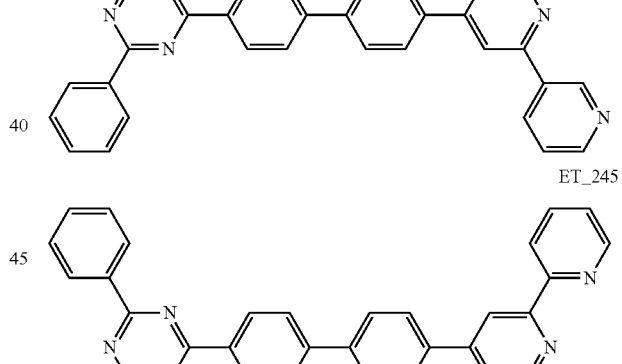
ET_246
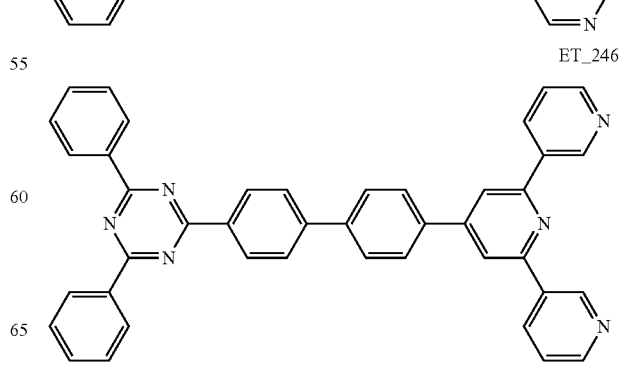

ET_247
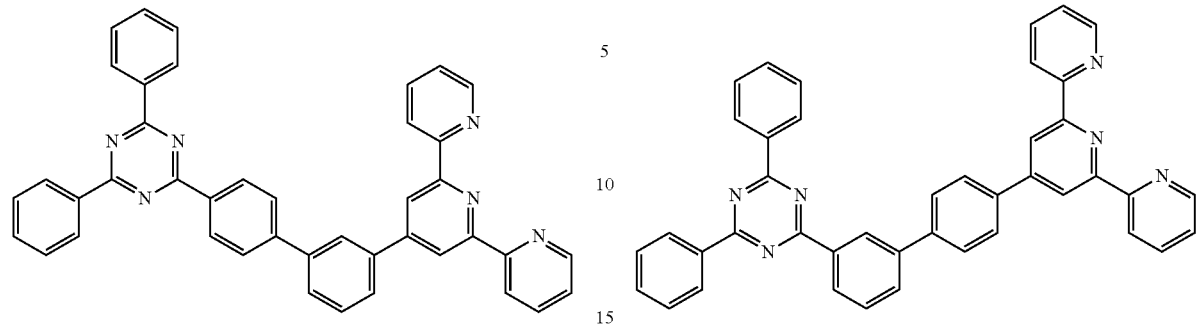
ET_251
ET_248
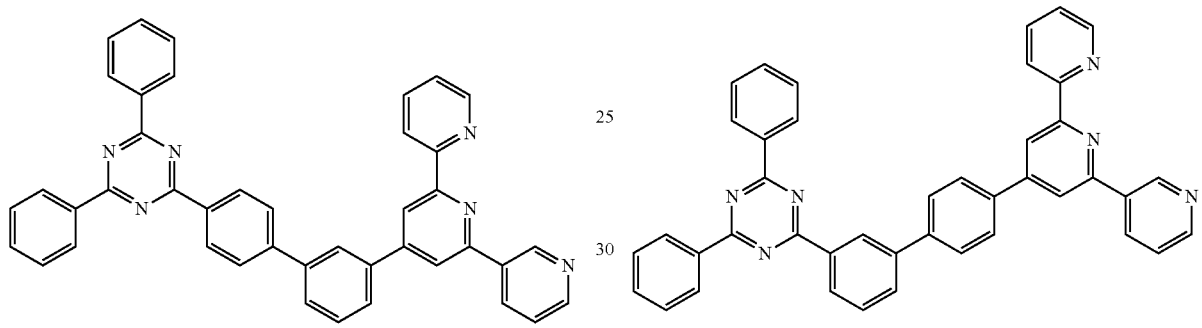
ET_252
ET_249
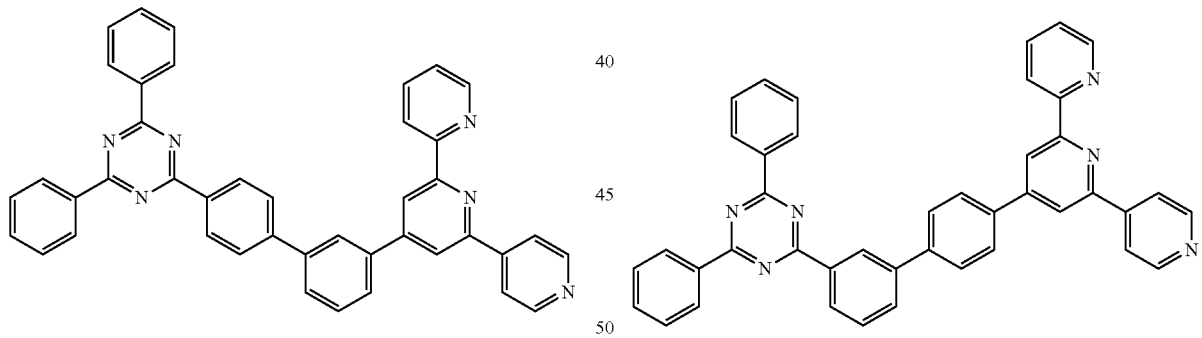
ET_235
ET_250
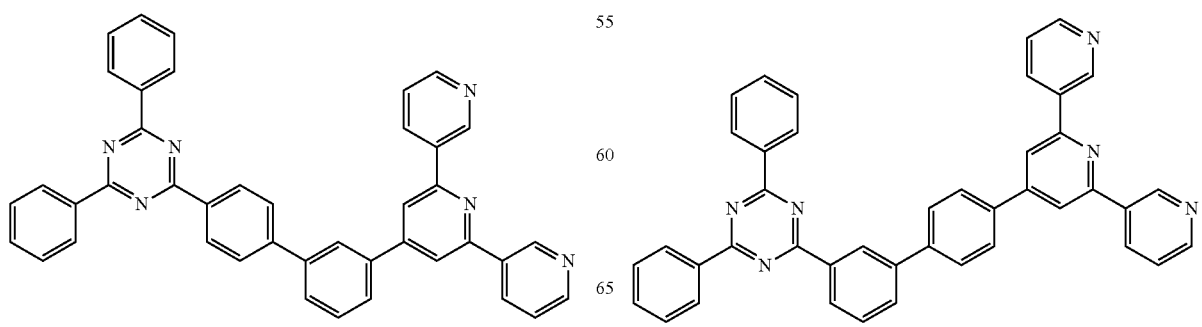
ET_254

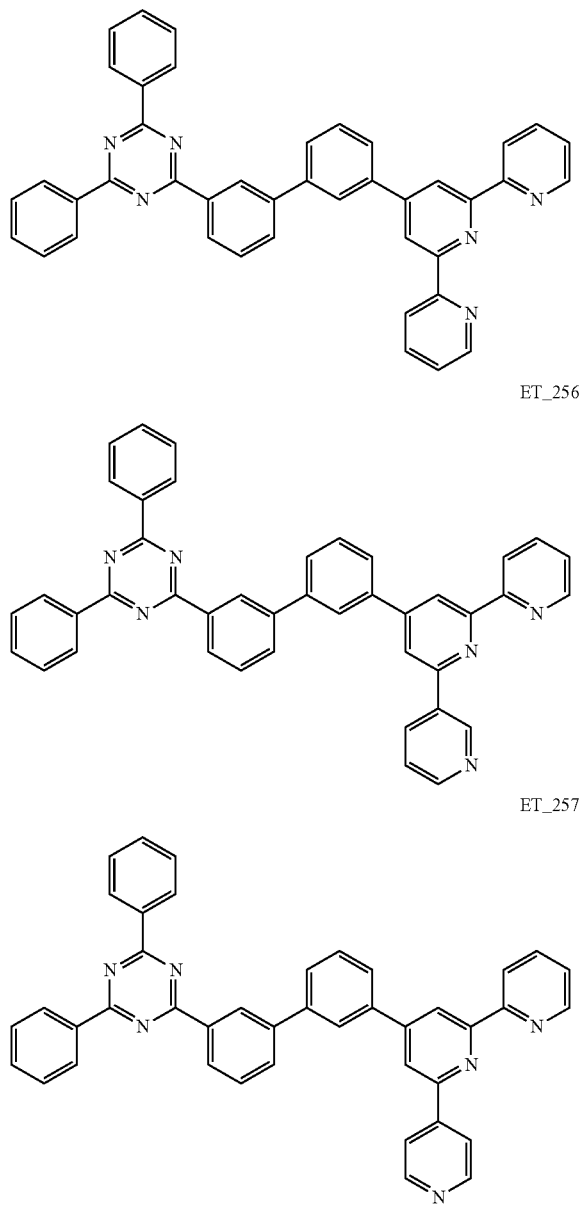
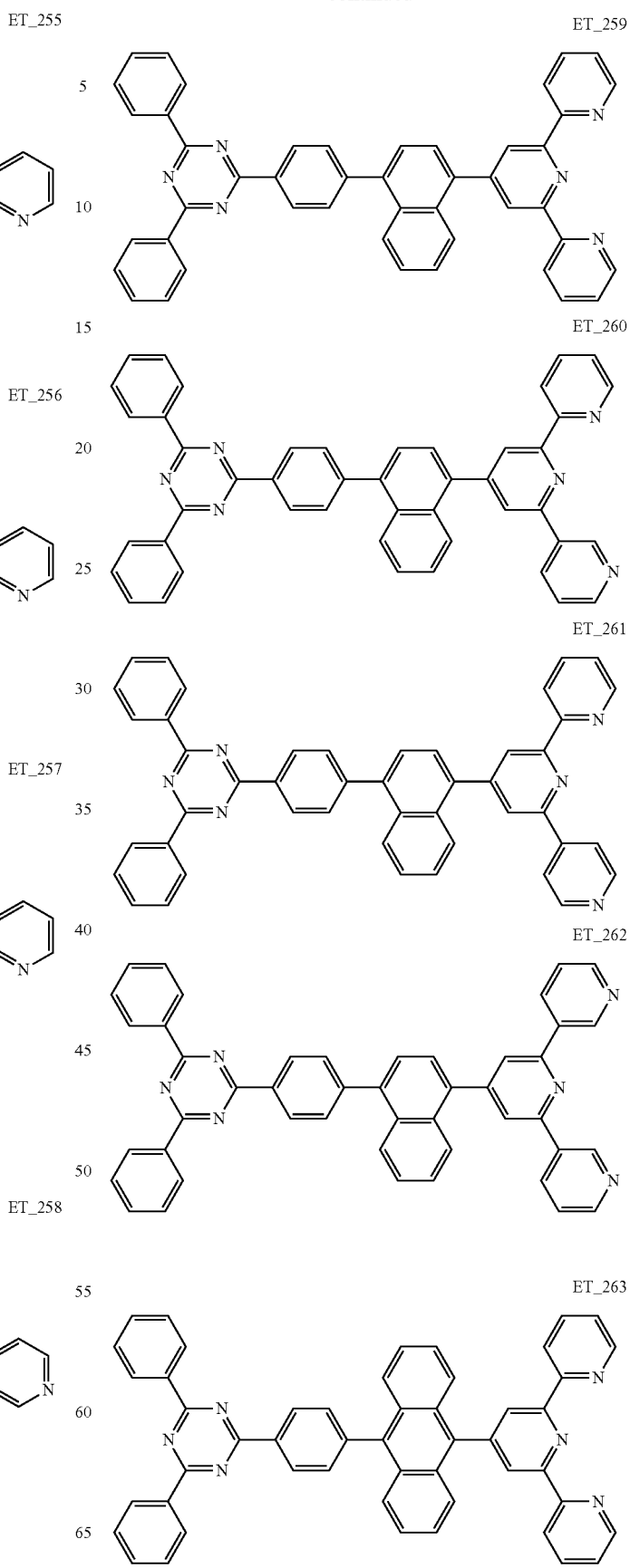

ET_264
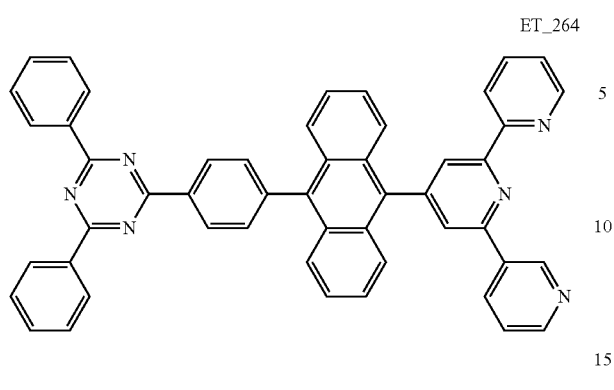
ET_268
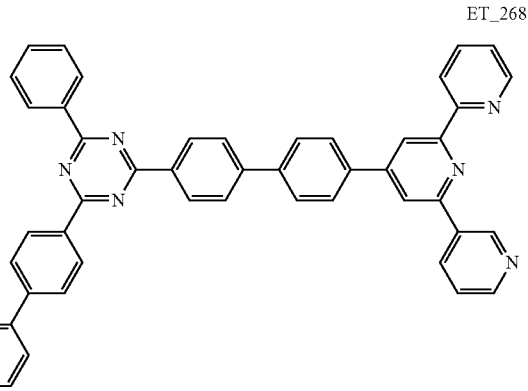
ET_265
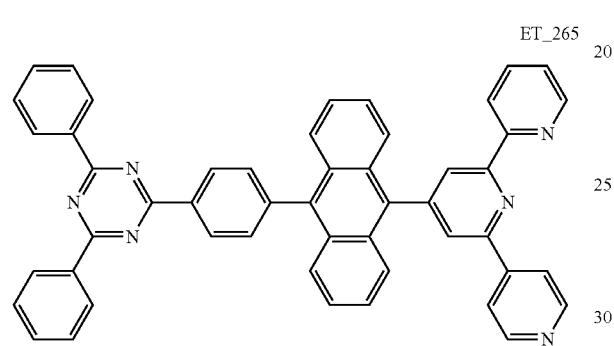
ET_269
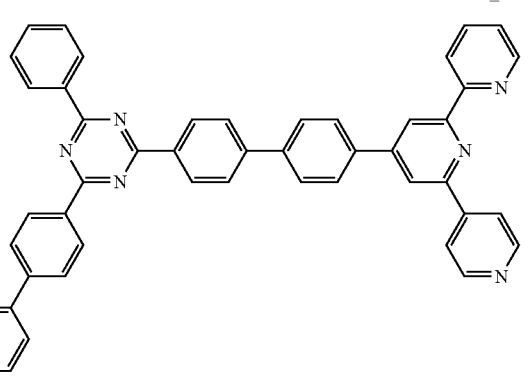
ET_266
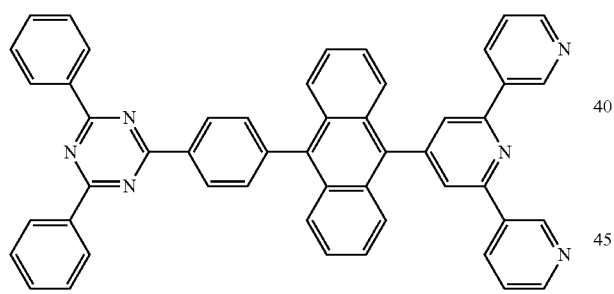
ET_270
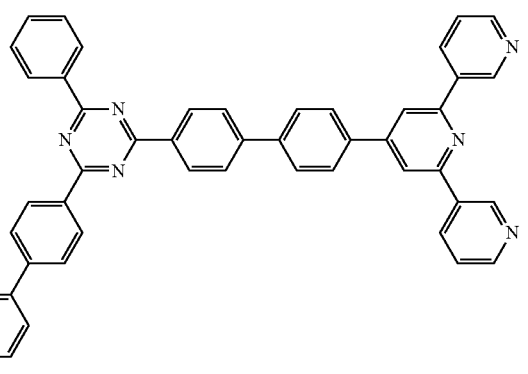
ET_267
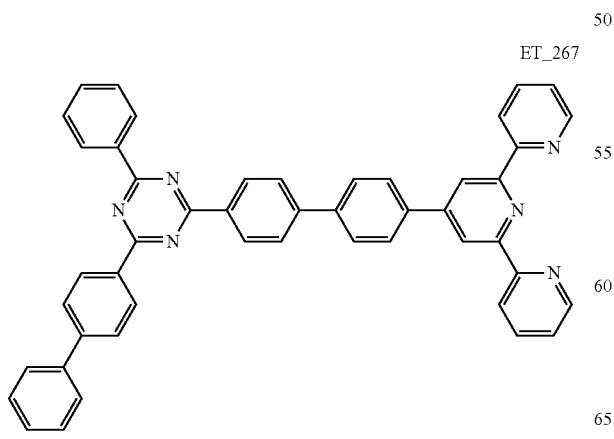
ET_271
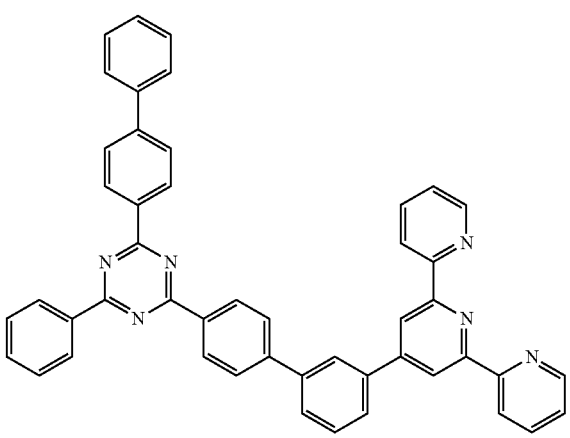

ET_272
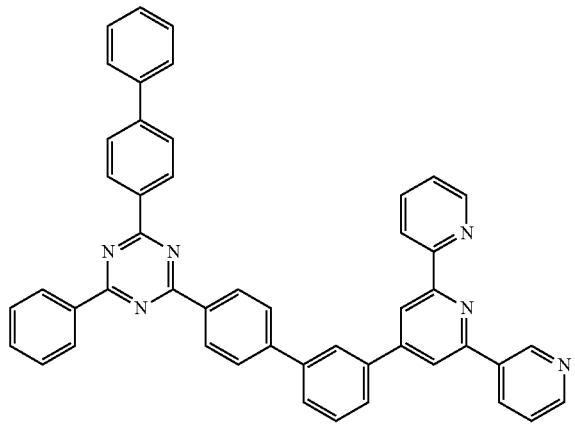
ET_273
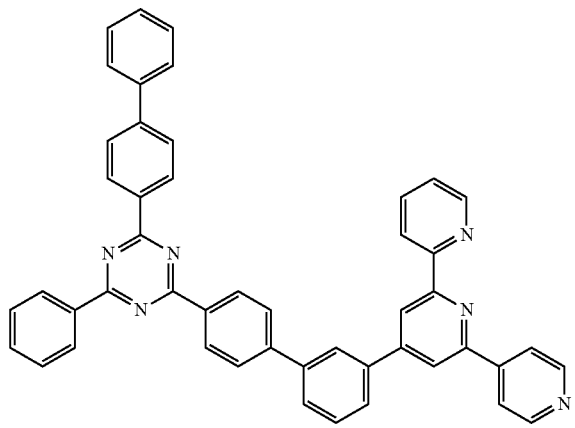
ET_274
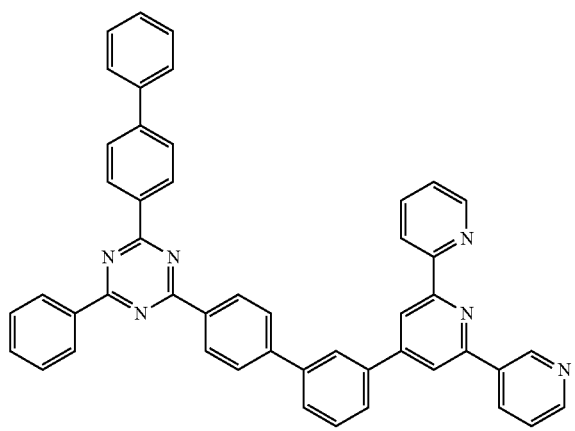
ET_275
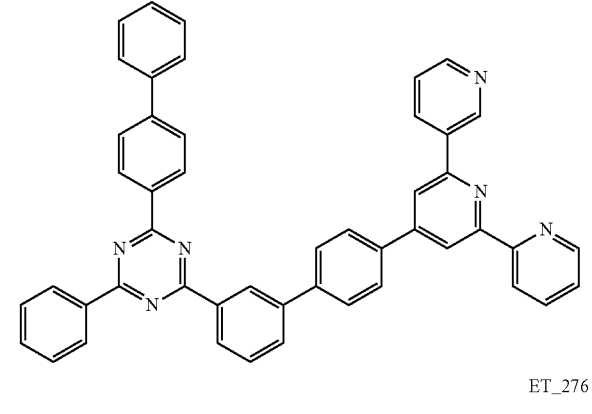
ET_276
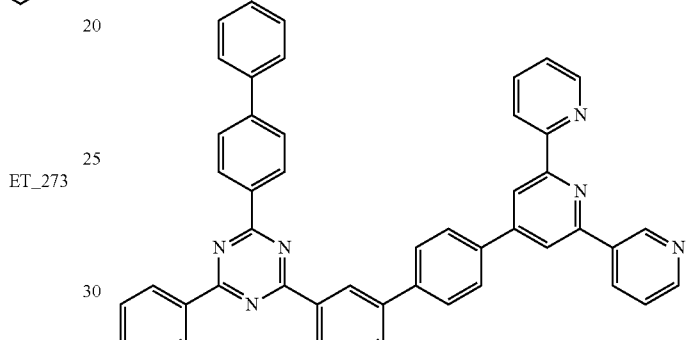
ET_277
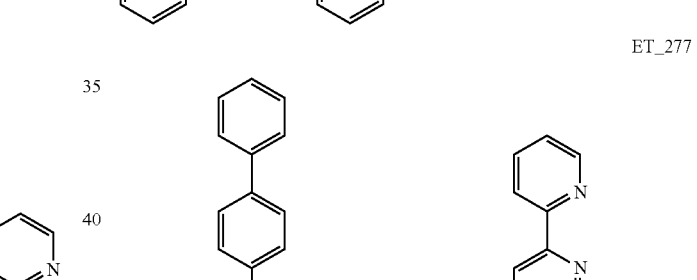
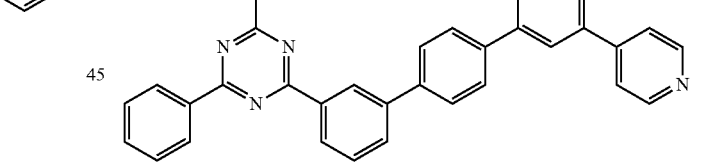
ET_278
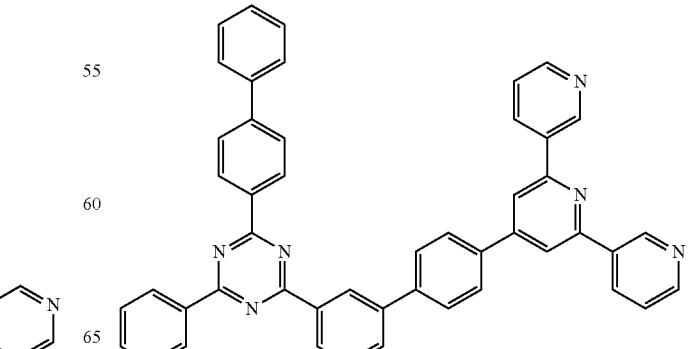

ET_279
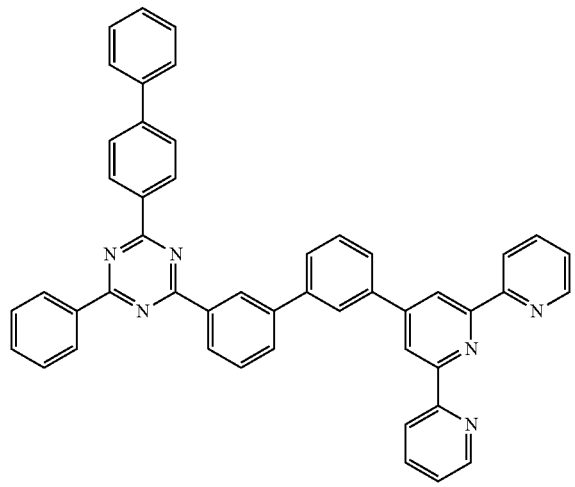
ET_280
ET_282
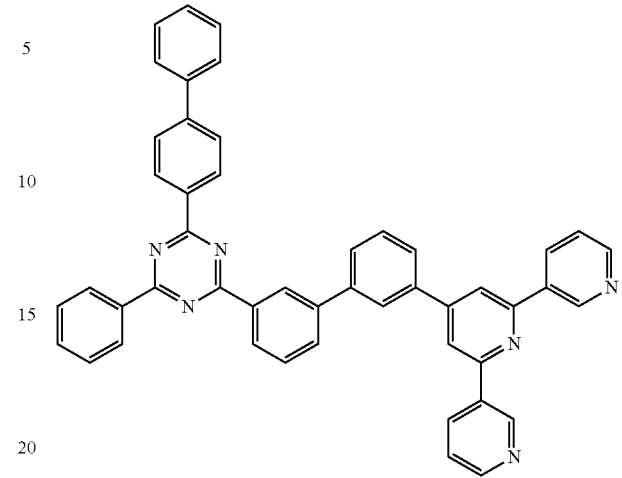
ET_283
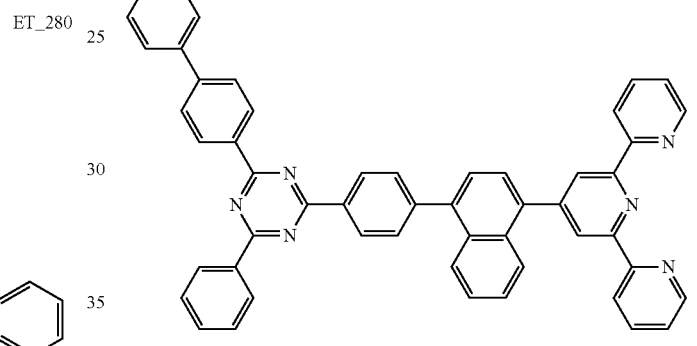
ET_284
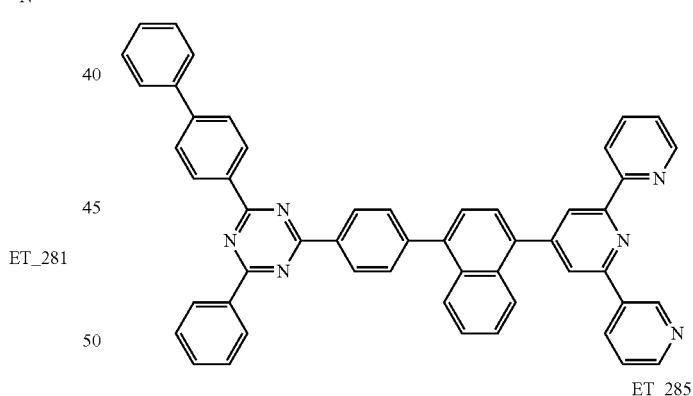
ET_281
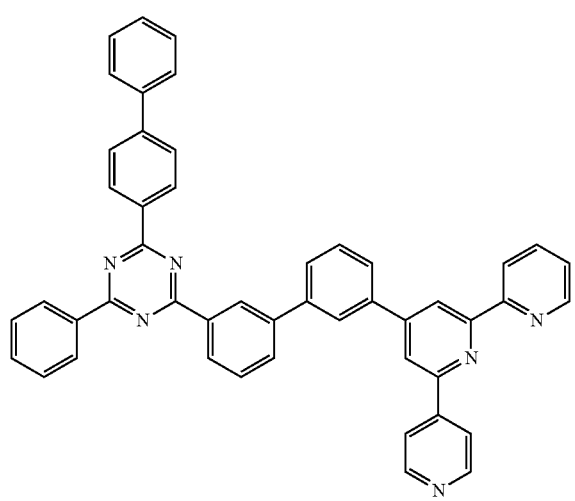
ET_285
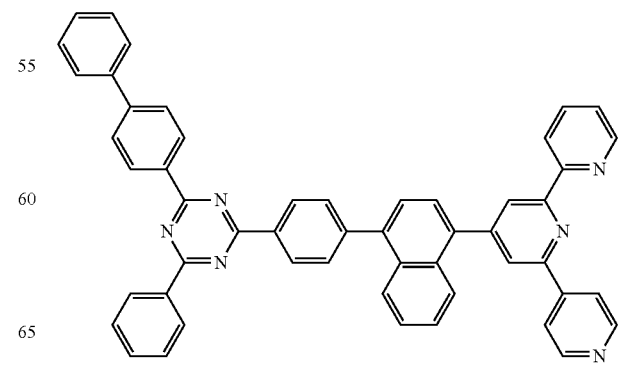

ET_286

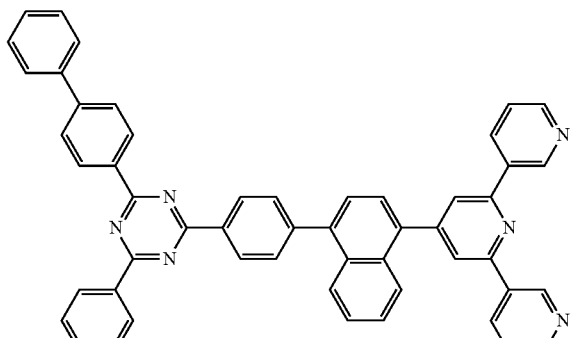

ET_290

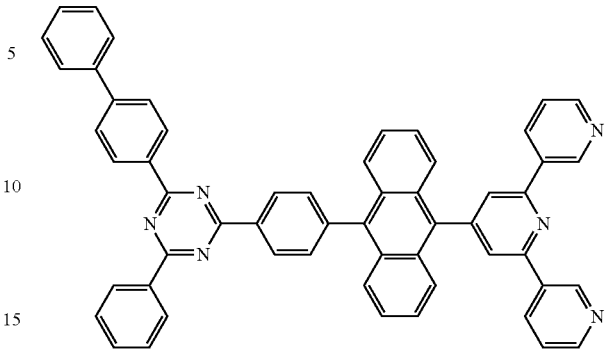

ET_287

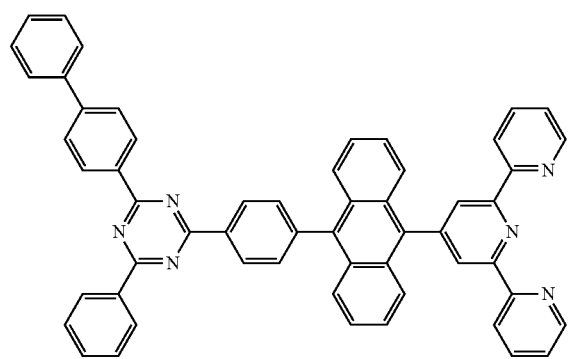

ET_288

ET_289

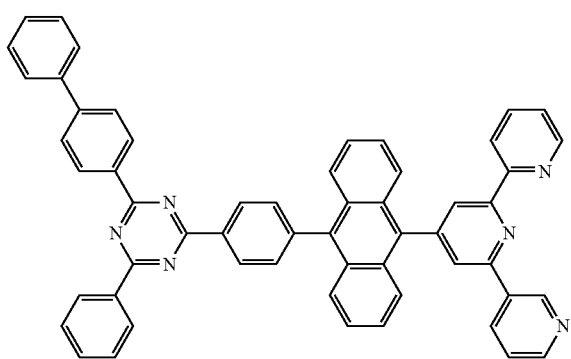

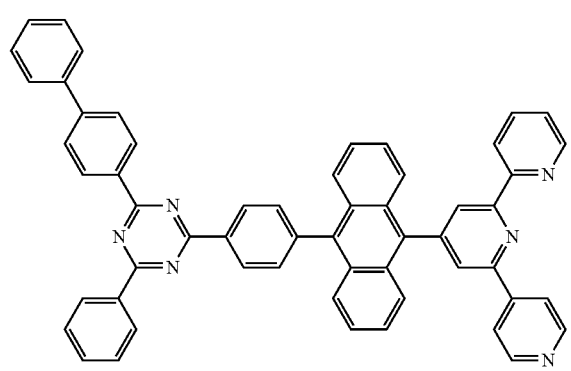

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased. Moreover, since the triazin core and the bipyridine moiety are separated by the at least one linker, the electron localization problem is prevented such that the electron uniformly exists in the organic compound. As a result, the electron from a cathode or an N-type charge generation layer (CGL) is efficiently injected or transported into an electron transporting layer (ETL) or an emitting material layer (EML). Accordingly, when the organic compound is used for at least one of an electron injection layer (EIL), the ETL and the N-type CGL of an organic light emitting diode, the electron injection/transporting property in the organic light emitting diode is increased such that there are advantages in the driving voltage, the lifetime and the emitting efficiency.

In addition, since the organic compound (e.g., the nitrogen atom in the triazin core) is combined with the alkali metal or the alkali earth metal in the ETL or the N-type CGL, the diffusion of the alkali metal or the alkali earth metal into the EML or the P-type CGL is prevented. Further, since the nitrogen atom of the triazin core in the organic compound is combined or bonded with the alkali metal or the alkali earth metal as a dopant in the ETL or an N-type CGL to form a gap state, the electron transporting property of the ETL or the N-type CGL is further improved.

As mentioned above, the organic compound of the present invention includes the triazin core, which has excellent electron transporting/injection property, and the bipyridine moiety, which has excellent electronegativity, connected to the each other via at least one linker. Accordingly, the organic compound is used for a layer of the organic light emitting diode requiring the electron transporting property and/or the electron injection property.

FIG. 1 is a schematic cross-sectional view of an organic light emitting diode according to a first embodiment of the present invention.

As shown in FIG. 1, the organic light emitting diode D1 includes a first electrode 180, a second electrode 184, an organic emitting layer 182 (e.g., an organic material layer or an emitting part) between the first and second electrodes 180 and 184. The organic emitting layer 182 includes a hole injection layer (HIL) 210, a hole transporting layer (HTL) 220, an emitting material layer (EML) 230, an electron transporting layer (ETL) 240 and an electron injection layer (EIL) 250 sequentially stacked on the first electrode 180. Namely, the organic light emitting diode D1 of the first embodiment of the present invention includes a single emitting part.

The first electrode 180 is the anode for injecting a hole and includes a high work function conductive material, e.g., indium-tin-oxide (ITO), indium-zinc-oxide (IZO) or zinc oxide (ZnO). The second electrode 184 is the cathode for injecting an electron and includes a low work function conductive material, e.g., aluminum (Al), magnesium (Mg) or Al—Mg alloy.

The HIL 210 is positioned between the first electrode 180 and the HTL 220. An interface property between the first electrode 180 of an inorganic material and the HTL 220 of an organic material is improved by the HIL 210. For example, the HIL 210 may include one of 4,4',4''-tris(3-methylphenylphenylamino)triphenylamine (MTDATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4''-diamine (NPB or NPD), 1,4,5,8,9,11-hexaazatriphenylenehexacarbonitrile (HATCN), 1,3,5-tris [4-(diphenylamino)phenyl]benzene (TDAPB), poly(3,4-ethylenedioxythiphene)polystyrene sulfonate (PEDOT/PSS), 2,3,5,6-tetrafluoro-7,7,8,8-tetracyanoquinodimethane (F4TCNQ) and N-(biphenyl-4-yl)-9,9-dimethyl-N-(4-(9-phenyl-9H-carbazol-3-yl)phenyl)-9H-fluoren-2-amine.

The HIL 210 may have a thickness of about 1 to 150 nm. The hole injection property may be improved with the thickness above 1 nm, and an increase of the driving voltage resulting from an increase of the thickness of the HIL 210 may be prevented with the thickness below 150 nm. The HIL 210 may be omitted.

The HTL 220 is positioned between the HIL 210 and the EML 230. For example, the HTL 220 may include a hole transporting material such as N,N'-diphenyl-N,N'-bis(3-methylphenyl)-1,1'-biphenyl-4,4'-diamine (TPD), MTDATA, TCTA, NPD or 4,4'-bis(N-carbazolyl)-1,1'-biphenyl (CBP). The HTL 220 may have a double-layered structure of different hole transporting materials.

The HTL 220 may have a thickness of about 1 to 150 nm. The hole transporting property may be improved with the thickness above 1nm, and an increase of the driving voltage resulting from an increase of the thickness of the HTL 220 may be prevented with the thickness below 150 nm.

The EML 230 may include a host and a dopant. For example, when the EML 230 emits blue light, a fluorescent host, such as anthracene derivative, pyrene derivative or perylene derivative, and a fluorescent dopant are used for the EML 230.

For example, the fluorescent host for the EML 230 may be selected from the group consisting of 4,4'-bis(2,2'-diphenylyinyl)-1,1'-biphenyl (DPVBi), 9, 10-di-(2-naphtyl)anthracene (ADN), 2,5,8,11-tetra-t-butylperylene (TBADN), 2-tert-butyl-9,10-di(2-naphthyl)anthracene, 2-methyl-9,10-di(2-naphtyl)anthracene (MADN) and 2,2',2''-(1,3,5-benzinetriyl)-tris(1-phenyl-1-H-benzimidazole) (TBPi).

For example, the fluorescent dopant for the EML 230 may be selected from the group consisting of 4,4'-bis(9-ethyl-3-carbazovinylene)-1,1'-biphenyl (BCzVBi), 2,5,8,11-tetra (tert-butyl)perylene (TBP) and diphenyl-[4-(2-[1,1;4,1]terphenyl-4-yl-vinyl)-phenyl]-amine (BD-1).

When the EML 230 emits green light or red light, the EML 230 may include a phosphorescent host, e.g., carbazole derivative, and a phosphorescent dopant, e.g., a metal (iridium) complex. The dopant may have a weight % of about 1 to about 30 with respect to the host.

The ETL 240 is positioned between the EML 230 and the second electrode 184, and the EIL 250 is positioned between the ETL 240 and the second electrode 184.

The ETL 240 may include a derivative of oxadiazole, triazole, phenanthroline, benzoxazole, benzothiazole, benzimidazole and triazine. For example, the ETL 240 may include an electron transporting material selected from a group consisting of tris-(8-hydroxyquinoline aluminum (Alq3), 2-biphenyl-4-yl-5-(4-t-butylphenyl)-1,3,4-oxadiazole (PBD), spiro-PBD, Liq, 2-[4-(9,10-Di-2-naphthalenyl-2-anthracenyl)phenyl]-1-phenyl-1H-benzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline (TPQ) and 1,3,5-tris(N-phenylbenzimiazole-2-yl)benzene (TPBI), but it is not limited thereto.

Alternatively, the ETL 240 may include the above electron transporting material and the organic compound of the present invention as a dopant. In this instance, the organic compound may have a weight % of about 1 to 30 with respect to the electron transporting material, but it is not limited thereto.

The ETL 240 may have a thickness of about 1 to 150 nm. The electron transporting property may be improved with the thickness above 1 nm, and an increase of the driving voltage resulting from an increase of the thickness of the ETL 240 may be prevented with the thickness below 150 nm.

An electron injection is improved by the EIL 250. The EIL 250 may include the organic compound of the present invention. A dopant, e.g., an alkali metal or an alkali earth metal, may be doped into the EIL 250 to improve the electron injection property. The dopant may have a weight % of about 1 to 20 with respect to the organic compound, but it is not limited thereto. For example, the dopant may be one of Li, Na, K, Cs, Mg, Sr, Ba and Ra. Alternatively, the dopant may be a metal compound, i.e., an alkali metal compound or an alkali earth metal compound, such as Liq, LiF, NaF, KF, RbF, CsF, FrF, BeF$_2$, MgF$_2$, CaF$_2$, SrF$_2$, BaF$_2$ or RaF$_2$.

The EIL 250 may have a thickness of about 1 to 50 nm. The electron injection property may be improved with the thickness above 1 nm, and an increase of the driving voltage resulting from an increase of the thickness of the EIL 250 may be prevented with the thickness below 50 nm.

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased. Accordingly, when the organic compound is used for at least one of the EIL and the ETL of an organic light emitting diode, the electron injection/transporting property into the EML in the organic light emitting diode is increased such that there are advantages in the driving voltage, the lifetime and the emitting efficiency.

On the other hand, the organic compound of the present invention may be applied to a tandem structure organic light emitting diode emitting the white light. The tandem structure white organic light emitting diode may be used for a lighting apparatus, a thin light source, a backlight unit of a liquid crystal display device and a full color display device including a color filter.

In the white organic light emitting diode, properties of color purity and color stability as well as an emitting efficiency and a lifetime are important considerations. For example, the white organic light emitting diode may be classified into a single-layered emission structure and a multi-layered emission structure. To achieve a long lifetime white organic light emitting diode, the white organic light emitting diode having a stack structure of at least two emitting parts may be used. This structure may be referred to as the tandem structure.

Figure 2:
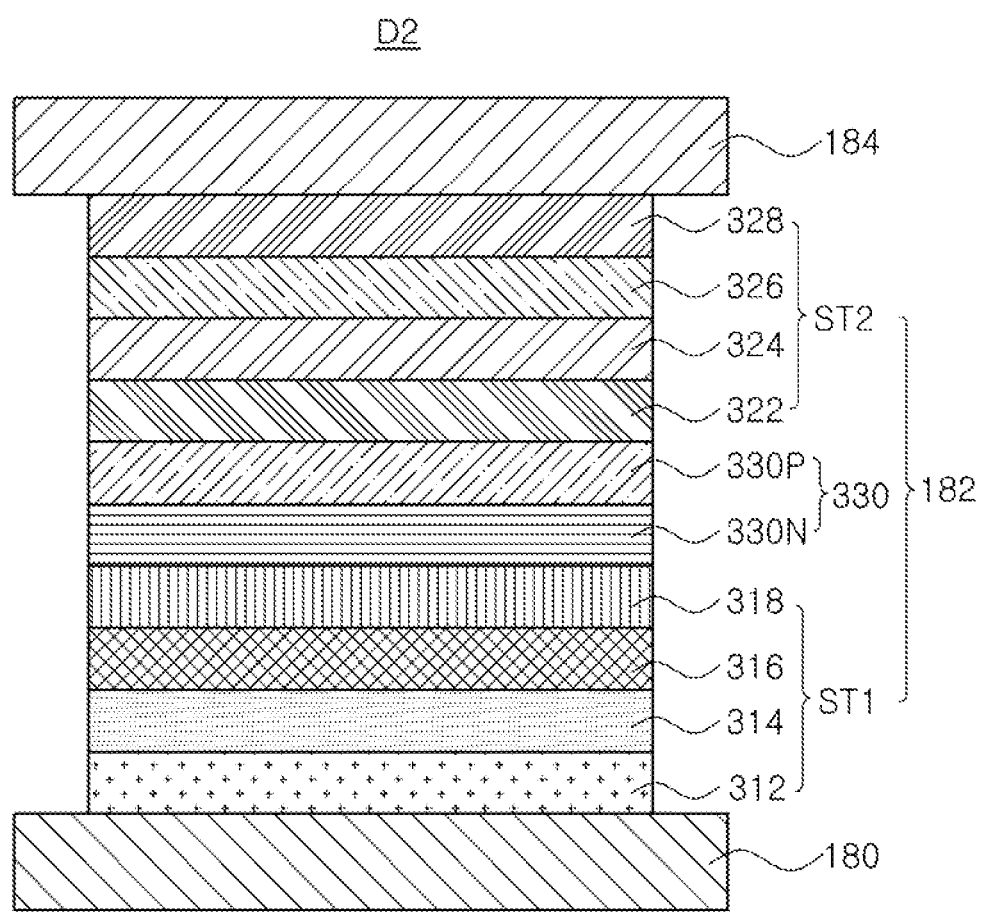
FIG. 2 is a schematic cross-sectional view of an organic light emitting diode according to a second embodiment of the present invention.

FIG. 2 is a schematic cross-sectional view of an organic light emitting diode according to a second embodiment of the present invention.

As shown in FIG. 2, the organic light emitting diode D2, which includes two emitting parts, includes a first electrode 180, a second electrode 184, an organic emitting layer 182 between the first and second electrodes 180 and 184 and including first and second emitting parts ST1 and ST2 and a charge generation layer (CGL) 330.

The first electrode 180 is the anode for injecting a hole and includes a high work function conductive material, e.g., ITO, IZO or ZnO. The second electrode 184 is the cathode for injecting an electron and includes a low work function conductive material, e.g., Al, Mg or Al—Mg alloy.

The CGL 330 is positioned between the first and second emitting parts ST1 and ST2. Namely, the first emitting part ST1, the CGL 330 and the second emitting part ST2 are sequentially stacked on the first electrode 180. In other words, the first emitting part ST1 is positioned between the first electrode 180 and the CGL 330, and the second emitting part ST2 is positioned between the second electrode 184 and the CGL 330.

The first emitting part ST1 may include an HIL 312, a first HTL 314, a first EML 316 and a first ETL 318 sequentially stacked on the first electrode 180. Namely, the HIL 312 and the first HTL 314 are positioned between the first electrode 180 and the first EML 316. The HIL 312 is positioned between the first electrode 180 and the first HTL 314, and the first HTL 314 is positioned between the HIL 312 and the first EML 316. In addition, the first ETL 318 is positioned between the first EML 316 and the CGL 330.

A hole injection from the first electrode 180 into the first EML 316 is improved by the HIL 312. The HIL 312 may include at least one selected from the group consisting of MTDATA, CuPc, TCTA, NPD, HATCN, TDAPB), PEDOT/PSS, F4TCNQ and N-(biphenyl-4-yl)-9,9-dimethyl-N-(4-(9-phenyl-9H-carbazole-3-yl)phenyl)-9H-fluorene-2amine.

The HIL 312 may have a thickness of about 1 to 150 nm. The hole injection property may be improved with the thickness above 1 nm, and an increase of the driving voltage resulting from an increase of the thickness of the HIL 312 may be prevented with the thickness below 150 nm. The HIL 312 may be omitted according to the structure or property of the organic light emitting diode.

A hole transporting is improved by the first HTL 314. The first HTL 314 may include at least one selected from a group consisting of TPD, TCTA, MTDATA, NPD and CBP, but it is not limited thereto. The first HTL 314 may have a single-layered structure or a multi-layered structure.

The first HTL 314 may have a thickness of about 1 to 150 nm. The hole transporting property may be improved with the thickness above 1 nm, and an increase of the driving voltage resulting from an increase of the thickness of the first HTL 314 may be prevented with the thickness below 150 nm.

The first EML 316 may be a blue EML. Alternatively, the first EML 316 may be a red EML, a green EML or a yellow EML. When the first EML 316 is the blue EML, the first EML 316 may be a blue EML, a dark blue EML or a sky blue EML. In addition, the first EML 316 may be a double-layered structure of the blue EML and the red EML, the blue EML and yellow-green EML, or the blue EML and the green EML.

When the first EML 316 is the red EML, the first EML 316 may be a phosphorescent EML including a host, e.g., 4,4'-bis(carbazol-9-yl)biphenyl (CBP), and at least one dopant selected from the group consisting of bis(1-phenylisoquinoline)acetylacetonate iridium (PIQIr(acac), bis(1-phenylquinoline)acetylacetonate iridium(PQIr(acac) and tris(1-phenylquinoline)iridium(PQIr) and octaethylporphyrin platinum (PtOEP), but it is not limited thereto. Alternatively, the first EML 316 may be a fluorescent EML including PBD:Eu(DBM)$_3$(Phen) or perylene. In this instance, the first emitting part ST1 has an emission peak range of about 600 to 650 nm.

When the first EML 316 is the green EML, the first EML 316 may be a phosphorescent EML including a host, e.g., CBP, and a dopant of iridium complex, but it is not limited thereto. Alternatively, the first EML 316 may a fluorescent EML including tris(8-hydroxyquinolinato)aluminum (Alq$_3$). In this instance, the first emitting part ST1 has an emission peak range of about 510 to 570 nm.

When the first EML 316 is the blue EML, the first EML 316 may be a phosphorescent EML including a host, e.g., CBP, and a dopant of iridium complex, but it is not limited thereto. Alternatively, the first EML 316 may a fluorescent EML including spiro-DPVBi, Spiro-CBP, distyryl benzene (DSB), distyryl arene (DSA), PFO-based polymer or PPV-based polymer. As mentioned above, the first EML 316 may be a sky blue EML or deep blue (dark blue) EML. In this instance, the first emitting part ST1 has an emission peak range of about 440 to 480 nm.

On the other hand, to improve the emitting efficiency (red efficiency), the first emitting part ST1 may include two EMLs. For example, the first emitting part ST1 may include the blue EML and the red EML. In this instance, the first emitting part ST1 has an emission peak range of about 440 to 650 nm.

In addition, the first EML 316 may have a single-layered structure of the yellow-green EML or a double-layered structure of the yellow-green EML and the green EML. In this instance, the first EML 316 may include at least one host selected from a group consisting of CBP and bis(2-methyl-8-quinolinolate)-4-(phenylphenolato)aluminium (BAlq) and a phosphorescent yellow-green dopant. The first emitting part ST1 has an emission peak range of about 510 to 590 nm.

When the first emitting part ST1 includes two EMLs of the yellow-green EML and the red EML to improve the emitting efficiency (red efficiency), the first emitting part ST1 has an emission peak range of about 510 to 650 nm.

An electron transporting is improved by the first ETL 318. The first ETL 318 may include an electron transporting material selected from a group consisting of Alq3, PBD, spiro-PBD, Liq, 2-[4-(9,10-Di-2-naphthalenyl-2-anthracenyl)phenyl]-1-phenyl-1H-benzimidazol, TAZ, Bphen, TPQ and TPBI. Alternatively, the first ETL 318 may include the above electron transporting material and the organic compound of the present invention as a dopant.

The first ETL 318 may have a thickness of about 1 to 150 nm. The electron transporting property may be improved with the thickness above 1 nm, and an increase of the driving voltage resulting from an increase of the thickness of the first ETL 318 may be prevented with the thickness below 150 nm.

The second emitting part ST2 may include a second HTL 322, a second EML 324, a second ETL 326 and an EIL 328. The second HTL 322 is positioned between the CGL 330 and the second EML 324, and the second ETL 326 is positioned between the second EML 324 and the second electrode 184. In addition, the EIL 328 is positioned between the second ETL 326 and the second electrode 184.

The second HTL 322 and the second ETL 326 may be same as or different from the first HTL 314 and the first ETL 318 in the first emitting part ST1, respectively.

The second EML 324 may be red, green, blue or yellow-green EML. For example, when the first EML 316 is the blue EML, the second EML 324 may be yellow-green EML. Alternatively, the first EML 316 may be the yellow-green EML, and the second EML 324 may be the blue EML.

When the second EML 324 is the yellow-green EML, the second EML 324 may have a single-layered structure of the yellow-green EML or a double-layered structure of the yellow-green EML and the green EML.

For example, the single-layered second EML 324 may include at least one host selected from a group consisting of CBP and bis(2-methyl-8-quinolinolate)-4-(phenylphenolato)aluminium (BAlq) and a phosphorescent yellow-green dopant, but it is not limited thereto.

An electron injection is improved by the EIL 328. The EIL 328 may include an electron injection material being selected from a group consisting of Alq3, PBD, TAZ and BAlq, but it is not limited thereto. Alternatively, the EIL 328 may include the organic compound of the present invention.

The EIL 328 may further include a metal compound as a dopant. The dopant may be one of Liq, LiF, NaF, KF, RbF, CsF, FrF, $BeF_2$, $MgF_2$, $CaF_2$, $SrF_2$, $BaF_2$ or $RaF_2$, but it is not limited thereto. The dopant may have a weight % of about 1 to 20 with respect to the organic compound, but it is not limited thereto.

The EIL 328 may have a thickness of about 1 to 50 nm. The electron injection property may be improved with the thickness above 1 nm, and an increase of the driving voltage resulting from an increase of the thickness of the EIL 328 may be prevented with the thickness below 50 nm.

In the tandem structure organic light emitting diode D2, to increase the current efficiency generating from each of the EMLs 316 and 324 and efficiently distribute the charge, the CGL 330 is positioned between the first emitting part ST1 and the second emitting part ST2. Namely, the first and second emitting parts ST1 and ST2 are connected by the CGL 330. The CGL 330 may be a P-N junction type CGL including an N-type CGL 330N and a P-type CGL 330P.

The N-type CGL 330N is positioned between the first ETL 318 and the second HTL 322, and the P-type CGL 330P is positioned between the N-type CGL 330N and the second HTL 322. The CGL 330 generates a charge or separates a charge into a hole and an electron such that the hole and the electron are provided into the first and second emitting parts ST1 and ST2.

The N-type CGL 330N provides the electron into the first ETL 318 of the first emitting part ST1, and the first ETL 318 provide the electron into the first EML 316 of the first emitting part ST1. On the other hand, the P-type CGL 330P provide the hole into the second HTL 322 of the second emitting part ST2, and the second HTL 322 provide the hole into the second EML 324 of the second emitting part ST2.

The P-type CGL may include an organic material and a dopant, e.g., a metal or a p-type dopant. For example, the metal as the dopant may be selected from the group consisting of Al, Cu, Fe, Pb, Zn, Au, Pt, W, In, Mo, Ni, Ti and their alloy. In addition, the generally known materials may be used as the p-type dopant and the organic material. For example, the p-type dopant may be selected from the group consisting of $F_4$-TCNQ, iodine, $FeCl_3$, $FeF_3$ and $SbCl_5$, and the organic material may be selected from the group consisting of NPB, TPD, N,N,N',N'-tetranaphthalenyl-benzidine (TNB) and HAT-CN.

In the tandem structure organic light emitting diode, when the electrons are transported from the N-type CGL 330N into the first ETL 318, the driving voltage is increased because of a lowest unoccupied molecular orbital (LUMO) energy level difference between each of the first ETL 318 and the N-type CGL 330N.

To overcome the above problem, at least one of the first ETL 318 and the N-type CGL 330N includes an organic compound of the present invention. In addition, each of the first ETL 318 and the N-type CGL 330N may further include alkali metal, alkali metal compound, alkali earth metal or alkali earth metal compound as a dopant.

By doping the above dopant into the first ETL 318 and/or the N-type CGL 330N, the electron transporting/injection property may be further improved. For example, when the dopant is doped into the N-type CGL 330N, the organic compound is combined or bonded with the dopant, e.g., alkali metal, alkali metal compound, alkali earth metal or alkali earth metal compound, in the N-type CGL to form a gap state. As a result, the energy difference between the N-type CGL 330N and the P-type CGL 330P is decreased such that an electron transporting/injection property from the N-type CGL 330N into the first ETL is improved.

For example, the dopant may be one of Liq, LiF, NaF, KF, RbF, CsF, FrF, $BeF_2$, $MgF_2$, $CaF_2$, $SrF_2$, $BaF_2$ or $RaF_2$, may be doped. The dopant may have a weight % of about 1 to 20 with respect to the organic compound, but it is not limited thereto.

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased. Moreover, since the triazin core and the bipyridine moiety are separated by the at least one linker, the electron localization problem is prevented such that the electron uniformly exists in the organic compound.

As a result, the electron from the N-type CGL is efficiently injected or transported into the ETL. Namely, in the present invention, the ETL and/or the N-type CGL include the organic compound having the triazin core and bipyridine moiety, the electron injection/transporting property in the organic light emitting diode is increased such that there are advantages in the driving voltage, the lifetime and the emitting efficiency.

In addition, since the organic compound of the present invention includes the nitrogen atom having a relatively electron rich $sp^2$ hybrid orbital, the nitrogen atom in the organic compound is combined or bonded with the dopant, e.g., alkali metal, alkali metal compound, alkali earth metal or alkali earth metal compound, in the N-type CGL to form a gap state. As a result, the electron is efficiently transported from the N-type CGL into the ETL.

Figure 3:
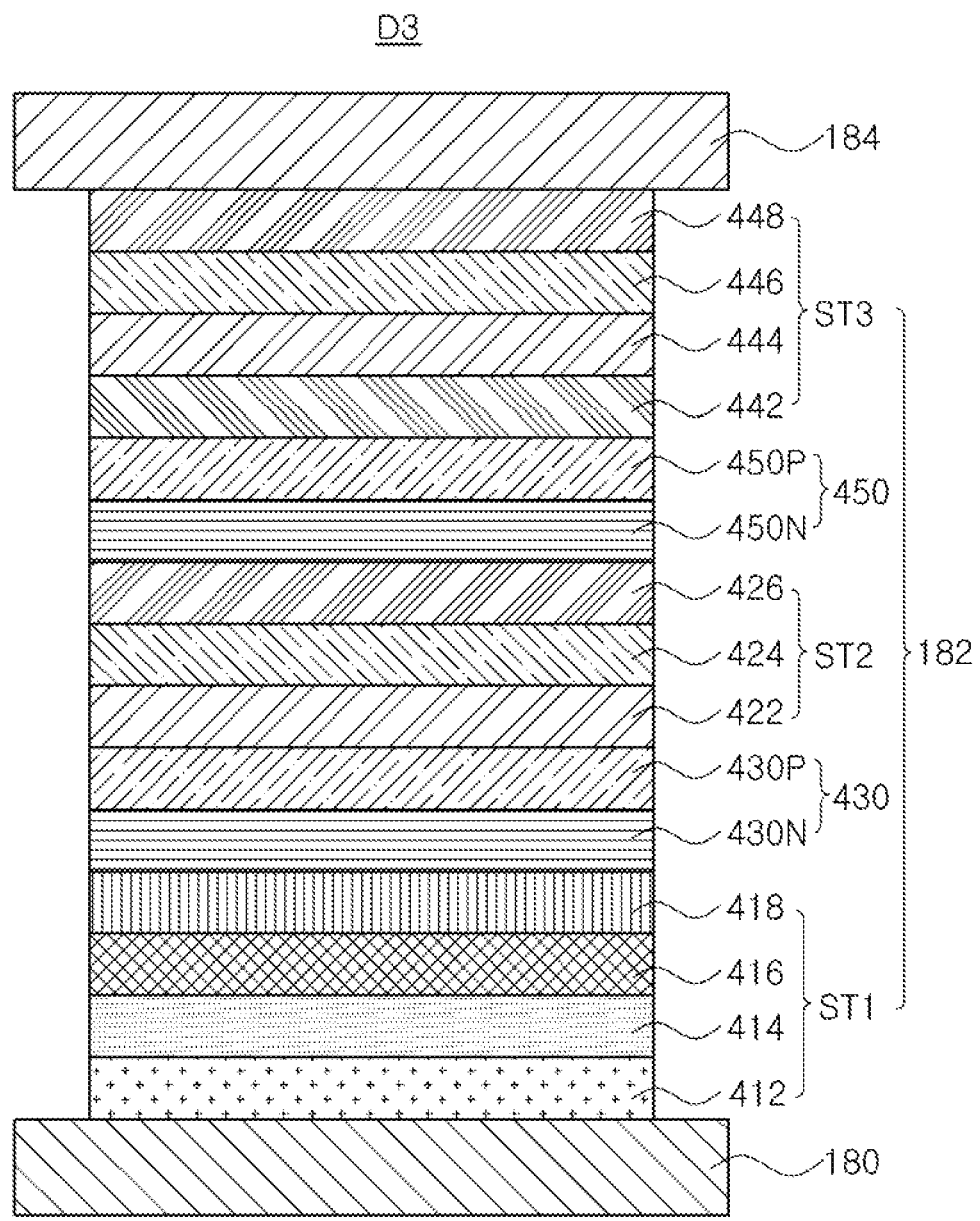
FIG. 3 is a schematic cross-sectional view of an organic light emitting diode according to a third embodiment of the present invention.

FIG. 3 is a schematic cross-sectional view of an organic light emitting diode according to a third embodiment of the present invention.

Referring to FIG. 3, an organic light emitting diode D3 includes a first electrode 180, a second electrode 184, an organic emitting layer 182 between the first and second electrodes 180 and 184 and including first to third emitting parts ST1, ST2 and ST3 and first and second CGLs 430 and 450. Alternatively, four or more emitting parts and three or more CGLs may be disposed between the first and second electrodes 180 and 184.

As mentioned above, the first electrode 180 is the anode for injecting a hole and includes a high work function conductive material, e.g., ITO, IZO or ZnO. The second electrode 184 is the cathode for injecting an electron and includes a low work function conductive material, e.g., Al, Mg or Al—Mg alloy.

The first and second CGLs 430 and 450 are positioned between the first and second emitting parts ST1 and ST2 and the second and third emitting parts ST2 and ST3, respectively. Namely, the first emitting part ST1, the first CGL 430, the second emitting part ST2, the second CGL 450 and the third emitting part ST3 are sequentially stacked on the first electrode 180. In other words, the first emitting part ST1 is positioned between the first electrode 180 and the first CGL 430, and the second emitting part ST2 is positioned between the First and Second CGLs 430 and 450. In addition, the third emitting part ST3 is positioned between the second electrode 184 and the second CGL 450.

The first emitting part ST1 may include an HIL 412, a first HTL 414, a first EML 416 and a first ETL 418 sequentially stacked on the first electrode 180. Namely, the HIL 412 and the first HTL 414 are positioned between the first electrode 180 and the first EML 416, and the HIL 412 is positioned between the first electrode 180 and the first HTL 414. In addition, the first ETL 418 is positioned between the first EML 416 and the first CGL 430.

The HIL 412, the first HTL 414, the first EML 416 and the first ETL 418 may have substantially the same property and structure as those in FIG. 2. For example, the first EML 416 may be a blue EML such that the first emitting part ST1 may have an emission peak range of about 440 to 480 nm.

The second emitting part ST2 may include a second HTL 422, a second EML 424 and a second ETL 426. The second HTL 422 is positioned between the first CGL 430 and the second EML 424, and the second ETL 426 is positioned between the second EML 424 and the second CGL 450.

The second HTL 422, second EML 424 and the second ETL 426 may have substantially the same property and structure as those in FIG. 2. For example, the second EML 424 may be a yellow-green EML such that the second emitting part ST2 may have an emission peak range of about 510 to 590 nm.

The third emitting part ST3 may include a third HTL 442, a third EML 444, a third ETL 446 and an EIL 448. The third HTL 442 is positioned between the second CGL 450 and the third EML 444, and the third ETL 446 is positioned between the third EML 444 and the second electrode 184. In addition, the EIL 448 is positioned between the third ETL 446 and the second electrode 184.

The third HTL 442, the third ETL 446 and the EIL 448 may have substantially the same property and structure as the second HTL 422, the second ETL 426 and the EIL 428 in FIG. 2.

The third EML 444 may have substantially the same property as the first EML 416 or the second EML 424. For example, the third EML 444 may be a blue EML such that the third emitting part ST3 may have an emission peak range of about 440 to 480 nm.

The first CGL 430 is positioned between the first emitting part ST1 and the second emitting part ST2, and the second CGL 450 is positioned between the second emitting part ST2 and the third emitting part ST3. Each of the first and second CGLs 430 and 450 may be a P-N junction type CGL. The first CGL 430 includes an N-type CGL 430N and a P-type CGL 430P, and the second CGL 450 includes an N-type CGL 450N and a P-type CGL 450P.

In the first CGL 430, the N-type CGL 430N is positioned between the first ETL 418 and the second HTL 422, and the P-type CGL 430P is positioned between the N-type CGL 430N and the second HTL 422.

In the second CGL 450, the N-type CGL 450N is positioned between the second ETL 426 and the third HTL 442, and the P-type CGL 450P is positioned between the N-type CGL 450N and the third HTL 442.

Each of the first and second CGLs 430 and 450 generates a charge or separates a charge into a hole and an electron such that the hole and the electron are provided into the first to third emitting parts ST1 to ST3.

Namely, in the first CGL 430, the N-type CGL 430N provides the electron into the first ETL 418 of the first emitting part ST1, and the P-type CGL 430P provide the hole into the second HTL 422 of the second emitting part ST2. In addition, in the second CGL 450, the N-type CGL 450N provides the electron into the second ETL 426 of the second emitting part ST2, and the P-type CGL 450P provide the hole into the third HTL 442 of the third emitting part ST3.

Each of the P-type CGLs 430P and 450P may include an organic material and a dopant, e.g., a metal or a p-type dopant. For example, the metal as the dopant may be selected from the group consisting of Al, Cu, Fe, Pb, Zn, Au, Pt, W, In, Mo, Ni, Ti and their alloy. In addition, the generally known materials may be used as the p-type dopant and the organic material. For example, the p-type dopant may be selected from the group consisting of $F_4$-TCNQ, iodine, $FeCl_3$, $FeF_3$ and $SbCl_5$, and the organic material may be selected from the group consisting of NPB, TPD, N,N, N',N'-tetranaphthalenyl-benzidine (TNB) and HAT-CN.

When the electrons are transported from the N-type CGLs 430N and 450N into the first and second ETLs 418 and 426, the driving voltage is increased because of a lowest unoccupied molecular orbital (LUMO) energy level difference between each of the first and second ETLs 418 and 426 and each of the N-type CGLs 430N and 450N.

To overcome the above problem, at least one of the first and second ETLs 418 and 426 and the N-type CGLs 430N and 450N includes an organic compound represented in Formula 1 (or Formula 2). In addition, each of the first and second ETLs 418 and 426 and the N-type CGLs 430N and 450N may further include a dopant, e.g., alkali metal, alkali metal compound, alkali earth metal or alkali earth metal compound.

For example, the dopant may include one of Liq, LiF, NaF, KF, RbF, CsF, FrF, $BeF_2$, $MgF_2$, $CaF_2$, $SrF_2$, $BaF_2$ and $RaF_2$. The dopant may have a weight % of about 1 to 20 with respect to the organic compound, but it is not limited thereto.

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased. Moreover, since the triazin core and the bipyridine moiety are separated by the at least one linker, the electron localization problem is prevented such that the electron uniformly exists in the organic compound. As a result, the electron from a cathode or an N-type charge generation layer (CGL) is efficiently injected or transported into an electron transporting layer (ETL) or an emitting material layer (EML). Accordingly, when the organic compound is used for at least one of an electron injection layer (EIL), the ETL and the N-type CGL of an organic light emitting diode, the electron injection/transporting property in the organic light emitting diode is increased such that there are advantages in the driving voltage, the lifetime and the emitting efficiency.

In addition, since the organic compound of the present invention includes the nitrogen atom having a relatively electron rich $sp^2$ hybrid orbital, the nitrogen atom in the organic compound is combined or bonded with the dopant, e.g., alkali metal, alkali metal compound, alkali earth metal or alkali earth metal compound, in the N-type CGL to form a gap state. As a result, the electron is efficiently transported from the N-type CGL into the ETL.

Figure 4:
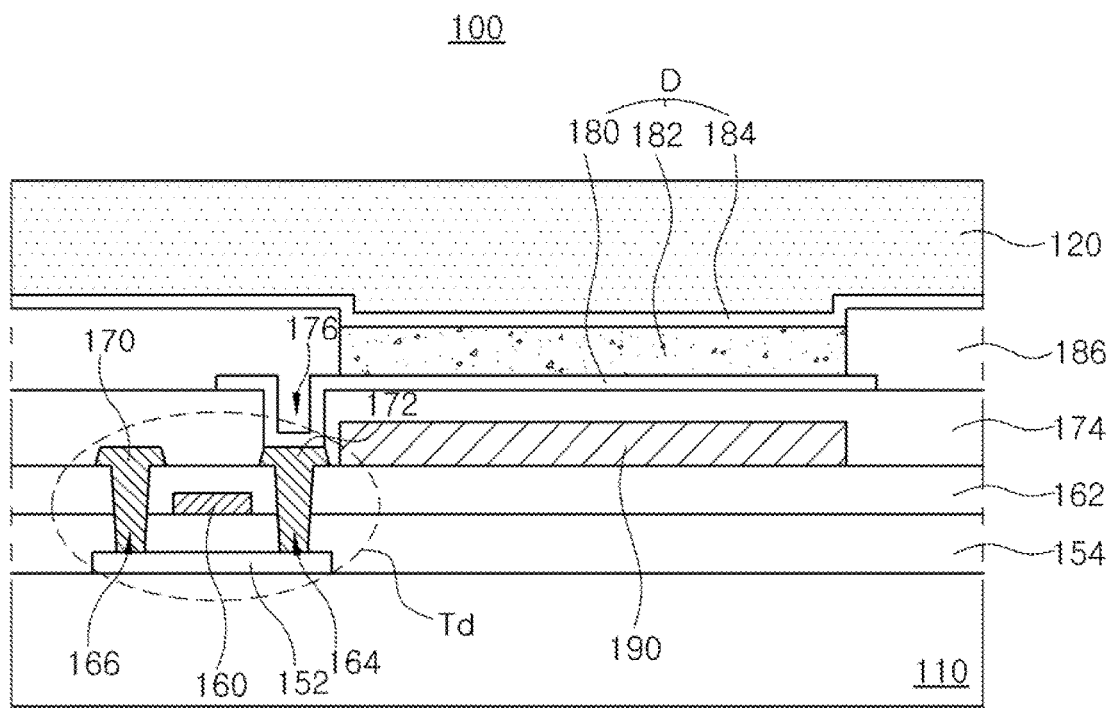
FIG. 4 is a schematic cross-sectional view of an OLED device according to another embodiment of the present invention.

FIG. 4 is a schematic cross-sectional view of an OLED device according to the present invention.

As shown in FIG. 4, an OLED device 100 includes a substrate 110, an organic light emitting diode D over the substrate 110, and an encapsulation film 120 covering the organic light emitting diode D.

A driving thin film transistor (TFT) Td is disposed on the substrate 110, and the organic light emitting diode D is connected to the driving TFT Td.

A gate line and a data line are disposed on or over the substrate 110 and cross each other to define a pixel region. In addition, a power line, which is parallel to and spaced apart from the gate line or the data line, a switching TFT, which is electrically connected to the gate line and the data line, and a storage capacitor, which is connected to the power line and an electrode of the switching TFT may be formed on or over the substrate 110.

The driving TFT Td is connected to the switching TFT and includes a semiconductor layer 152, a gate electrode 160, a source electrode 170 and a drain electrode 172.

The semiconductor layer 152 is formed on the substrate 110. The semiconductor layer 152 may be formed of an oxide semiconductor material or a poly-silicon.

When the semiconductor layer 152 includes the oxide semiconductor material, a light-shielding pattern may be formed under the semiconductor layer 152. The light to the semiconductor layer 152 is shielded or blocked by the light-shielding pattern such that thermal degradation of the semiconductor layer 152 can be prevented. On the other hand, when the semiconductor layer 152 includes polycrystalline silicon, impurities may be doped into both sides of the semiconductor layer 152.

A gate insulating layer 154 is formed on the semiconductor layer 152. The gate insulating layer 154 may be formed of an inorganic insulating material such as silicon oxide or silicon nitride.

The gate electrode 160, which is formed of a conductive material, e.g., metal, is formed on the gate insulating layer 154 to correspond to a center of the semiconductor layer 152. The gate electrode 160 is connected to the switching TFT.

An interlayer insulating layer 162, which is formed of an insulating material, is formed on an entire surface of the substrate 110 including the gate electrode 160. The interlayer insulating layer 162 may be formed of an inorganic insulating material, e.g., silicon oxide or silicon nitride, or an organic insulating material, e.g., benzocyclobutene or photo-acryl.

The interlayer insulating layer 162 includes first and second contact holes 164 and 166 exposing both sides of the semiconductor layer 152. The first and second contact holes 164 and 166 are positioned at both sides of the gate electrode 160 to be spaced apart from the gate electrode 160.

The source electrode 170 and the drain electrode 172, which are formed of a conductive material, e.g., metal, are formed on the interlayer insulating layer 162. The source electrode 170 and the drain electrode 172 are spaced apart from each other with respect to the gate electrode 160 and respectively contact both sides of the semiconductor layer 152 through the first and second contact holes 164 and 166. The source electrode 170 is connected to the power line.

In the driving TFT Td, the gate electrode 160, the source electrode 170 and the drain electrode 172 are positioned over the semiconductor layer 152. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

The switching TFT may have substantially the same structure as the driving TFT Td.

The OLED device 100 may further include a color filter 190. For example, the color filter 190 absorbs a part of the red, green and blue light. A red color filter pattern, a green color filer pattern and a blue color filter pattern may be disposed in each pixel region. Due to the color filter pattern 190, the OLED device 100 provides a full-color image.

In FIG. 4, the color filter 190 is positioned between the light organic emitting diode D and the interlayer insulating layer 162 (or the substrate 110). Namely, the OLED device 100 is the bottom-emission type. Alternatively, in the top-emission type OLED device, the color filter 190 may be positioned on or over the organic light emitting diode D, e.g., over the second electrode 184. For example, the color filter 190 may have a thickness of about 2 to 5 micrometers. The color filter 190 may be used with the tandem structure white organic light emitting diode D in FIG. 2 or FIG. 3.

A passivation layer 174, which includes a drain contact hole 176 exposing the drain electrode 172 of the driving TFT Td, is formed to cover the driving TFT Td and the color filter 190.

A first electrode 180, which is connected to the drain electrode 172 of the driving TFT Td through the drain contact hole 176, is separately formed on the passivation layer 174 in each pixel region.

The first electrode 180 may be an anode and may be formed of a conductive material having a relatively high work function. For example, the first electrode 180 may be formed of a transparent conductive material such as ITO, IZO or ZnO.

When the OLED device 100 of the present invention is a top-emission type, a reflection electrode or a reflection layer may be formed under the first electrode 180. For example, the reflection electrode or the reflection layer may be formed of aluminum (Al), silver (Ag), nickel (Ni) or aluminum-palladium-copper (APC) alloy.

A bank layer 186, which covers edges of the first electrode 180, is formed on the passivation layer 174. The bank 186 exposes a center of the first electrode 180 in the pixel region.

An organic emitting layer 182 is formed on the first electrode 180. As explained below, the organic emitting layer includes a single emitting part or at least two emitting parts (the tandem structure).

A second electrode 184 is formed over the substrate 110 including the emitting layer 182. The second electrode 184 is positioned at an entire surface of the display area. The second electrode 184 may be a cathode and may be formed of a conductive material having a relatively low work function. For example, the second electrode 184 may be formed of Al, Mg or Al—Mg alloy.

The first electrode 180, the emitting layer 182 and the second electrode 184 constitute the organic light emitting diode D.

The encapsulation film 120 is formed on the organic light emitting diode D to prevent penetration of moisture into the organic light emitting diode D. For example, the encapsulation film 120 may has a triple-layered structure of a first inorganic layer, an organic layer and a second inorganic layer. However, it is not limited thereto.

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased.

Moreover, since the nitrogen atom of the triazin core in the organic compound is combined or bonded with the alkali metal or the alkali earth metal as a dopant in the ETL or an N-type CGL to form a gap state, the electron transporting property of the ETL or the N-type CGL is further improved.

Accordingly, when the organic compound is used for at least one of an electron injection layer (EIL), the ETL and the N-type CGL of an organic light emitting diode, the electron injection/transporting property in the organic light emitting diode is increased such that there are advantages in the driving voltage, the lifetime and the emitting efficiency.

Synthesis

1. Synthesis of the Compound ET_35

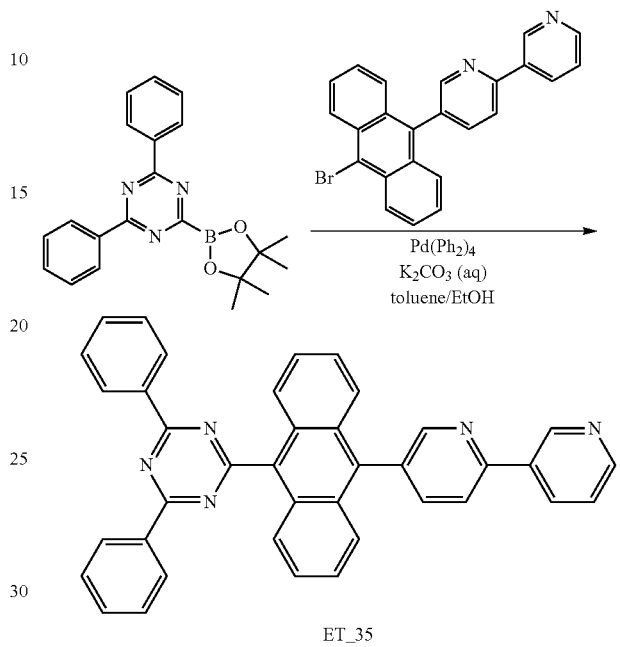

ET_35

Under the nitrogen condition, 2-(4,4,5,5-tetramethyl-1,3,2-dioxaborolan-2-yl)-4,6-diphenyl-1,3,5-triazine (5 g, 13.92 mmol), 5-(10-bromoanthracen-9-yl)-2-(pyridin-3-yl)pyridine (4.75 g, 11.6 mmol), tetrakistriphenylphosphine palladium (0) (Pd(PPh$_3$)$_4$) (0.53 g, 0.46 mmol), 4M potassium carbonate aqueous solution (10 mL), toluene (30 mL) and ethanol (10 mL) were refluxed and stirred for 12 hrs. After completion of the reaction, the distilled water (H$_2$O, 50 mL) was added and stirred for 3 hrs. The mixture was filtered under the reduced pressure and separated by a column chromatography using methylene chloride (MC) and hexane as an eluent. The resultant was crystallized using MC such that the compound ET_35 (5.30 g, yield 81.2%) was obtained.

2. Synthesis of ET$_{13}$ 243

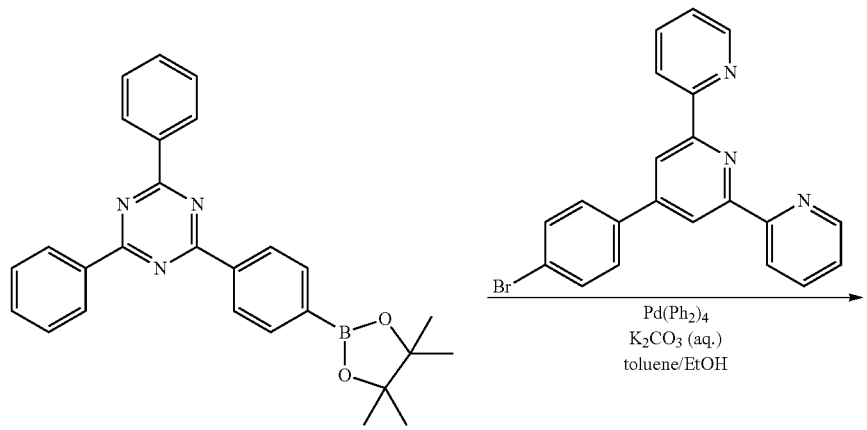

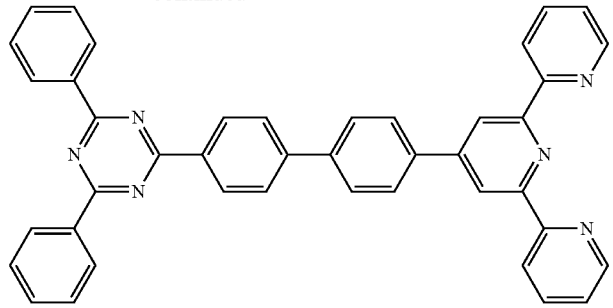

ET_243

Under the nitrogen condition, 2-(4-(4,4,5,5-tetramethyl-1,3,2-dioxaborolan-2-yl)phenyl)-4,6-diphenyl-1,3,5-triazine (5 g, 11.49 mmol), 2-(4-(4-bromophenyl)-6-(pyridin-2-yl)pyridin-2-yl)pyridine (3.70 g, 9.57 mmol), tetrakistriphenylphosphine palladium (0) (Pd(PPh$_3$)$_4$) (0.53 g, 0.46 mmol), 4M potassium carbonate aqueous solution (10 mL), toluene (30 mL) and ethanol (10 mL) were refluxed and stirred for 12 hrs. After completion of the reaction, the distilled water (H$_2$O, 50 mL) was added and stirred for 3 hrs. The mixture was filtered under the reduced pressure and separated by a column chromatography using methylene chloride (MC) and hexane as an eluent. The resultant was crystallized using MC such that the compound ET$_{13}$ 243 (5.20 g, yield 88.2%) was obtained.

3. Synthesis of ET_271

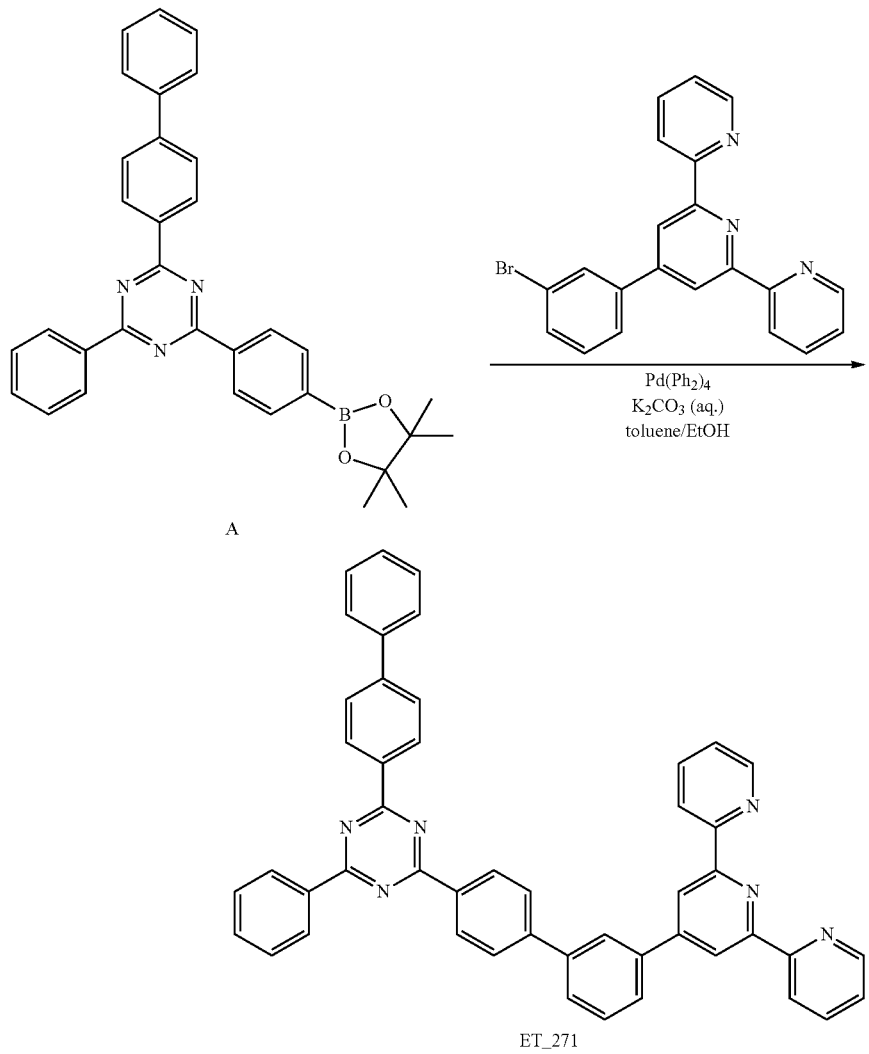

ET_271

Under the nitrogen condition, the compound A (5 g, 9.78 mmol), 2-(4-(3-bromophenyl)-6-(pyridin-2-yl)pyridin-2-yl)pyridine (3.15 g, 8.14 mmol), tetrakistriphenylphosphine palladium (0) (Pd(PPh$_3$)$_4$) (0.53 g, 0.46 mmol), 4M potassium carbonate aqueous solution (10 mL), toluene (30 mL) and ethanol (10 mL) were refluxed and stirred for 12 hrs. After completion of the reaction, the distilled water (H$_2$O, 50 mL) was added and stirred for 3 hrs. The mixture was filtered under the reduced pressure and separated by a column chromatography using methylene chloride (MC) and hexane as an eluent. The resultant was crystallized using MC such that the compound ET$_{13}$ 271 (4.88 g, yield 86.7%) was obtained.

Organic Light Emitting Diode

1. Example 1 (Ex1)

An ITO layer is deposited and patterned on a substrate and washed to form the anode (2 mm*2 mm). The substrate is loaded in a vacuum chamber having a base pressure of 5~7*10$^{-8}$, and layers are sequentially deposited as below.
  (1) HIL: (HAT-CN, 50 Å),
  (2) HTL: first layer (NPD+N,N'-diphenyl-N-naphthyl-N'-biphenyl-1,1'-biphenyl-4,4"-diamine (10% doping), 1250 Å) and a second layer (TCTA, 200 Å),
  (3) EML: (9,10-di(naphthalen-2-yl)-anthracene+t-Bu-perylene (5% doping), 250 Å),
  (4) ETL: (2-[4-(9,10-Di-2-naphthalenyl-2-anthracenyl)phenyl]-1-phenyl-1H-benzimidazole, 250 Å),
  (5) EIL: (ET_243 compound, 100 Å), and
  (6) cathode: (Al, 2000 Å)

2. Comparative Example 1 (Ref 1)

Instead of the compound of ET$_{13}$ 243, the compound of Bphen (bathophenanthroline).

The EL property of the organic light emitting diode in "Example 1" and "Comparative Example 1" is measured using the current supply "KEITHLEY" and the photometer "PR 650" under the room temperature. The driving voltage, the external quantum efficiency (EQE) and the lifetime (T95) of the organic light emitting diodes of are measured and listed in Table 1. The current density, the EQE and the lifetime (L/L$_0$) are shown in FIGS. 5A to 5C.

TABLE 1

| | Current density [10 mA/cm$^2$] | | |
|---|---|---|---|
| | Volt [V] | EQE | T95 |
| Ex 1 | 100% | 101% | 107% |
| Ref 1 | 100% | 100% | 100% |

Figure 5A:
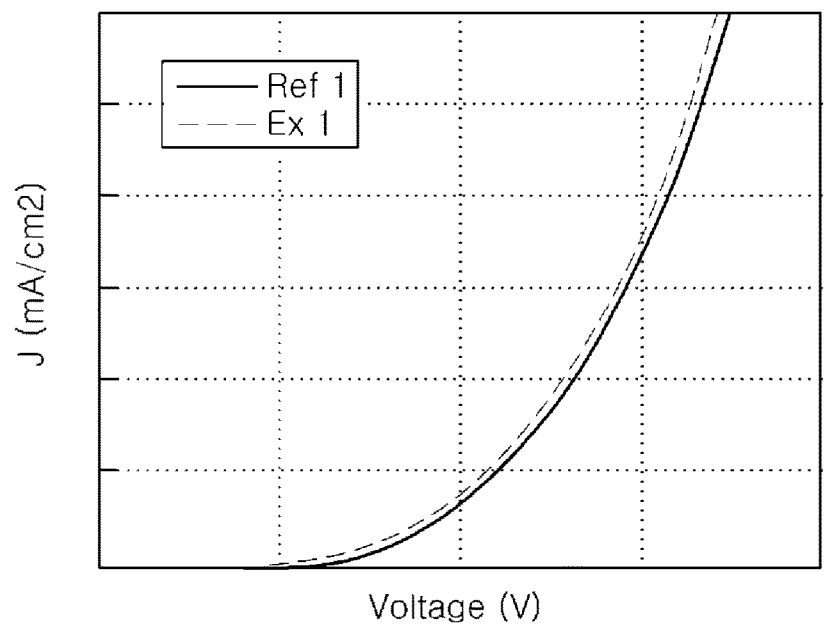
FIG. 5A, FIG. 5B and FIG. 5C are graphs showing emitting properties of an organic light emitting diode including an organic compound in an EIL.
Figure 5B:
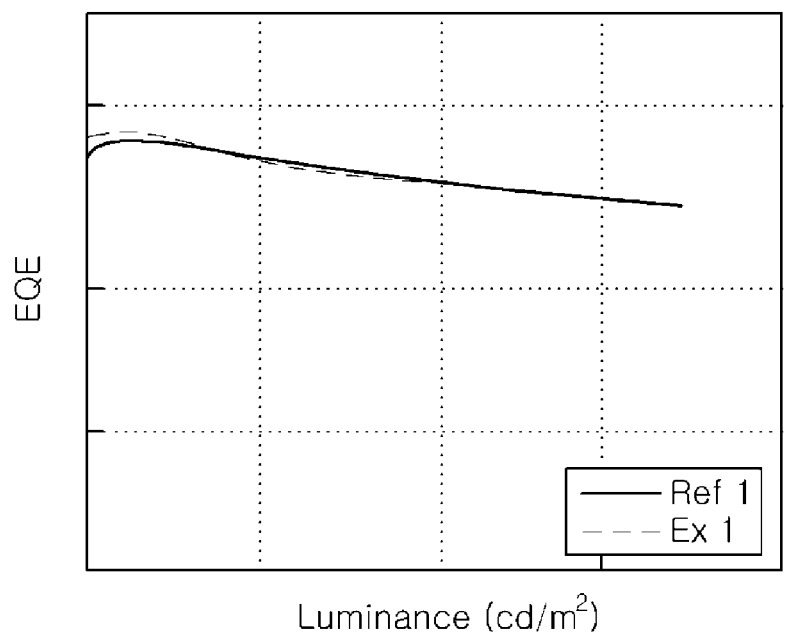
Figure 5C:
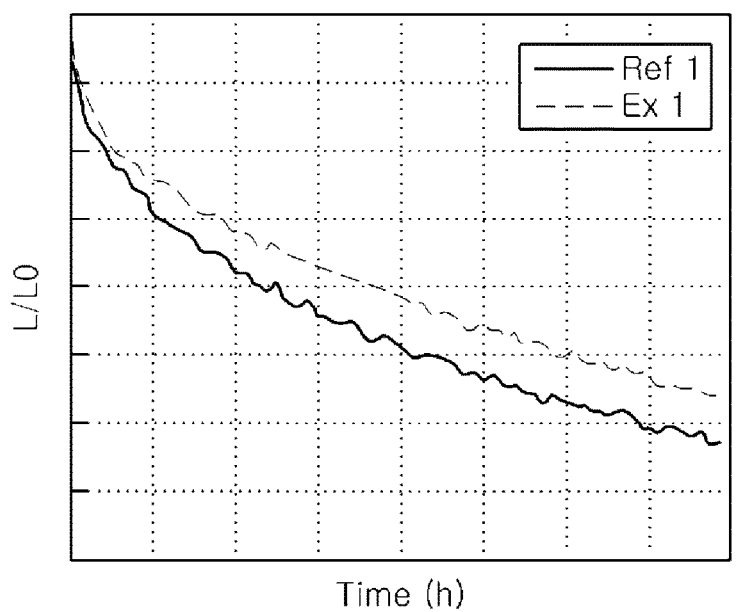

In comparison to "Comparative Example 1," Table 1 and FIGS. 5A to 5C show that the organic light emitting diode of the present invention (Ex 1) has advantages in the current density, the EQE and the lifetime.

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased. Moreover, since the triazin core and the bipyridine moiety are separated by the at least one linker, the electron localization problem is prevented such that the electron uniformly exists in the organic compound. Accordingly, when the ETL of the organic light emitting diode includes the organic compound of the present invention, the current from the cathode is efficiently injected into the EML such that there are advantages in the driving voltage, the lifetime and the emitting efficiency.

Tandem Structure Organic Light Emitting Diode

1. Example 2 (Ex2)

An ITO layer is deposited and patterned on a substrate and washed to form the anode (2 mm*2 mm). The substrate is loaded in a vacuum chamber having a base pressure of 5~7*10$^{-8}$, and layers are sequentially deposited as below.
  (1) HIL: (HAT-CN, 50 Å),
  (2) first HTL: first layer (NPD+N,N'-diphenyl-N-naphthyl-N'-biphenyl-1,1'-biphenyl-4,4"-diamine (10% doping), 1250 Å) and a second layer (TCTA, 200 Å),
  (3) first EML: (AND+t-Bu-perylene (5% doping), 250 Å),
  (4) first ETL: (2-[4-(9,10-Di-2-naphthalenyl-2-anthracenyl)phenyl]-1-phenyl-1H-benzimidazole, 250 Å),
  (5) first N-type CGL: (ET_35 compound+Li (2% doping), 100 Å),
  (6) first P-type CGL: (HAT-CN, 100 Å),
  (7) second HTL: first layer (NPD, 400 Å) and second layer (TCTA, 200 Å),
  (8) second EML: (BAlq+Ir(2-phq)$_3$ (10% doping, YG dopant), 300 Å),
  (9) second ETL: (2-[4-(9,10-Di-2-naphthalenyl-2-anthracenyl)phenyl]-1-phenyl-1H-benzimidazole, 250 Å),
  (10) second N-type CGL: (ET$_{13}$ 35 compound+Li (2% doping), 100 Å),
  (11) second P-type CGL: (HAT-CN, 100 Å),
  (12) third HTL: first layer (NPD, 900 Å) and second layer (TCTA, 100 Å),
  (13) third EML: (AND+t-Bu-perylene (5% doping), 250 Å),
  (14) third ETL: (2-[4-(9,10-Di-2-naphthalenyl-2-anthracenyl)phenyl]-1-phenyl-1H-benzimidazole, 350 Å),
  (15) EIL: (LiF, 10 Å), and
  (16) cathode: (Al, 200 Å)

2. Example 3 (Ex 3)

Instead of the compound of ET_35, the compound of ET_243 is used for the first and second N-type CGLs.

3. Example 4 (Ex 4)

Instead of the compound of ET_35, the compound of ET_271 is used for the first and second N-type CGLs.

4. Comparative Example 2 (Ref 2)

Instead of the compound of ET$_{13}$ 35, the compound of Bphen (bathophenanthroline) is used for the first and second N-type CGLs.

Figure 6A:
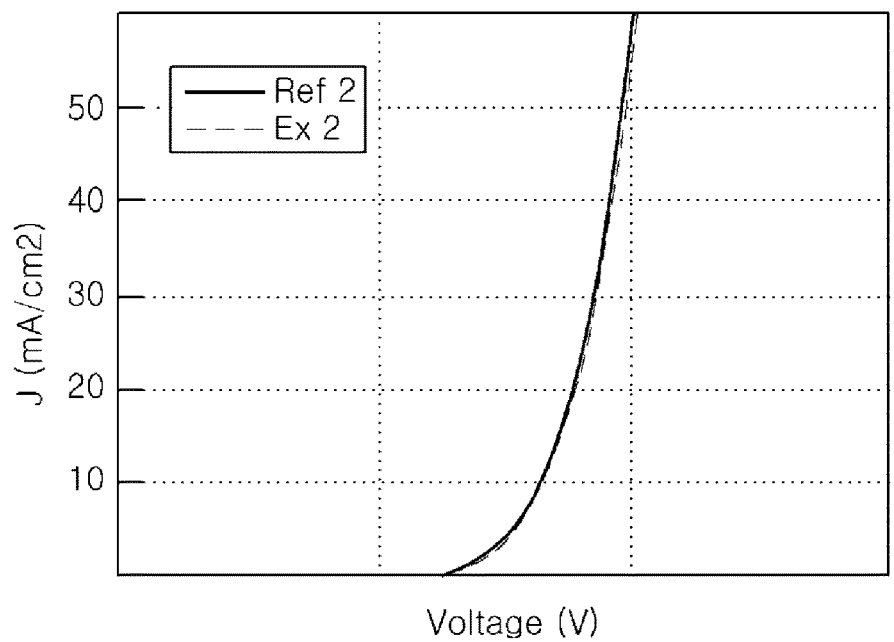
FIG. 6A, FIG. 6B and FIG. 6C are graphs showing emitting properties of an organic light emitting diode including an organic compound in an N-type CGL.
Figure 6B:
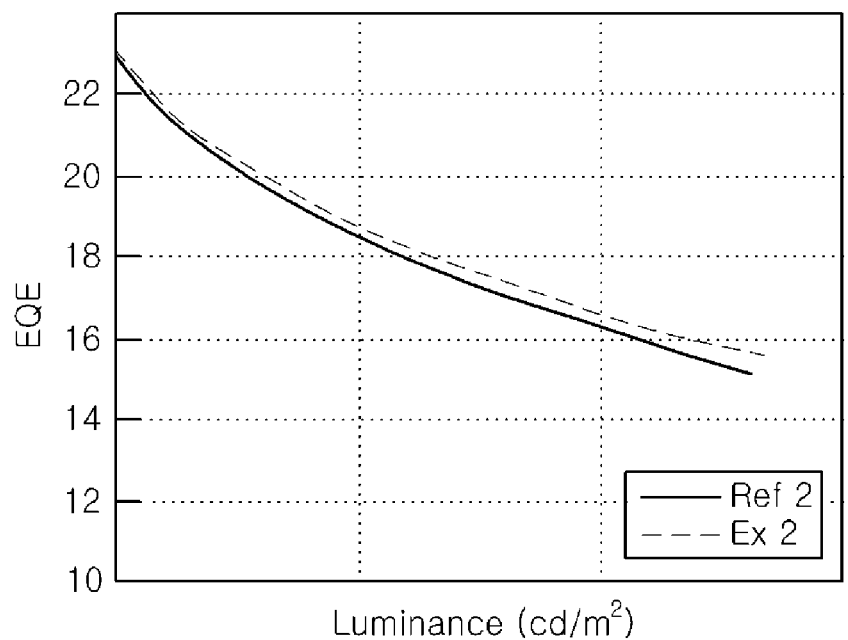
Figure 6C:
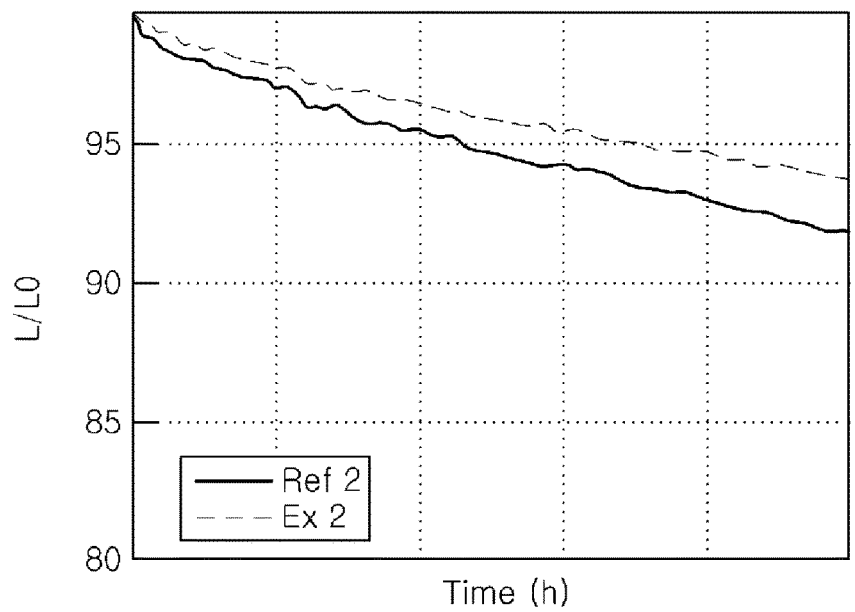
Figure 7A:
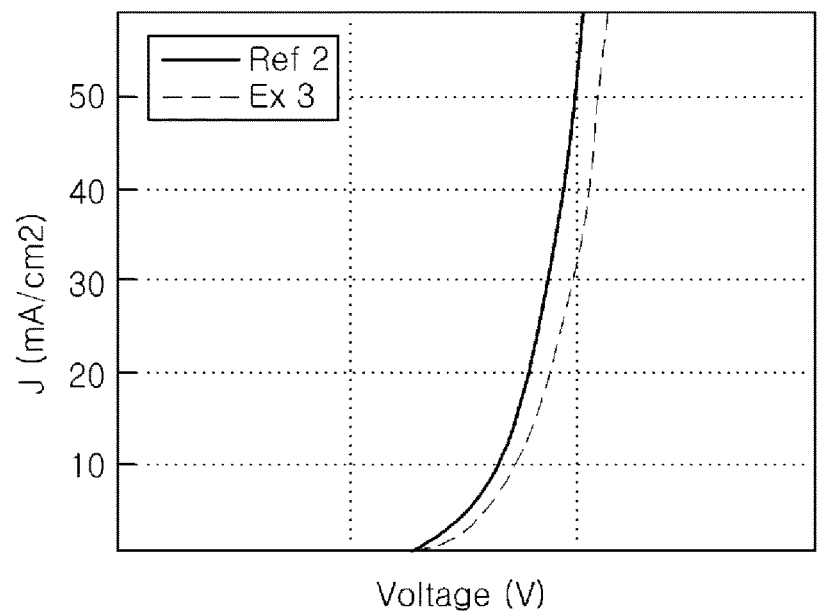
FIG. 7A, FIG. 7B and FIG. 7C are graphs showing emitting properties of an organic light emitting diode including an organic compound in an N-type CGL.
Figure 7B:
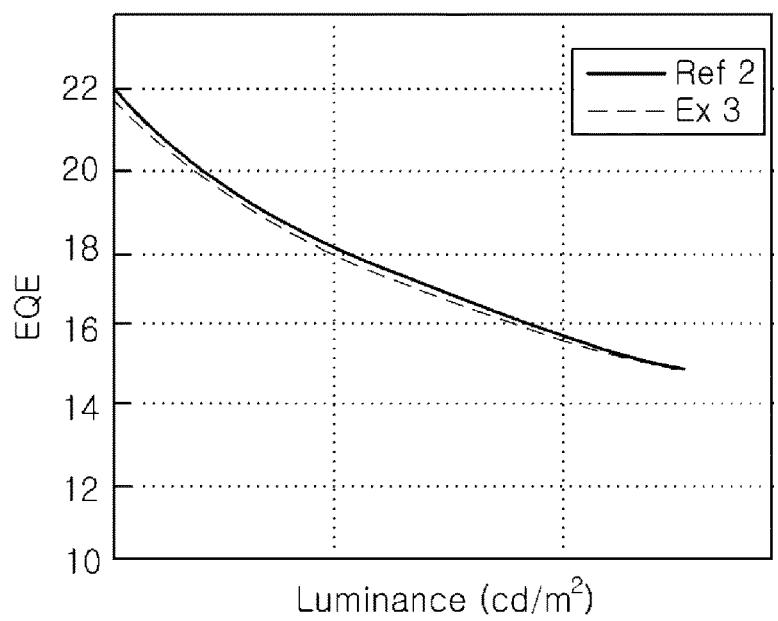
Figure 7C:
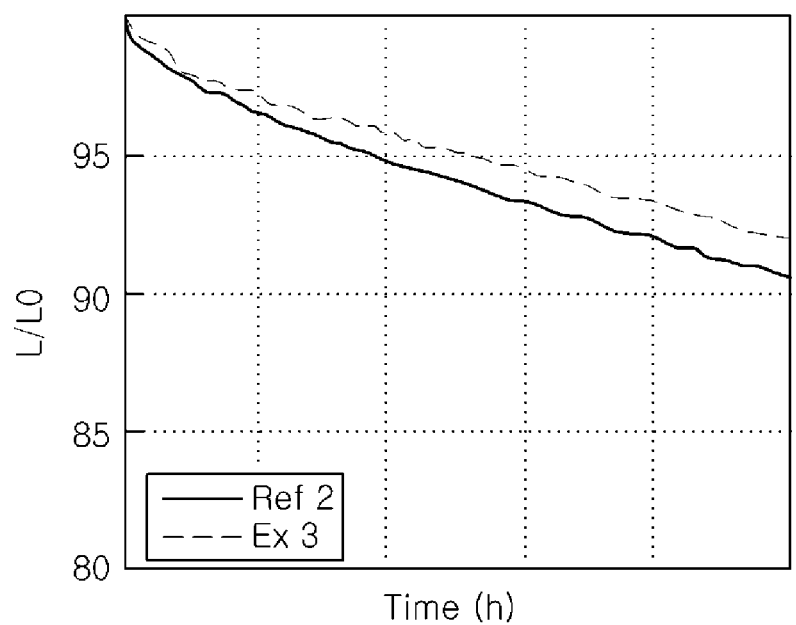
Figure 8A:
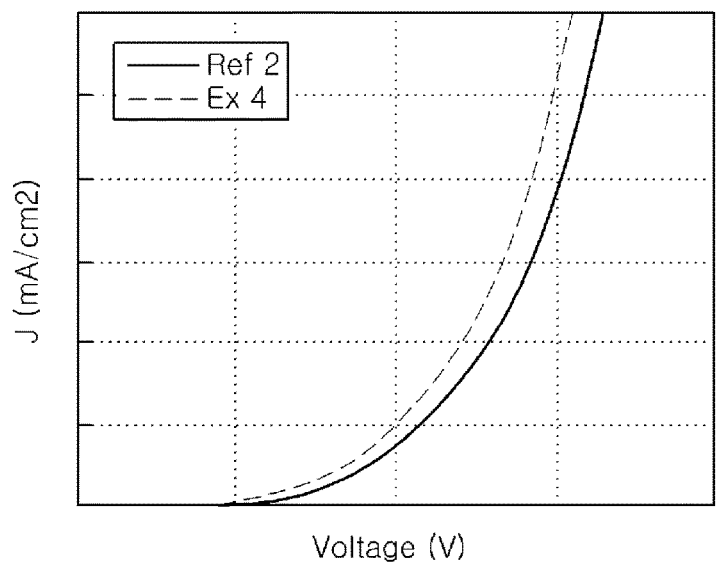
FIG. 8A, FIG. 8B and FIG. 8C are graphs showing emitting properties of an organic light emitting diode including an organic compound in an N-type CGL.
Figure 8B:
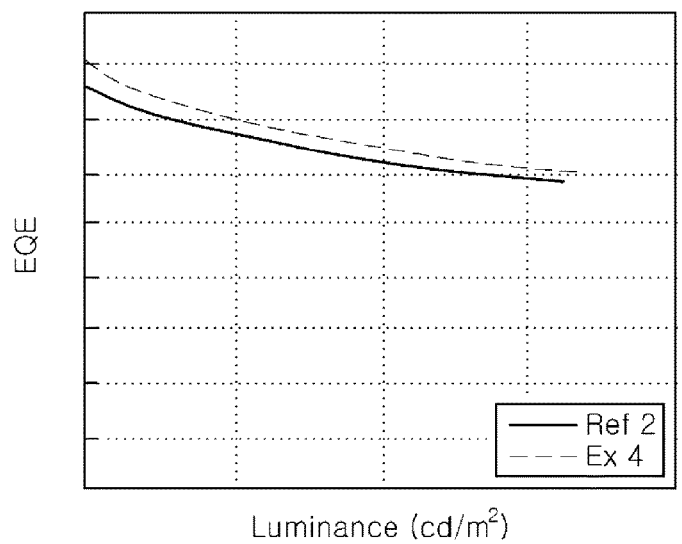
Figure 8C:
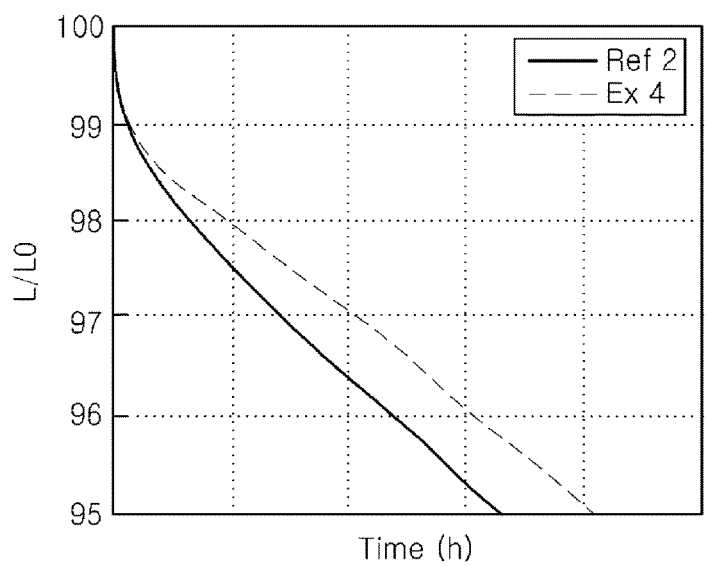

The EL property of the organic light emitting diode in "Example 2" to "Example 4" and "Comparative Example 2" is measured using the current supply "KEITHLEY" and the photometer "PR 650" under the room temperature. The driving voltage, the external quantum efficiency (EQE) and the lifetime (T95) of the organic light emitting diodes of are measured and listed in Table 2. The current density, the EQE and the lifetime (L/L$_0$) are shown in FIGS. 6A to 6C (comparison of "Ex2" and "Ref 2"), FIGS. 7A to 7C (comparison of "Ex3" and "Ref 2") and FIGS. 8A to 8C (comparison of "Ex4" and "Ref 2").

TABLE 2

|       | Current density [10 mA/cm²] | | |
|-------|---------|------|------|
|       | Volt [V] | EQE | T95 |
| Ex 2  | 100%    | 105% | 153% |
| Ex 3  | 93%     | 97%  | 143% |
| Ex 4  | 102%    | 104% | 124% |
| Ref 2 | 100%    | 100% | 100% |

In comparison to "Comparative Example 2," Table 2 and FIGS. 6A to 6C, FIGS. 7A to 7C and FIGS. 8A to 8C show that the organic light emitting diode of the present invention (Ex 2 to Ex 4) has advantages in the current density, the EQE and the lifetime. In "Ex2" and "Ex4," all of the properties are improved. In "Ex 3," the lifetime of the organic light emitting diode is improved (about 50%).

Since the organic compound of the present invention includes the triazin core having three nitrogen atoms, each of which have a rich electron property, an electron transporting (or mobility) property of the organic compound is increased such that the electron is efficiently transported by the organic compound. In addition, in the organic compound, the bipyridine moiety, which has high electronegativity, is connected (combined or linked) to the triazin core via at least one linker such that the electron transporting property of the organic compound is further increased. Moreover, since the triazin core and the bipyridine moiety are separated by the at least one linker, the electron localization problem is prevented such that the electron uniformly exists in the organic compound. Accordingly, the electron from the cathode or the N-type CGL is efficiently injected into the EML.

Further, since the organic compound of the present invention includes the nitrogen atom having a relatively electron rich sp² hybrid orbital, the nitrogen atom in the organic compound is combined or bonded with the dopant, e.g., alkali metal, alkali metal compound, alkali earth metal or alkali earth metal compound, in the N-type CGL to form a gap state. As a result, the electron is efficiently transported from the N-type CGL into the ETL.

Namely, when the organic compound of the present invention is used for at least one of the EIL, ETL and the N-type CGL, the driving voltage is reduced, the lifetime and the emitting efficiency are improved.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic compound, having the following structure:

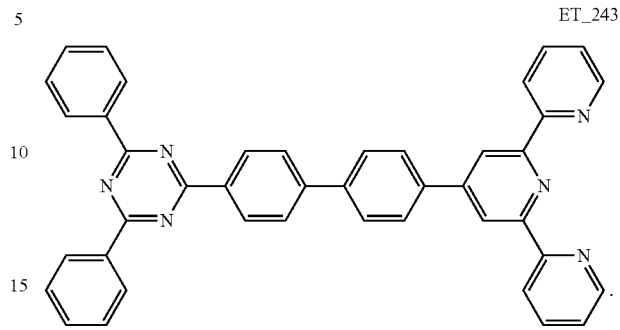

ET_243

2. An organic light emitting diode, comprising:
   a first electrode and a second electrode facing each other;
   an emitting material layer between the first electrode and the second electrode; and
   an electron injection layer between the emitting material layer and the second electrode and including the organic compound of claim 1.

3. The organic light emitting diode according to claim 2, wherein the electron injection layer further includes an alkali metal, an alkali metal compound, an alkali earth metal or an alkali earth metal compound.

4. The organic light emitting diode according to claim 2, further comprising an electron transporting layer between the emitting material layer and the electron injection layer, wherein the electron transporting layer includes the organic compound or an electron transporting material doped with the organic compound.

5. An organic light emitting diode, comprising:
   a first electrode and a second electrode facing each other;
   a first emitting part between the first and second electrodes and including a first emitting material layer and an electron transporting layer;
   a second emitting part between the first emitting part and the second electrode and including a second emitting material layer; and
   a first charge generation layer between the first emitting part and the second emitting part,
   wherein at least one of the electron transporting layer and the first charge generation layer includes the organic compound of claim 1.

6. The organic light emitting diode according to claim 5, wherein one of the first and second emitting parts emits blue, and the other one of the first and second emitting parts emits yellow-green.

7. The organic light emitting diode according to claim 5, wherein the first charge generation layer includes a P-type charge generation layer and an N-type charge generation layer between the P-type charge generation layer and the electron transporting layer, and wherein the organic compound is included in the N-type charge generation layer, and the N-type charge generation layer further includes an alkali metal, an alkali metal compound, an alkali earth metal or an alkali earth metal compound.

8. The organic light emitting diode according to claim 5, wherein the electron transporting layer includes the organic compound or an electron transporting material doped with the organic compound.

9. The organic light emitting diode according to claim 5, further comprising:
   a third emitting part between the second emitting part and the second electrode and including a third emitting material layer; and a second charge generation layer between the second emitting part and the third emitting part, wherein the second charge generation layer includes the organic compound.

10. An organic light emitting display device, comprising:
a substrate;
the organic light emitting diode of claim 2; and
a thin film transistor between the substrate and the organic light emitting diode and connected to the organic light emitting diode.

11. The organic light emitting display device according to claim 10, wherein the electron injection layer further includes an alkali metal, an alkali metal compound, an alkali earth metal or an alkali earth metal compound.

12. The organic light emitting display device according to claim 10, further comprising an electron transporting layer between the emitting material layer and the electron injection layer, wherein the electron transporting layer includes the organic compound or an electron transporting material doped with the organic compound.

13. An organic light emitting display device, comprising:
a substrate;
the organic light emitting diode of claim 5; and
a thin film transistor between the substrate and the organic light emitting diode and connected to the organic light emitting diode.

14. The organic light emitting display device according to claim 13, wherein one of the first and second emitting parts emits blue, and the other one of the first and second emitting parts emits yellow-green.

15. The organic light emitting display device according to claim 13, wherein the first charge generation layer includes a P-type charge generation layer and an N-type charge generation layer between the P-type charge generation layer and the electron transporting layer, and wherein the organic compound is included in the N-type charge generation layer, and the N-type charge generation layer further includes an alkali metal, an alkali metal compound, an alkali earth metal or an alkali earth metal compound.

16. The organic light emitting display device according to claim 13, wherein the electron transporting layer includes the organic compound or an electron transporting material doped with the organic compound.

17. The organic light emitting display device according to claim 13, further comprising:
a third emitting part between the second emitting part and the second electrode and including a third emitting material layer; and
a second charge generation layer between the second emitting part and the third emitting part,
wherein the second charge generation layer includes the organic compound.

18. The organic light emitting display device according to claim 13, further comprising a color filter between the substrate and the organic light emitting diode or over the second electrode.

* * * * *